US009192780B2

(12) United States Patent
McDaniel

(10) Patent No.: US 9,192,780 B2
(45) Date of Patent: *Nov. 24, 2015

(54) LOW INTENSITY LIGHT THERAPY FOR TREATMENT OF RETINAL, MACULAR, AND VISUAL PATHWAY DISORDERS

(75) Inventor: David H. McDaniel, Virginia Beach, VA (US)

(73) Assignee: L'OREAL, Paris (FR)

( * ) Notice: Subject to any disclaimer, the term of this patent is extended or adjusted under 35 U.S.C. 154(b) by 389 days.

This patent is subject to a terminal disclaimer.

(21) Appl. No.: 11/346,622

(22) Filed: Feb. 3, 2006

(65) Prior Publication Data

US 2006/0184214 A1    Aug. 17, 2006

Related U.S. Application Data

(60) Continuation-in-part of application No. 11/119,378, filed on May 2, 2005, now Pat. No. 7,201,765, which is a division of application No. 09/933,870, filed on Aug. 22, 2001, now Pat. No. 6,887,260, which is a continuation-in-part of application No. 09/203,178, filed on Nov. 30, 1998, now Pat. No. 6,283,956.

(51) Int. Cl.
*A61B 19/00* (2006.01)
*A61N 5/06* (2006.01)
*A61N 5/067* (2006.01)

(52) U.S. Cl.
CPC ............ *A61N 5/0616* (2013.01); *A61N 5/0613* (2013.01); *A61N 5/0601* (2013.01); *A61N 2005/0605* (2013.01); *A61N 2005/067* (2013.01); *A61N 2005/0609* (2013.01); *A61N 2005/0652* (2013.01); *A61N 2005/0653* (2013.01); *A61N 2005/0654* (2013.01); *A61N 2005/0662* (2013.01)

(58) Field of Classification Search
CPC ......... A61N 5/00; A61N 5/06; A61N 5/0613; A61N 5/062; A61N 5/0622; A61N 2005/0658; A61N 2005/0659; A61N 2005/0661; A61N 2005/0662; A61F 9/00
USPC .................. 606/3, 4; 607/88, 89; 128/898
See application file for complete search history.

(56) References Cited

U.S. PATENT DOCUMENTS

| | | | |
|---|---|---|---|
| 3,499,437 A | 3/1970 | Balamuth | |
| 3,876,907 A | 4/1975 | Widmayer | |
| 3,930,335 A | 1/1976 | Widmayer | |
| 4,069,823 A | 1/1978 | Isakov et al. | |
| 4,309,989 A | 1/1982 | Fahim | |
| 4,458,678 A | 7/1984 | Yannas et al. | |
| 4,558,700 A | 12/1985 | Mutzhas | |
| 4,603,496 A | 8/1986 | Latz et al. | |
| 4,621,287 A | 11/1986 | Reitmeier et al. | |
| 4,628,422 A | 12/1986 | Ewald | |
| 4,646,743 A | 3/1987 | Parris | |
| 4,753,958 A | 6/1988 | Weinstein et al. | |
| 4,764,379 A | 8/1988 | Sanders et al. | |
| 4,767,402 A | 8/1988 | Kost et al. | |
| 4,781,924 A | 11/1988 | Lee et al. | |
| 4,822,335 A | 4/1989 | Kawai et al. | |
| 4,836,203 A | 6/1989 | Muller et al. | |
| 4,837,027 A | 6/1989 | Lee et al. | |
| 4,880,001 A | 11/1989 | Weinberg | |
| 4,888,354 A | 12/1989 | Chang et al. | |
| 4,907,132 A | 3/1990 | Parker | |
| 4,930,504 A * | 6/1990 | Diamantopoulos et al. | 607/88 |
| 4,932,934 A | 6/1990 | Dougherty et al. | |
| 4,935,665 A | 6/1990 | Murata | |
| 4,969,912 A | 11/1990 | Kelman et al. | |
| 5,001,556 A | 3/1991 | Nakamura et al. | |
| 5,012,609 A | 5/1991 | Ignatius et al. | |
| 5,016,615 A | 5/1991 | Driller et al. | |
| 5,021,452 A | 6/1991 | Labbe et al. | |
| 5,034,613 A | 7/1991 | Denk et al. | |
| 5,037,432 A | 8/1991 | Molinari | |
| 5,071,416 A * | 12/1991 | Heller et al. | 606/3 |
| 5,150,704 A | 9/1992 | Tatebayashi et al. | |
| 5,171,215 A | 12/1992 | Flanagan | |
| 5,198,465 A | 3/1993 | Dioguardi | |
| 5,226,907 A | 7/1993 | Tankovich | |
| 5,231,975 A | 8/1993 | Bommannan et al. | |
| 5,257,173 A | 10/1993 | Ohmamyuda et al. | |

(Continued)

FOREIGN PATENT DOCUMENTS

| | | |
|---|---|---|
| CA | 2 410 962 | 12/2001 |
| EP | 0-159-446 A2 | 10/1985 |
| EP | 0-298-661 A2 | 1/1989 |
| EP | 0320080 | 6/1989 |
| EP | 1839705 A1 | 3/2007 |
| EP | 1818077 A1 | 8/2007 |
| EP | 1837050 A1 | 9/2007 |
| EP | 1839704 A1 | 10/2007 |
| EP | 1842571 A2 | 10/2007 |
| EP | 1857145 A1 | 11/2007 |

(Continued)

OTHER PUBLICATIONS

Monfrecola, G. et al. (1987) "Topical Hematoporphyrin Plus UVA for Treatment of Alopecia Areata", *Photodermatology* 4:305-306.

(Continued)

*Primary Examiner* — Ahmed Farah
(74) *Attorney, Agent, or Firm* — Oblon, McClelland, Maier & Neustadt, L.L.P.

(57) ABSTRACT

Disclosed is a system and method for treatment of cells and, in particular, visual pathway disorders. More particularly, the disclosed invention is directed toward the photomodulation and/or photorejuvenation of retinal epithelial cells, to treat a variety of vision disorders. The process of treating retinal cells to reduce or reverse the effects of visual pathway disorders employs a narrowband source of multichromatic light applied to the retinal cells to deliver a very low energy fluence.

23 Claims, 8 Drawing Sheets

(56) References Cited

U.S. PATENT DOCUMENTS

| | | |
|---|---|---|
| 5,259,380 A | 11/1993 | Mendes et al. |
| 5,262,401 A | 11/1993 | Vogel et al. |
| 5,266,480 A | 11/1993 | Naughton et al. |
| 5,278,432 A | 1/1994 | Ignatius et al. |
| 5,332,802 A | 7/1994 | Kelman et al. |
| 5,344,434 A | 9/1994 | Talmore |
| 5,358,503 A | 10/1994 | Bertwell et al. |
| 5,366,498 A | 11/1994 | Brannan et al. |
| 5,397,352 A | 3/1995 | Burres |
| 5,399,583 A | 3/1995 | Levy et al. |
| 5,421,816 A | 6/1995 | Lipkovker |
| 5,423,803 A | 6/1995 | Tankovich et al. |
| 5,425,728 A | 6/1995 | Tankovich |
| 5,445,146 A | 8/1995 | Bellinger |
| 5,445,608 A | 8/1995 | Chen et al. |
| 5,445,611 A | 8/1995 | Eppstein et al. |
| 5,445,634 A | 8/1995 | Keller |
| 5,460,939 A | 10/1995 | Hansbrough et al. |
| 5,474,528 A | 12/1995 | Meserol |
| 5,500,009 A | 3/1996 | Mendes et al. |
| 5,549,660 A | 8/1996 | Mendes et al. |
| 5,591,444 A | 1/1997 | Boss, Jr. |
| 5,616,140 A | 4/1997 | Prescott |
| 5,618,275 A | 4/1997 | Bock |
| 5,620,478 A | 4/1997 | Eckhouse |
| 5,634,711 A | 6/1997 | Kennedy et al. |
| 5,636,632 A | 6/1997 | Bommannan et al. |
| 5,643,334 A | 7/1997 | Eckhouse et al. |
| 5,647,866 A | 7/1997 | Zaias et al. |
| 5,658,323 A | 8/1997 | Miller |
| 5,660,461 A | 8/1997 | Ignatius et al. |
| 5,660,836 A | 8/1997 | Knowlton |
| 5,660,850 A | 8/1997 | Boss, Jr. |
| 5,665,053 A | 9/1997 | Jacobs |
| 5,665,372 A | 9/1997 | Boss, Jr. |
| 5,669,916 A | 9/1997 | Anderson |
| 5,683,380 A | 11/1997 | Eckhouse et al. |
| 5,686,112 A | 11/1997 | Liedtke |
| 5,698,866 A | 12/1997 | Doiron et al. |
| 5,707,401 A | 1/1998 | Talmore |
| 5,728,090 A | 3/1998 | Martin et al. |
| 5,752,948 A | 5/1998 | Tankovich et al. |
| 5,752,949 A | 5/1998 | Tankovich et al. |
| 5,755,752 A | 5/1998 | Segal |
| 5,766,214 A | 6/1998 | Mehl, Sr. et al. |
| 5,766,233 A | 6/1998 | Thiberg |
| 5,766,234 A | 6/1998 | Chen et al. |
| 5,773,609 A | 6/1998 | Robinson et al. |
| 5,800,478 A | 9/1998 | Chen et al. |
| 5,800,479 A | 9/1998 | Thiberg |
| 5,810,801 A | 9/1998 | Anderson et al. |
| 5,814,599 A | 9/1998 | Mitragotri et al. |
| 5,817,089 A | 10/1998 | Tankovich et al. |
| 5,829,448 A | 11/1998 | Fisher et al. |
| 5,836,999 A | 11/1998 | Eckhouse et al. |
| 5,837,224 A | 11/1998 | Voorhees et al. |
| 5,843,072 A | 12/1998 | Furumoto et al. |
| 5,871,480 A | 2/1999 | Tankovich |
| 5,904,659 A | 5/1999 | Duarte et al. |
| 5,913,883 A | 6/1999 | Alexander et al. |
| 5,932,240 A | 8/1999 | D'Angelo et al. |
| 5,947,921 A | 9/1999 | Johnson et al. |
| 5,951,596 A | 9/1999 | Bellinger |
| 5,954,675 A | 9/1999 | Dellagatta |
| 5,997,569 A | 12/1999 | Chen et al. |
| 6,024,717 A | 2/2000 | Ball et al. |
| 6,030,374 A | 2/2000 | McDaniel |
| 6,048,301 A | 4/2000 | Sabuda |
| 6,050,990 A | 4/2000 | Tankovich et al. |
| 6,063,108 A | 5/2000 | Salansky et al. |
| 6,074,382 A | 6/2000 | Asah et al. |
| 6,096,066 A | 8/2000 | Chen |
| 6,099,522 A | 8/2000 | Knopp |
| 6,110,106 A | 8/2000 | MacKinnon et al. |
| 6,113,559 A | 9/2000 | Klopotek |
| 6,120,497 A | 9/2000 | Anderson et al. |
| 6,143,287 A | 11/2000 | Ben-Hur et al. |
| 6,162,211 A | 12/2000 | Tankovich et al. |
| 6,171,332 B1 | 1/2001 | Whitehurst |
| 6,174,325 B1 | 1/2001 | Eckhouse |
| 6,183,773 B1 | 2/2001 | Anderson |
| 6,187,029 B1 | 2/2001 | Shapiro et al. |
| 6,190,315 B1 | 2/2001 | Kost et al. |
| 6,190,376 B1 | 2/2001 | Asah et al. |
| 6,214,034 B1 * | 4/2001 | Azar ............ 607/89 |
| 6,221,095 B1 | 4/2001 | Van Zuylen et al. |
| 6,223,071 B1 | 4/2001 | Lundahl et al. |
| 6,231,528 B1 | 5/2001 | Kaufman et al. |
| 6,238,424 B1 | 5/2001 | Thiberg |
| 6,251,127 B1 | 6/2001 | Biel |
| 6,267,779 B1 | 7/2001 | Gerdes |
| 6,283,956 B1 | 9/2001 | McDaniel |
| 6,302,874 B1 | 10/2001 | Zhang et al. |
| 6,312,450 B1 | 11/2001 | Yavitz et al. |
| 6,387,089 B1 | 5/2002 | Kreindel et al. |
| 6,413,268 B1 | 7/2002 | Hartman |
| 6,436,127 B1 | 8/2002 | Anderson et al. |
| 6,443,946 B2 | 9/2002 | Clement et al. |
| 6,459,087 B1 | 10/2002 | Kaas |
| 6,497,719 B2 | 12/2002 | Pearl et al. |
| 6,524,330 B1 * | 2/2003 | Khoobehi et al. ............ 607/89 |
| 6,602,275 B1 | 8/2003 | Sullivan |
| 6,629,971 B2 | 10/2003 | McDaniel |
| 6,645,230 B2 | 11/2003 | Whitehurst |
| 6,663,659 B2 * | 12/2003 | McDaniel ............ 607/88 |
| 6,676,655 B2 * | 1/2004 | McDaniel ............ 606/9 |
| 6,709,866 B2 | 3/2004 | Robertson et al. |
| 6,723,698 B2 | 4/2004 | Rueger et al. |
| 6,723,798 B1 | 4/2004 | Yoo |
| 6,746,444 B2 | 6/2004 | Key |
| 6,835,306 B2 | 12/2004 | Caldwell |
| 6,887,260 B1 * | 5/2005 | McDaniel ............ 607/88 |
| 6,936,044 B2 * | 8/2005 | McDaniel ............ 606/9 |
| 7,004,933 B2 | 2/2006 | McDaniel |
| 7,033,381 B1 | 4/2006 | Larsen |
| 7,115,120 B2 * | 10/2006 | Lin ............ 606/4 |
| 7,195,755 B2 | 3/2007 | Nguyen et al. |
| 7,201,765 B2 * | 4/2007 | McDaniel ............ 607/88 |
| 7,204,832 B2 | 4/2007 | Altshuler et al. |
| 7,258,695 B2 | 8/2007 | Carullo, Jr. et al. |
| 7,264,629 B2 | 9/2007 | Simkin et al. |
| 7,267,673 B2 | 9/2007 | Pilcher et al. |
| 7,309,335 B2 | 12/2007 | Altshuler et al. |
| 7,331,952 B2 | 2/2008 | Walneck et al. |
| 7,354,432 B2 | 4/2008 | Eells |
| 7,438,719 B2 | 10/2008 | Chung et al. |
| 7,470,270 B2 | 12/2008 | Azar et al. |
| 7,494,503 B2 | 2/2009 | McDaniel |
| 7,511,031 B2 | 3/2009 | Chen |
| 7,559,944 B2 | 7/2009 | Whang |
| 7,597,708 B2 | 10/2009 | Carullo, Jr. et al. |
| 7,618,414 B2 | 11/2009 | Connors et al. |
| 8,188,074 B2 | 5/2012 | Brown et al. |
| 8,328,794 B2 | 12/2012 | Altshuler et al. |
| 8,372,433 B2 | 2/2013 | Shinoka et al. |
| 2001/0013349 A1 | 8/2001 | Clement |
| 2001/0023363 A1 | 9/2001 | Harth et al. |
| 2001/0053347 A1 | 12/2001 | Varani et al. |
| 2002/0028185 A1 | 3/2002 | Fisher et al. |
| 2002/0029071 A1 | 3/2002 | Whitehurst |
| 2002/0123746 A1 | 9/2002 | McDaniel |
| 2002/0161357 A1 | 10/2002 | Anderson et al. |
| 2002/0173833 A1 | 11/2002 | Korman et al. |
| 2002/0183724 A1 | 12/2002 | Neev |
| 2002/0198575 A1 | 12/2002 | Sullivan |
| 2003/0004499 A1 | 1/2003 | McDaniel |
| 2003/0004556 A1 | 1/2003 | McDaniel |
| 2003/0060811 A1 | 3/2003 | McDaniel |
| 2003/0129154 A1 | 7/2003 | McDaniel |
| 2004/0039378 A1 | 2/2004 | Lin |
| 2004/0215293 A1 | 10/2004 | Eells et al. |
| 2005/0090877 A1 | 4/2005 | Harth et al. |
| 2006/0129209 A1 | 6/2006 | McDaniel |
| 2006/0184214 A1 | 8/2006 | McDaniel |

(56) References Cited

U.S. PATENT DOCUMENTS

| | | |
|---|---|---|
| 2006/0200213 A1 | 9/2006 | McDaniel |
| 2006/0212025 A1 | 9/2006 | McDaniel |
| 2006/0265030 A1 | 11/2006 | McDaniel |
| 2007/0128576 A1 | 6/2007 | Boutoussov |
| 2007/0129613 A1 | 6/2007 | Rochester et al. |
| 2007/0129711 A1 | 6/2007 | Altshuler |
| 2007/0129776 A1 | 6/2007 | Robins et al. |
| 2007/0129778 A1 | 6/2007 | Dougal |
| 2007/0149900 A1 | 6/2007 | Lin |
| 2007/0149901 A1 | 6/2007 | Gordon et al. |
| 2007/0150030 A1 | 6/2007 | Pearl |
| 2007/0156208 A1 | 7/2007 | Havell |
| 2007/0167999 A1 | 7/2007 | Breden et al. |
| 2007/0168000 A1 | 7/2007 | Happawana |
| 2007/0173912 A1 | 7/2007 | Amornsiripanitch |
| 2007/0173913 A1 | 7/2007 | Anderson et al. |
| 2007/0179482 A1 | 8/2007 | Anderson |
| 2007/0179574 A1 | 8/2007 | Elliott |
| 2007/0198004 A1 | 8/2007 | Altshuler et al. |
| 2007/0208326 A1 | 9/2007 | Connors |
| 2007/0208328 A1 | 9/2007 | Boutoussov |
| 2007/0208395 A1 | 9/2007 | Leclerc |
| 2007/0208396 A1 | 9/2007 | Whatcott |
| 2007/0208400 A1 | 9/2007 | Nadkarni |
| 2007/0213696 A1 | 9/2007 | Altshuler et al. |
| 2007/0219604 A1 | 9/2007 | Yaroslavsky et al. |
| 2007/0219605 A1 | 9/2007 | Yaroslavsky et al. |
| 2007/0231255 A1 | 10/2007 | Barolet et al. |
| 2007/0239142 A1 | 10/2007 | Altshuler et al. |
| 2007/0239147 A1 | 10/2007 | Manstein et al. |
| 2007/0299486 A1 | 12/2007 | Hoenig et al. |
| 2008/0009923 A1 | 1/2008 | Paithankar |
| 2008/0015555 A1 | 1/2008 | Manstein et al. |
| 2008/0021528 A1 | 1/2008 | Carullo |
| 2008/0031833 A1 | 2/2008 | Oblong |
| 2008/0031924 A1 | 2/2008 | Gilson |
| 2008/0033516 A1 | 2/2008 | Altshuler et al. |
| 2008/0035864 A1 | 2/2008 | Fiset |
| 2008/0039906 A1 | 2/2008 | Huang et al. |
| 2008/0045933 A1 | 2/2008 | Perl |
| 2008/0051856 A1 | 2/2008 | Vizethum |
| 2008/0058783 A1 | 3/2008 | Altshuler et al. |
| 2008/0058784 A1 | 3/2008 | Manstein et al. |
| 2008/0058905 A1 | 3/2008 | Wagner |
| 2008/0065056 A1 | 3/2008 | Powell et al. |
| 2008/0065175 A1 | 3/2008 | Redmond |
| 2008/0077199 A1 | 3/2008 | Shefl |
| 2008/0082148 A1 | 4/2008 | Bernstein |
| 2008/0082149 A1 | 4/2008 | Bernstein |
| 2008/0091179 A1 | 4/2008 | Durkin et al. |
| 2008/0097278 A1 | 4/2008 | Cole |
| 2008/0097419 A1 | 4/2008 | MacFarland |
| 2008/0103560 A1 | 5/2008 | Powell et al. |
| 2008/0106896 A1 | 5/2008 | Liu et al. |
| 2008/0139901 A1 | 6/2008 | Altshuler et al. |
| 2008/0147054 A1 | 6/2008 | Altshuler et al. |
| 2008/0147148 A1 | 6/2008 | Baldacchini |
| 2008/0172112 A1 | 7/2008 | Gourgouliatos et al. |
| 2008/0172114 A1 | 7/2008 | Gourgouliatos et al. |
| 2008/0177255 A1 | 7/2008 | Bernardini |
| 2008/0183161 A1 | 7/2008 | Walneck et al. |
| 2008/0200908 A1 | 8/2008 | Domankevitz |
| 2008/0203280 A1 | 8/2008 | Rizoiu |
| 2008/0208294 A1 | 8/2008 | Pierce |
| 2008/0208295 A1 | 8/2008 | Cumbie |
| 2008/0234669 A1 | 9/2008 | Kauvar |
| 2008/0234786 A1 | 9/2008 | Cumbie |
| 2008/0255640 A1 | 10/2008 | Kipp |
| 2008/0262394 A1 | 10/2008 | Pryor |
| 2008/0262482 A1 | 10/2008 | Hantash et al. |
| 2008/0262576 A1 | 10/2008 | Creamer |
| 2008/0267814 A1 | 10/2008 | Bornstein |
| 2008/0269732 A1 | 10/2008 | Pyun |
| 2008/0269733 A1 | 10/2008 | Anderson |
| 2008/0269844 A1 | 10/2008 | Logslett |
| 2008/0269848 A1 | 10/2008 | Birmingham et al. |
| 2008/0269849 A1 | 10/2008 | Lewis |
| 2008/0275532 A1 | 11/2008 | Yamazaki |
| 2008/0281307 A1 | 11/2008 | Donahue |
| 2008/0294151 A1 | 11/2008 | Whitaker et al. |
| 2008/0294152 A1 | 11/2008 | Altshuler et al. |
| 2009/0012508 A1 | 1/2009 | Dougal |
| 2009/0018621 A1 | 1/2009 | Vogler et al. |
| 2009/0018622 A1 | 1/2009 | Asvadi et al. |
| 2009/0024116 A1 | 1/2009 | Mulhauser et al. |
| 2009/0043293 A1 | 2/2009 | Pankratov et al. |
| 2009/0062889 A1 | 3/2009 | Kiessl |
| 2009/0082836 A1 | 3/2009 | Schell |
| 2009/0088824 A1 | 4/2009 | Baird et al. |
| 2009/0105791 A1 | 4/2009 | McGinnis et al. |
| 2009/0112192 A1 | 4/2009 | Barolet |
| 2009/0112294 A1 | 4/2009 | Huang |
| 2009/0149843 A1 | 6/2009 | Smits et al. |
| 2009/0177190 A1 | 7/2009 | Lee |
| 2009/0177253 A1 | 7/2009 | Darm et al. |
| 2009/0177256 A1 | 7/2009 | Ripper et al. |
| 2009/0187169 A1 | 7/2009 | Durkin et al. |
| 2009/0198173 A1 | 8/2009 | Samuel et al. |
| 2009/0227996 A1 | 9/2009 | Powell et al. |
| 2009/0234253 A1 | 9/2009 | Vandenbelt |
| 2009/0234337 A1 | 9/2009 | Ely et al. |
| 2009/0234341 A1 | 9/2009 | Roth |
| 2009/0234342 A1 | 9/2009 | Ely et al. |
| 2009/0247932 A1 | 10/2009 | Barolet |
| 2009/0251057 A1 | 10/2009 | Son et al. |
| 2009/0254154 A1 | 10/2009 | De Taboada |
| 2009/0254156 A1 | 10/2009 | Powell et al. |
| 2009/0270845 A1 | 10/2009 | Birmingham et al. |
| 2009/0270946 A1 | 10/2009 | Spivak |
| 2009/0270953 A1 | 10/2009 | Ecker |
| 2010/0121254 A1 | 5/2010 | Mcdaniel |
| 2010/0256550 A1 | 10/2010 | Mcdaniel |

FOREIGN PATENT DOCUMENTS

| | | |
|---|---|---|
| EP | 1878466 A1 | 1/2008 |
| EP | 1916016 A1 | 4/2008 |
| EP | 1920798 A1 | 5/2008 |
| EP | 1935452 A1 | 6/2008 |
| EP | 1958662 A1 | 8/2008 |
| EP | 1964590 A1 | 9/2008 |
| EP | 2044901 | 4/2009 |
| EP | 2044973 | 4/2009 |
| EP | 2044974 | 4/2009 |
| EP | 2055349 | 5/2009 |
| EP | 2106198 | 9/2009 |
| EP | 2106780 | 10/2009 |
| EP | 2106824 | 10/2009 |
| EP | 2110159 | 10/2009 |
| GB | 2-262-043 A | 6/1993 |
| GB | 2-360-461 A | 9/2001 |
| GB | 2360461 | 9/2001 |
| GB | 2360641 | 9/2001 |
| JP | H01-136668 | 5/1989 |
| JP | 07-016304 A | 1/1995 |
| JP | H07-100219 | 4/1995 |
| JP | H07505614 | 6/1995 |
| JP | H08308943 | 11/1996 |
| JP | H09-508031 | 8/1997 |
| JP | H10-503109 | 3/1998 |
| JP | 2000-202044 | 7/2000 |
| JP | 2000-202044 A | 7/2000 |
| JP | 2002-522110 | 7/2002 |
| JP | 2002535101 | 10/2002 |
| JP | 2005503388 | 2/2005 |
| JP | 2010047590 | 3/2010 |
| RU | SU1724269 | 4/1992 |
| WO | 93/09847 | 5/1993 |
| WO | 93/09874 | 5/1993 |
| WO | 93/21842 | 11/1993 |
| WO | 95/19809 | 7/1995 |
| WO | 96/11723 | 4/1996 |
| WO | 96/24406 | 8/1996 |
| WO | 97/46279 | 12/1997 |

(56) References Cited

FOREIGN PATENT DOCUMENTS

| | | |
|---|---|---|
| WO | 98/14453 | 4/1998 |
| WO | 98/50034 | 11/1998 |
| WO | WO-99/04628 | 2/1999 |
| WO | 99/19024 | 4/1999 |
| WO | 99/20336 | 4/1999 |
| WO | WO-99/39763 A1 | 8/1999 |
| WO | 00/02491 | 1/2000 |
| WO | 00/02497 | 1/2000 |
| WO | WO 00/002491 | 1/2000 |
| WO | 00/07514 | 2/2000 |
| WO | 00/32121 | 6/2000 |
| WO | 00/40266 | 7/2000 |
| WO | WO 00/40266 A | 7/2000 |
| WO | 00/44441 | 8/2000 |
| WO | 00/57804 | 10/2000 |
| WO | 00/74782 | 12/2000 |
| WO | 01/14012 | 3/2001 |
| WO | 01/40232 | 6/2001 |
| WO | WO-01/40232 | 6/2001 |
| WO | 02/057811 | 7/2002 |
| WO | 03/001984 | 1/2003 |
| WO | 03/002187 | 1/2003 |
| WO | 03/005883 | 1/2003 |
| WO | 03/017824 | 3/2003 |
| WO | 03/086215 | 10/2003 |
| WO | WO 03/086215 | 10/2003 |
| WO | 2004/075985 | 9/2004 |
| WO | 2004/092335 | 10/2004 |
| WO | 2005/011606 | 2/2005 |
| WO | WO-2005/077452 A1 | 8/2005 |
| WO | 2005/089039 | 9/2005 |
| WO | 2005/096766 | 10/2005 |
| WO | 2005/115263 A1 | 12/2005 |
| WO | 2006/013390 | 2/2006 |
| WO | 2006/013390 A1 | 2/2006 |
| WO | 2006/099413 A2 | 9/2006 |
| WO | 2006/107387 A2 | 10/2006 |
| WO | 2006/116141 A1 | 11/2006 |
| WO | 2006/125231 A2 | 11/2006 |
| WO | 2007/013110 A1 | 2/2007 |
| WO | 2007/036002 A1 | 4/2007 |
| WO | 2007/044840 A2 | 4/2007 |
| WO | 2007/066657 A1 | 6/2007 |
| WO | 2007/087374 A2 | 8/2007 |
| WO | 2007/092349 | 8/2007 |
| WO | 2007/096344 A1 | 8/2007 |
| WO | 2007/103132 A2 | 9/2007 |
| WO | 2007/106339 A2 | 9/2007 |
| WO | 2007/106856 A2 | 9/2007 |
| WO | 2007/118303 A2 | 10/2007 |
| WO | 2007/125336 A1 | 11/2007 |
| WO | 2007/126339 A1 | 11/2007 |
| WO | 2007/146101 A2 | 12/2007 |
| WO | 2008/008971 A1 | 1/2008 |
| WO | 2008/012519 A1 | 1/2008 |
| WO | 2008/017975 A1 | 2/2008 |
| WO | 98/11723 | 3/2008 |
| WO | 2008/078750 A1 | 7/2008 |
| WO | 2008/084764 A1 | 7/2008 |
| WO | 2008/097062 A1 | 8/2008 |
| WO | 2008/128175 A1 | 10/2008 |
| WO | 2008/129740 A1 | 10/2008 |
| WO | 2008/129741 A1 | 10/2008 |
| WO | 2008/131079 A1 | 10/2008 |
| WO | 2008/131343 A1 | 10/2008 |
| WO | 2008/135548 A1 | 11/2008 |
| WO | 2008/135658 A2 | 11/2008 |
| WO | 2008/137489 A1 | 11/2008 |
| WO | 2008/146219 A1 | 12/2008 |
| WO | 2008/146220 A2 | 12/2008 |
| WO | 2008/146255 A2 | 12/2008 |
| WO | 2009/003295 A1 | 1/2009 |
| WO | 2009/008967 | 1/2009 |
| WO | 2009/014034 | 1/2009 |
| WO | 2009/016598 | 2/2009 |
| WO | 2009/016963 | 2/2009 |
| WO | 2009/023568 | 2/2009 |
| WO | 2009/023968 | 2/2009 |
| WO | 2009/038720 | 3/2009 |
| WO | 2009/056838 | 5/2009 |
| WO | 2009/059270 | 5/2009 |
| WO | 2009/064034 | 5/2009 |
| WO | 2009/089177 | 7/2009 |
| WO | 2009/107095 | 9/2009 |
| WO | 2009/117323 | 9/2009 |
| WO | 2009/118617 | 10/2009 |
| WO | 2009/121158 | 10/2009 |
| WO | 2009/123196 | 10/2009 |
| WO | 2009/125338 | 10/2009 |
| WO | 2009/132585 | 11/2009 |
| WO | 2009/137612 | 11/2009 |
| ZA | 97/07751 | 8/1997 |

OTHER PUBLICATIONS

"Hair Regrowth with Cell Wave Therapy," A Guide to Treatement 1996.

"Laser Hair Care," Model 4000, 1996, www.laserhaircare.com/laserhair/background.html.

A. Doukas et al. (1996) "Physical Characteristics and Biological Effects of Laser-Induced Stress Waves," *Ultrasound in Med. & Biol.* 22(2), pp. 151-164.

A. Finlay et al. (1982) "A Fluorescence Photographic Photometric Technique to Assess Stratum Corneum Turnover Rate and Barrier Function Vivo," *British Journal of Dermatology* 107, pp. 35-42.

Abergel et al., (1987) "Biostimulation of Wound Healing by Lasers: Experimental Approaches in Animal Models and in Fibroblast Cultures" *J. Dermatol. Surg. Oncol.* 13(2), pp. 127-133.

Alain Rolland et al. (1993) "Site-Specific Drug Delivery to Pilosebaceous Structures Using Polymeric Microspheres," *Pharmaceutical Research* 10(12), pp. 1738-1744.

B. Krammer et al. (Feb. 1993) "Photodynamic Effects on the Nuclear Envelope of Human Skin Fibroblasts," *Journal of Photochem Photobiol. B*: Biol. 17(2), pp. 109-114.

Bommannan et al. (1992) "Sonophoresis I. The Use of High-Frequency Ultrasound to Enhance Transdermal Drug Delivery," *Pharmaceutical Research* 9(4), pp. 559-564.

Bommannan et al. (1992) "Sonophoresis II. Examination of the Mechanisms of Ultrasound-Enhanced Transdermal Drug Delivery," Pharmaceutical Research 9(8), pp. 1043-1047.

Brigette Illel et al. (1991) "Follicles Play an Important Role in Percutaneous Absorption," *Journal of Pharmaceutical Sciences* 80(5).

Burgess "Researchers Identify Key to Phototropism," *Biophotonics International*, Nov./Dec. 1999, pp. 22-23.

C. Green et al. (1988) "311 nm UVB Phototherapy: an Effective Treatment for Psoriasis," Br J Dermatol. 119, pp. 694-696.

Castro (Sep. 1983) "Effects of the Nd:YAG Laser on DNA SYnthesis and Collagen Production in Human Skin Fibroblast Cultures" *Annals of Plastic Surgery* 11, pp. 3.

Charlotte Phillips et al. (1992) "Ascorbic Acid and Transforming Growth Factor-B1 Increase Collagen Biosynthesis via Different Mechanisms: Coordinate Regulation of Proa1(I) and Proa1(III) Collagens," *Archives of Biochemistry and Biophysics* 295(2), pp. 397-403.

Charlotte Phillips et al. (1994) "Effects of Ascorbic Acid on Proliferation and Collagen Synthesis in Relation to the Donor Age of Human Dermal Fibroblasts," *The Journal of Investigative Dermatology* 103(2).

Chinese Office Action dated Oct. 14, 2005, directed to counterpart Chinese Application No. 028247698.

Chukuka S. Enwemeka (Dec. 1989) "The Effects of Therapeutic Ultrasound on Tendon Healing," *Am. J. Phys. Med. & Rehabil.* 68(6), pp. 283-287.

D. F. Webster et al. "The Role of Cavitation in the In Vitro Stimulation of Protein Synthesis in Human Fibroblasts by Ultrasound," *Ultrasound in Med & Biol.* 4, pp. 343-351.

(56) References Cited

OTHER PUBLICATIONS

D. F. Webster et al. (1980) "The Role of Ultrasound-Induced Cavitation in the 'In Vitro' Stimulation of Collagen Synthesis in Human Fibroblasts," *Ultrasonics*, pp. 33-37.
D. J. Castro et al. (Dec. 1987) "Biostimulative Effects of Nd: YAG Q-Switch Dye on Normal Human Fibroblast Cultures: Study of a New Chemosensitizing Agent for the Nd:YAG Laser," *Laryngoscope*, 97(12), pp. 1454-1459.
Dan Roden, MD (1997) "Electrophysiology, Pacing and Arrhythmia," *Clin Cardiol* 20, pp. 285-290.
David Draper et al. (1995) "Temperature Changes in Deep Muscles of Humans During Ice and Ultrasound Therapies: an In Vivo Study," *JOSPT* 12(3).
Des Travers, Australasian Post, Feb. 11, 1989.
Doan et al, (1999) "In Vitro Effects of Therapeutic Ultrasound on Cell Proliferation, Protein Synthesis, and Cytokine Production by Human Fibroblasts, Osteoblasts, and Monocytes" *J. Oral Maxillofac Surg.* 57, pp. 409-419.
Douglas Darr et al. (1993) "Ascorbic Acid and Collagen Synthesis: Rethinking a Role for Lipid Peroxidation," *Archives of Biochemistry and Biophysics* 307(2), pp. 331-335.
Edwards, (May 2001) "Keeping Up with the LEDs," *Photonics Spectra*.
Ethel Tur et al. (1991) "Percutaneous Penetration of Methyl Nicotinate at Three Anatomic Sites: Evidence for an Appendagael Contribution to Transport?" *Skin Pharmacol* 4, pp. 230-234.
European Search Report dated Sep. 16, 2005, directed to counterpart EP Application No. 02761449.4.
F. Heuber et al. (1994) "Percutaneous Absorption of Estradiol and Progesterone in Normal and Appendage-Free Skin of the Hairless Rat: Lack of Importance of Nutritional Blood Flow," *Skin Pharmacol* 7, pp. 245-256.
G. Kesave Reddy et al. (1998) "Laser Photostimulation of Collagen Production in Healing Rabbit Achilles Tendons," *Lasers in Surgery and Medicine* 22, pp. 281-287.
G. Morrone et al. (Jul. 1998) "In Vitro Experimental Research of Rabbit Condrocytes Biostimulation with Diode Laser Ga—Al—As: a Preliminary Study," Artif Cells Blood Substit Immobil Biotechnol. 26(4), pp. 437-439.
G. Nicolau et al. (1987) "Deposition of Viprostol (a Synthetic PGE2 Vasodilator) in the Skin Following Topical Administration to Laboratory Animals," *Xenobiotica* 17(9), pp. 1113-1120.
Giamundo, (May 2001) "A Little Enlightenment," *Photonics Spectra*.
Goldman, (Oct. 1999) "FotoFacial is a Pulsed Light Patient Pleaser" *Skin & Allergy News*.
Gopinathan K. Menon et al. (1991) "Ultrasound Localization of Calcium in Psoriatic and Normal Human Epidermis," *Arch Dermatol* 127.
Gopinathan K. Menon et al. (1994) "High-Frequency Sonophoresis: Permeation Pathways and Structural Basis for Enhanced Permeability," *Skin Pharmacol.* 7, pp. 130-139.
Gupta et al., (1998) "The Use of Low Energy Photon Therapy (LEPT) in Venous Leg Ulcers: A Double-Blind, Placebo-Controlled Study" *Dermatol. Surg.* 24, pp. 1383-1386.
Gupta, A.K. et al. (1997) "The Use of Low-Energy Therapy in the Treatment of Leg Ulcers—A Preliminary STudy," *Journal of Dermatological Treatment* 8(2), pp. 103-108.
H. Van Weelden et al. (1990) "Comparison of Narrow band UV-B Phototherapy and PUVA Photochemotherapy in the Treatment of Psoriasis," Acta Dermatol Venereol (Stockh) 70, pp. 212-215.
Hans Schaefer et al. (1996) "Skin Barrier Principles of Percutaneous Absorption," pp. 153 and 175.
Heather A. Benson et al. (1991) "Influence of Ultrasound on the Percutaneous Absorption of Nicotinate Esters," *Pharmaceutical Research* 8(2), pp. 204-209.
Heather A. E. Benson et al. (1988) "Transmission of Ultrasound Energy Through Topical Pharmaceutical Products," *Physiotherapy* 74(11), pp. 587-589.
Huxiong Cheng et al. (1995) "Chemical Generation of Acoustic Waves: A Giant Photoacoustic Effect," *Science* 270.
J. Kao et al. (1988) "In Vitro Percutaneous Absorption in Mouse Skin: Influence of Skin Appendages," *Toxicology and Applied Pharmacology* 94, pp. 93-103.
J. Pospisilova et al. (1977) "Ultrasonic Effect on Collagen Synthesis and Deposition in Differently Localized Experiemental Granulomas," *Acta Chirurgiae Plasticae* 19, pp. 148-156.
M. Hrnjak et al. (Nov. 1995) "Stimulatory Effect of Low-Power Density He—Ne Radiation on Human Fibroblast In Vitro," *Vojnosanit Pregl.* 52(6), pp. 539-546.
M. Pogrel et al. (1997) "Efects of Low-Energy Gallium—Aluminum—Arsenide Laser Irradiation on Cultured Fibroblasts and Keratincytes," *Lasers in Surgery and Medicine* 20, pp. 426-432.
McDaniel, (May 2001) "Nonablative Skin Rejuvenation-The Wave of Future" *Cosmetic Surgery Times*.
McDaniel, D. H. et al. (1996) "Treatment of Stretch Marks With the 585 Nm Flashlamp-Pumped Pulsed Dye Laser," *Dermatological* 22(4), pp. 332-337.
Michelle Pronsati (Mar. 1992) "Uniformity Needed in Therapeutic Use of Ultrasound," *Advance for Physical Therapists*.
Miklos M. Breuer (Jun. 1998) "Ultrasonic Radiation for Hair Treatments," *Cosmetics & Toiletries* 113, pp. 67-75.
N. Weiner et al. (1994) "Liposomes: A Novel Topical Delivery System for Pharmaceutical and Cosmetic Applications," *Journal of Drug Targeting* 2, pp. 405-410.
Nancy Gann (1991) "Ultrasound: Current Concepts," *Electrotherapy* 11(4).
Nancy N. Byl et al. (Jul. 1992) "Low-Dose Ultrasound Effects on Wound Healing: A Controlled Study with Yucatan Pigs," *Arch. Phys. Med. Rehabil.* 73, pp. 656-664.
P. Asawanonda et al. (May 2000) "308-nm Excimer Laser for the Treatment of Psoriasis," *Arch Dermtol.* 136, pp. 619-624.
P. Lehmann et al. (1991) "Effects of Ultraviolet A and B on the Skin Barrier: a Functional, Electron Microscopic and Lipid Biochemical Study," *Photodermatol Photoimmunol Photomed.* 8, pp. 129-134.
P. Morganti et al. (1997) "Enhancing the Glycolic Acid Efficacy by Piezoelectric Vibrations," *J. Appl. Cosmotol.* vol. 15, pp. 147-159.
Parminder Singh et al. (1993) "Iontophoretic Transdermal Delivery of Salicylic Acid and Lidocaine to Local Subcutaneous Structures," *Journal of Pharmaceutical Sciences* 82(2).
Patrick G. De Deyne et al. (Jul. 1995) "In Vitro Effects of Therapeutic Ultrasound on the Nucleus of Human Fibroblasts," *Physical Therapy* 75(7), pp. 629-634.
Polo, et al., (1999) "Role of Ground and Excited Singlet State Ozygen in the Red Light-Induced Stimulation of *Escherichia coli* Cell Growth" *Biochemical and Biophysical Research Communications* 257, pp. 753-758.
Pontinen et al. (1996) The Effect of Hair Lasers on Skin Blood Flow, Acupuncture & Electrotherapeutic Res. Int. J. vol. 21, pp. 105-118.
R. F. Lyons et al. (1987) "Biostimulation of Wound Healing in Vivo by a Helium—Neon Laser," *Ann Plast. Surg.* 18(1), pp. 47-50.
Richard Brucks et al. (1989) "The Effect of Ultrasound on the In Vitro Penetration of Ibuprofen Through Human Epidermis," Pharmaceutical Research 6(8), pp. 697-701.
Robert Scheuplein et al. (1971) "Permeability of the Skin," *Physiological Review* 51(4).
Ronald Wester et al. (1980) "Variations in Percutaneous Absorption of Testosterone in the Rhesus Monkey Due to Anatomic Site of Applications and Frequency of Application," Arch Dermatol Res. 267, pp. 229-235.
S. Borelli (1955) "Chlorophyll in the Treatment 1-27 of Acne Vulgaris," Dermatologie, Venerologie, and Verwandte Gebiete 6(7), pp. 320-324.
S. Mordon et al. (1997) "Selective Laser Photocoagulation of Blood Vessels in a Hamater Skin Flap Model Using a Specific ICG Formulation," *Lasers in Surg. & Med.* 21, pp. 365-373.
S. Mordon et al. (1997) "Thermal Damage Assessment of Blood Vessels in a Hamster Skin Flap Model by Fluorescence Measurement of a Liposome-Dye System," *Lasers in Surg & Med.* 20, pp. 131-141.
Samir Mitragotri et al. (1995) "A Mechanistic Study of Ultrasonically-Enhanced Transdermal Drug Delivery," *Journal of Pharmaceutical Sciences* 84(6), pp. 697-706.

(56) References Cited

OTHER PUBLICATIONS

Samir Mitragotri et al. (Aug. 1995) "Ultrasound-Mediated Transdermal Protein Delivery," *Science* 269, pp. 850-853.
Saran Kumar et al. (1992) "Studies of In Vitro Skin Permeation and Retention of a Leukotriene Antagonist from Topical Vehicles with a Hairless Guinea Pig Model," *Journal of Pharmaceutical Sciences* 81(7).
Schindl et al., (Sep. 2000) "Low-Intensity Laser Therapy : A Review" Journal of Investigative Medicine, 48(5).
Shalita et al., (2001) "Acne PhotoClearing (APC) Using a Novel, Hight-Intensity, Enhanced, Narrow-Band, Blue Light Source" *Clinical Application Notes* 9(1).
Sheldon Pinnell (1985) "Regulation of Collagen Biosynthesis of Ascorbic Acid: A Review," The Yale Journal of Biology and Medicine 58, pp. 553-559.
Van Breugel et al. (1992) "Power Density and Exposure Time of He—Ne Laser Irradiation are More Important Than Total Energy Dose in Photo-Biomodulation of Human Fibroblasts in Vitro" *Lasers in Surgery and Medicine* 12, pp. 528-537.
W. Westerhof et al. (1997) "Treatment of Vitiligo with UV-B Radiation vs. Topical Psoralen Plus UV-A," *Arch. Dermatol.* 133, pp. 1525-1528.
Parrish et al. (1981). "Action Spectrum for Phototherapy of Psoriasis," Journal of Investigative Dermatology, 76(5):359-362.
"Chlorophyll," from Wikipedia located at <http://de.wikipedia.org/wiki/Chlorophyll, visited on Jul. 18, 2007. (5 pages).
"Porphin," from Wikipedia located at <en.wikipedia.org/wiki/Porphine, visited on Jul. 18, 2007. (2 pages).
European Written Opinion dated Jul. 31, 2007, directed to counterpart EP Application No. 02761449.4.
International Search Report and Written Opinion mailed May 22, 2008, directed to counterpart international application No. PCT/US2007/02958; 10 pages.
European Office Action directed at application No. 02761449.4 mailed on Jul. 21, 2008; 8 pages.
Preliminary Amendment filed Feb. 15, 2001 for U.S. Appl. No. 09/819,083.
Non-Final Rejection dated Feb. 19, 2003 for U.S. Appl. No. 09/819,083.
Amendment to Non-Final Rejection dated Feb. 19, 2003 for U.S. Appl. No. 09/819,083.
Preliminary Amendment filed May 2, 2005 for U.S. Appl. No. 11/119,378.
Non-Final Rejection dated Jun. 5, 2006 for U.S. Appl. No. 11/119,378.
Amendment to Non-Final Rejection dated Jun. 5, 2006 for U.S. Appl. No. 11/119,378.
Preliminary Amendment filed Aug. 29, 2005 for U.S. Appl. No. 11/212,916.
Non-Final Rejection dated Sep. 25, 2007 for U.S. Appl. No. 11/212,916.
Amendment to Non-Final Rejection dated Sep. 25, 2007 for U.S. Appl. No. 11/212,916.
Final Rejection dated Mar. 25, 2008 for U.S. Appl. No. 11/212,916.
Non-Final Rejection dated Jun. 19, 2008 for U.S. Appl. No. 11/332,517.
Non-Final Rejection dated Dec. 19, 2002 for U.S. Appl. No. 09/986,367.
Amendment to Non-Final Rejection dated Dec. 19, 2002 for U.S. Appl. No. 09/986,367.
Final Rejection dated Aug. 12, 2003 for U.S. Appl. No. 09/986,367.
Amendment to Final Office Action dated Aug. 12, 2003 for U.S. Appl. No. 09/986,367.
Advisory Action dated Mar. 8, 2004 for U.S. Appl. No. 09/986,367.
Non-Final Rejection dated Sep. 22, 2004 for U.S. Appl. No. 09/986,367.
Amendment to Non-Final Rejection dated Sep. 22, 2004 for U.S. Appl. No. 09/986,367.
Non-Final Rejection dated Jun. 26, 2008 for U.S. Appl. No. 11/366,811.
Amendment to Non-Final Oa dated Sep. 22, 2009 for U.S. Appl. No. 11/116,434.
Final Rejection dated Sep. 15, 2010 for U.S. Appl. No. 11/116,434.
Response to Final Office Action dated Sep. 15, 2010 for U.S. Appl. No. 11/116,434.
Advisory Action dated Dec. 22, 2010 for U.S. Appl. No. 11/116,434.
Appeal Brief dated Aug. 15, 2011 for U.S. Appl. No. 11/116,434.
U.S. Office Action dated May 10, 2011 for U.S. Appl. No. 12/550,749.
Response to Office Action dated May 10, 2011 for U.S. Appl. No. 12/550,749.
Final Office Action dated Jan. 18, 2012 for U.S. Appl. No. 12/550,749.
Response to Final Office Action dated Jan. 18, 2012 for U.S. Appl. No. 12/550,749.
U.S. Office Action dated May 11, 2011 for U.S. Appl. No. 12/550,799.
Response to Office Action dated May 11, 2011 for U.S. Appl. No. 12/550,799.
Final Office Action dated Dec. 3, 2012 for U.S. Appl. No. 12/550,799.
U.S. Office Action dated Mar. 30, 2011 for U.S. Appl. No. 12/550,464.
Response to Office Action dated Mar. 30, 2011 for U.S. Appl. No. 12/550,464
U.S. Office Action dated Oct. 28, 2011 for U.S. Appl. No. 12/550,464.
Response to Office Action dated Oct. 28, 2011 for U.S. Appl. No. 12/550,464.
Final Office Action dated May 29, 2012 for U.S. Appl. No. 12/550,464.
Response to Final Office Action dated May 29, 2012 for U.S. Appl. No. 12/550,464.
U.S. Office Action dated May 25, 2011 for U.S. Appl. No. 12/753,207.
Response to Office Action dated May 25, 2011 for U.S. Appl. No. 12/753,207.
Result of Consultation by Telephone with Applicant/Representative dated Aug. 28, 2008 for European Patent Application No. 027614494-1216.
Decision to Refuse a European Application dated Mar. 31, 2009 for European Patent Application No. 02761449.4-1216.
Official Action dated May 13, 2008 for Israeli Patent Application No. 160505.
Response to Official Action dated May 13, 2008 for Israeli Patent Application No. 160505.
Office Action dated May 16, 2010 for Israeli Patent Application No. 160505.
Response to Office Action dated May 16, 2010 for Israeli Patent Application No. 160505.
Office Action dated Mar. 1, 2007 for Indian Patent Application No. 00332/KOLNP/2004.
Response to Office Action dated Mar. 1, 2007 for Indian Patent Application No. 00332/KOLNP/2004.
Office Action dated Nov. 10, 2008 for Korean Patent Application No. 7002677/2004.
Decision of Rejection dated Dec. 1, 2008 for Japanese Patent Application No. 2003-522355.
Office Action dated Feb. 22, 2012 for Japanese Patent Application No. 2009-236857.
Response to Office Action dated Feb. 22, 2012 for Japanese Patent Application No. 2009-236857.
Office Action dated Sep. 12, 2012 for Japanese Patent Application No. 2009-236857.
Response to Office Action dated Sep. 12, 2012 for Japanese Patent Application No. 2009-236857.
Official Letter dated Sep. 3, 2007 for Mexican Patent Application No. 2004/001710.
Reply to Official Action dated Sep. 3, 2007 for Mexican Patent Application No. 2004/001710.
2nd Official Action dated Sep. 19, 2008 for Mexican Patent Application No. 2004/001710.

(56) References Cited

OTHER PUBLICATIONS

3rd Official Action dated Dec. 8, 2010 for Mexican Patent Application No. 2004/001710.
Response to 3rd Official Action dated Dec. 8, 2010 for Mexican Patent Application No. 2004/001710.
Examination Report dated Apr. 28, 2005 for New Zealand Patent Application No. 531491.
First Statement of Proposed Amendments dated Dec. 21, 2005 for Australian Patent Application No. 2002357695.
Official Report dated Jun. 28, 2007 for Australian Patent Application No. 2002357695.
Response to Official Report dated Jun. 28, 2007 for Australian Patent Application No. 2002357695.
Official Report dated Dec. 19, 2007 for Australian Patent Application No. 2002357695.
Office Action dated Aug. 9, 2006 for Canadian Patent Application No. 2465906.
Response to Office Action dated Aug. 9, 2006 for Canadian Patent Application No. 2465906.
Office Action dated Mar. 27, 2007 for Canadian Patent Application No. 2465906.
Response and Amendment to Office Action dated Mar. 27, 2007 for Canadian Patent Application No. 2465906.
Office Action dated Nov. 23, 2007 for Canadian Patent Application No. 2465906.
Response to Office Action dated Nov. 23, 2007 for Canadian Patent Application 2465906.
Office Action dated Oct. 5, 2010 for Canadian Patent Application No. 2465906.
Response to Office Action dated Oct. 5, 2010 for Canadian Patent Application No. 2465906.
Office Action dated Jun. 30, 2011 for Canadian Patent Application No. 2465906.
Response to Office Action dated Jun. 30, 2011 for Canadian Patent Application No. 2465906.
Office Action dated Mar. 3, 2010 Canadian Patent Application 2465906.
Response to Office Action dated Mar. 3, 2010 for Canadian Patent Application No. 2465906.
Office Action dated Oct. 14, 2005 for Chinese Patent Application No. 028247698.
Response to Office Action dated Oct. 14, 2005 for Chinese Patent Application No. 028247698.
Second Office Action dated Apr. 11, 2008 for Chinese Patent Application No. 028247698.
Response to Second Office Action dated Apr. 11, 2008 for Chinese Patent Application No. 028247698.
Third Office Action dated Aug. 15, 2008 for Chinese Patent Application No. 028247698.
Office Action dated Sep. 11, 2006 for European Patent Application No. 02792232.7.
Response to Office Action dated Sep. 11, 2006 for European Patent Application No. 02792232.7.
Office Action dated Jul. 2, 2007 for European Patent Application No. 02792232.7.
Heikkila, H., Stubb, S., & Kiistala, U. (1996). "Nail growth measurement employing nail indentation—an experimental follow-up study of nail growth in situ" Clinical and Experimental Dermatology, 21(2). pp. 96-99.
Zimny. S. & Pfohl M. (2005). "Healing times and prediction of wound healing in neuropathic diabetic foot ulcers: a prospective study," Experimental and Clinical Endocrinology & Diabetes, 113(2). pp. 90-93.
Martinez, D., et al. "Wound healing response of the medial collateral ligament during hindlimb unweighting in young rats."
Rosenburg, L. (2003). "Wound healing, growth factors," Emedicine.
Mitragotri, S. (2000). "Synergistic effect of enhancers for transdermal drug delivery," Pharmaceutical Research, 17(11). pp. 1354-1359.
Mitragotri, S., et al. (2000). "Analysis of ultrasonically extracted interstitial fluid as a predictor of blood g levels," Journal of Applied Physiology, 89(3). pp. 961-966.
Anvar, M.D. et al (2000). "Vascular and stromal features in the skin of the lower limb in patients with critical limb ischaemia," European Journal of Vascular and Endovascular Surgery, 20(2) pp. 125-131.
Eichler, W., et al. (2000). "Changes of interstitial fluid volume in superficial tissues detected by a miniature ultrasound device," Journal of Applied Physiology, 89)1). pp. 359-363.
Mitragotri, S., et al. (2000), "Transdermal extraction of analytes using low-frequency ultrasound." Pharmaceutical Research, 17(4) pp. 466-470.
Moli, M, et al. (2000), "Two children with suspected primary vasculitis of messenteric vessels—a case report," Nihon Rinsho Meneki Gakkai Kaishi. 23(2). pp. 148-155.
Mitragotri, S., et al. (2000). "Synergistic effect of low-frequency ultrasound and sodium lauryl sulfate on transdermal transport," Journal of Pharmaceutical Science, 89(7) pp, 892-900.
Mitragotri, S., & Kost, J. (2000). "Low-frequency sonophoresis: A noninvasive method of drug delivery and diagnostics," Biotechnology in Progress, 16(3). pp. 488-492.
Taylor, B.K., et al. (2000). "Opioid inhibition of formalin-induced changes in plasma extravasation and blood flow in rats," PAIN, 84(2-3). pp. 263-270.
Fang, J., et al. (1999). "Effect of low-frequency ultrasound on the in vitro percutaneous absorption of clobetasol 17-propionate," International Journal of Pharmaceutics, 191(1). pp. 33-42.
Shoab, S.S., et al. (1999). "Plasma VEGF as a marker of therapy in patients with chronic venous diseases with oral micronised flavonoid fraction—a pilot study," European Journal of Vascular and Endovascular Surgery, 18(4). pp. 334-338.
Meidan, V.M., et al. (1999). "Ultrasound-enhanced diffusion into coupling gel during phonophoresis of 5-fluorouracil," International Journal of Pharmaceutics, 185(2). pp. 205-213.
Terai, M., et al. (1999). "Vascular endothelial growth factor in acute Kawasaki disease," American Journal of Cardiology, 83(3). pp. 337-339.
Singer, A.J., et al. (1999). "The effects of low-frequency ultrasound on Staphylococcus epidermidis," Current Microbiology, 38(3). pp. 194-196.
Foldvari, M., et al. (1998). "Liposome encapsulated prostaglandin E1 in erectile dysfunction: Correlation in vitro delivery through foreskin and efficacy in patients," Urology, 52(5). pp. 838-843.
Wu, J., et al. (1998), "Defects generated in human stratum corneum specimens by ultrasound," Ultrasound in Medicine and Biology, 24(5), pp. 705-710.
Liu, J., Lewis, T.N., & Prausnitz. M.R. (1998) "Non-invasive assessment and control of ultrasound-mediated mernbranel permeabilization," Pharmaceutical Research, 15(6), pp. 918-924.
Pedder, V.V., et al. (1998), "Rationale of noninvasive method of drug administration at the prelymphatic," MED TEKH, 2 pp, 18-23.
Sigfridsson et al. (1995),"Electrogenetic light reactions in photsystem I: resolution of electron-transfers rates be tween the iron-sulfer centers," Proc. National Acadamy of Science U.S.A., pp. 3456-3462. (Abstract).
Voigt et al. (2002), "Spectral Substructure and Excitonic Interactions in the Minor Photosystem II Antenna Complex CP29 Revealed by Nonlinear Polarization Spectroscopy in Frequency Domain," Biochemistry, pp. 3049-3056. (Abstract).
Dacher et al. (2001), "Combined NPLC-MS and HPLC-NMR on-line coupling for the separation and determination of lutein and zeaxanthin stereoisomers in spinach and in retina," Analytical Chemistry, pp. 667-674. (Abstract).
Varani et al. (2001), "Inhibition of type I procollagen synthesis by damages collagen in photoaged skin and by collagenase-degraded collagen in vitro," American Journal of Pathology, pp. 931-941. (Abstract).
Yu et al. (1997), "Photomodulation of oxidative metabolism and electron chain enzymes in rat liver mitochondria," Photochem. Photobiol., pp. 866-871. (Abstract).
Quan et al. (2002), "Connective tissue growth factor: expression in human skin in vivo and inhibition by ultraviolet radiation," Journal of Investigative Dermatology, pp. 402-408. (Abstract).

(56) References Cited

OTHER PUBLICATIONS

Boudjelal et al. (2002), "Retinoid Signaling Is Attenuated by Protassome-Mediated Degradation of Retinoid Receptors in Human Keratinocyte HaCaTCells," Exp. Cell. Res., pp. 130-137. (Abstract).
Loschinger et al. (1998), "Stimulation of protein kinase A activity and induced terminal differentiation of human skin fibroblasts in culture by low-frequency electromagnetic fields." Toxicol. Lett., pp, 369-76. (Abstract).
Bourguignon, GJ, and Bourguignon, LY, (1987), "Electric stimulation of protein and DNA synthesis in human fibroblasts," FASBERS J., pp. 398-402. (Abstract).
Bourguignon et al. (1989), "Electric stimulation of human fibroblasts causes an increase in Ca2+influx and the exposure of additional insulin receptors," Journal of Cellular Physiology, pp. 379-385. (Abstract).
Quan et al. (2001), "Ultraviolet irradiation blocks cellular responses to transforming growth factor-beta by down-regulating its type-II receptor and inducing Smad7," Journal of Biological Chemistry, pp. 26349-26356, (Abstract).
Neudecker, B.A., et al. (2004) "Abberant Serum Hyaluronan and Hyaluronidase Levels in Scleroderma," The British Journal of Dermatology pp. 469-476.
Formby, Bent, et al. (2002) "Lactate Stimulates Hyaluronan and CD44 Expression in Cultured Fibroblasts: the Warburg Effect Revisited," Experimental Cell Research May 15, 2002;276(1):24-31.
Stern, Robert. (2001) "Minireview on the Mammalian Hyaluronidases: Introductory Remarks" pub. by Elsevier Science B.V., Matrix Biology p. 497.
Csoka, Antonei, B. (2001) "Minireview the Six Hyaluronidase-like Genes in Human and Mouse Genomes" pub. by Elsevier Science B.V., Matrix Biology pp. 499-508.
Boh, Erin E. (2001) "Free Radicals and Aging Skin" Cosmetic Dermatology vol. 14 No. Dec. 12, 2001 pr. 37-40.
Lubart, R. et al. (1992) "Effect of Light on Calcium Transport in Bull Sperm Cells" Journal of Photochemuistry Photobiology B. Sep. 15, 1992;15(4):337-41.
Webster, Guy (2001) "Acne Pathogenesis & update on Therapy" Jujisawa Healthcare, Inc. Lectureship Series IN Dermatology [pamphlet] pp. 1-24.
Loschinger, Monika (1998) "Stimulation of Protein Kinase A Activity and Induced Terminal Differentiation of Human Skin Fibroblasts in Culture by Low-Frequency Electromagnetic Fields" Toxicol Lett. Aug. 1998: pp. 96-97:369-76.
Bedi, Monika K. (2002) "Herbal therapy in dermatology" Archives of Dermatology Feb. 2002 pp. 138(2):232-42.
Yu, Wei. (1997) "Photomodulation of Oxidative Metabolism and electron Chain Enzymes in Rat Liver Mitochondria" Photochemistry and Photobiology. Dec. 1997:66(6):866-71.
Barber, James (2002) "Short communication: P680 What is it and Where is it?" Bioelectrochemistry, vol. 55, No. 1, Jan. 2002 , pp. 135-138(4).
Matsuad, Tatsuru et al. (2002) "Biosynthesis and distribution of Chlorophyll Among the Photosystems During recovery of the Green Alga Dunaliella Salina From Irradiance Stress" Plant Physiology. Feb. 2002;128(2):603-14.
De Mattei, M, et al. (2001) "Effect of Pusled Electromagnetic Fields on human Articular Chodrocyte Proliferation" Connective Tissue Research 2001;42(4):269-79.
Krishtalik, Li et al. (2000) "Effects of Medium Polarization and Pre-Existing Field on Activation Energy of Enzymatic Charge-Transfer Reactions" Biochimica Biophysica Acta. Jul. 20, 2000;1459(1):88-105.
Edwards, AM, Silva, E. "Effect of Visible Light on Selected Enzymes, Vitamins and Amino Acids" Journal of Photochemistry Photobiology B. Oct. 2001;63(1-3):126-31.
Sommer, Andrei P. "Abstracts From the 1st International workshop on Nearfield Optical Analysis, Reisenberg, Germany, Nov. 2000" Journal of Clinical Laser Medicine & Surgery vol. 19 No. 2 2001.

Ishgaki Y., et al. (1999) "Development and Characterzation of a DNA Solar Dosimeter," Journal of Photochemistry and Photobiolgy, 50. pp. 184-188.
Gross, A. (1999). "Entering the Japanese Medical Device Market: The latest trends mean even better opportunities for foreign medical technology manufacturers," Medical Devicelink, Accessed: Dec. 15, 2001.
Gross, A., & Dyson, P. (1996). "Changing Regulatory Climate Improves Korean Market of U.S. Companies," Medical Device and Diagnostic Industry.
LeDoux, S.P., & Wilson, G.L. (2001). "Base Excision Repair of Mitochondrial DNA Damage in Mammalian Cells," Progress in Nucleic Acid Research and Molecular Biology, 66. pp. 273-284.
Turnbull, D., & Lightowlers, R. (2001). "Might Mammalian Mitochondria Merge?" Nature Medicine, 7(6). pp. 895-896.
Nakada, K., et al. (2001). "Inter-mitochondrial complementation: Mitochondria-specific system preventing mice from expression of disease phenotypes by mutant mtDNA," Nature Medicine, 7(8). pp. 934-940.
Vogel, W.F. (2001) "Collagen-receptor signaling in health and disease," European Journal of Dermatology, 11(6). pp. 506-514.
Curat, C., et al. (2001) "Mapping of eptiopes in discoidin domain receptor 1 critical for collagen binding," Journal of Biological Chemistry, 6(49).
Hou G., Vogel, W., & Bendeck, M.P, (2001). "The discoidin domain receptor tyrosine kinase DDR1 in arterial wound repair," Journal of Clinical Investigation, 107(6). pp. 727-735.
Chin, G.S., et al. (2000), "Cellular signaling by tyrosine phosphorylation in keloid and normal human dermal fibroblasts," Plastic Reconstructive Surgery, 106(7), pp. 1532-1540.
Weiner, H.L., et al. (2000). "Consistent and selective expression of the discoidin domain receptor-1 tyrosine kinase in human brain tumors," Neurosurgery, 47(6). pp. 1400-1409.
Chin, G.S. et al. (2000), "Differential expression of receptor tyrosine kinases and Shc in fetal and adult rat fibroblasts: Toward defining scarless versus scarring fibroblast phenotypes," Plastic Reconstructive Surgery, 105(3). pp. 972-979.
Vogel, W., et al. (2000). "Discoidin domain receptor 1 is activated independently of beta 1 integrin," Journal of Biological Chemistry 275(8). pp. 5779-5784.
Vogel, W. (1999). "Discoidin domain receptors: Structural relations and functional implications," FASEB Journal, 13, pp. 77-82.
Norman, J.T., & Fine, L.G. (1999). "Progressive renal disease: Fibroblasts, extracellular matrix, and integrins," Experimental Nephrology, 7(2). pp. 167-177.
Shrivastava, A., et al. (1997). "An orphan receptor tyrosine kinase family whose members serve as nonintegrin collagen receptors," Molecular Cell, 1(1). pp. 25-34.
Vogel, W., et al. (1997). "The discoidin domain receptor tyrosine kinases are activated by collagen," Molecular Cell, 1 (1). pp. 13-23.
Sakuma, S., et al. (1996). "Receptor protein tyrosine kinase DDR is up-regulated by p53 protein," FEBS Letters, 2. pp. 398, 165-169.
Hardell, L., et al. (2001). "Ionizing radiation, cellular telephones and the risk for brain tumors," European Journal of Cancer Prevention, 10(6). pp. 523-529.
Seishima, M., Oyama. Z., & Yamamura, M. (2002). "Cellular phone dermatitis," Archives of Dermatology, 138(2). pp. 272-273.
Di Carlo. A., et al, (2002), "Chronic electromagnetic field exposure decreases HSP70 levels and lowers cytoprotection, " Journal of Cellular Biochemistry, 84(3). pp. 447-454.
French, P.W., et al. (2001). "Mobile phones, heat shock proteins and cancer," Differentiation, 67(4-5). pp. 93-97.
Frumkin, H., et al. (2001). "Cellular phones and risk of brain tumors," CA: A Cancer Journal for Clinicians, 51(2). pp. 137-141.
Moustafa, Y.M., et al. (2001). "Effects of acute exposure to the radiofrequency fields of cellular phones on plasma lipid peroxide and antioxidase activities in human erythrocytes," Journal of Pharmaceutical and Biomedical Analysis, 26(4). pp. 605-608.
Chiladakis, J.A., et al. (2001). "In-vivo testing of digital cellular telephones in patients with implantable cardioverter-defibrillators," European Heart Journal, 22(15). pp. 1337-1342.
Santini, R., et al. (2001). "Symptoms reported by mobile cellular telephone users." Pathological Biology, 49(3). pp. 222-226.

(56) References Cited

OTHER PUBLICATIONS

Roti, J.L., et al. (2001). "Neoplastic transformation in C3H 10T(1/2) cells after exposure to 835.62 MHz FDMA and 847.74 CDMA radiations," Radiation Research, 155(1-2). pp. 239-247.
Wainwright, P. (2000). "Thermal effects of radiation from cellular telephones," Physics in Medicine and Biology, 152 (3). pp. 293-302.
Adey, W.R., et al. (1999). "Spontaneous and nitrosourea-induced primary tumors of the central nervous system in Fischer 344 rats chronically exposed to 836 MHz modulated microwaves," Radiation Research, 152(3). pp. 293-302.
Robert, E. (1999). "Intrauterine effects of electromagnetic fields— (low frequency, mid-frequency RF, and microwave): A review of epidemiologic studies,"Teratology, 59(4). pp. 292-298.
De Seze, R., Fabbro-Peray, P., & Miro, L. (1998), "GSM radiocellular telephones do not disturb the secretion of antepituitary hormones in humans." Bioelectromagnetics, 19(5), pp, 271-278.
Malyapa, R.S., et al. (1997). "Measurement of DNA damage after exposure to electromagnetic radiation in the cellular phone communication frequency band (835.62 and 847.74 MHz)," Radiation Research, 148(6). pp. 618-627.
Litovitz, T.A., et al. (1997). "Bioeffects induced by exposure to microwaves are mitigated by superposition of ELF noise," Bioelectromagnetics. 18(6). pp. 422-430.
Omura, Y., & Losco, M. (1993), "Electro-magnetic fields in the home environment (color TV, computer monitor, microwave oven, cellular phone, etc) as potential contributing factors for the induction of oncogen C-fos Ab1, oncogen C-fos Ab2, integrin alpha 5 beta 1 and development of cancer, as well as effects of microwave on amino acid composition of food and living human brain," Acupuncture and Electro-Theraputics Research, 18(1). pp. 33-73.
Knave, B. (2001). "Electromagnetic fields and health outcomes," Annals Academy of Medicine Singapore, 30(5). pp. 489-493.
De Seze, R., et al. (1999). "Evaluations in humans of the effects of radiocellular telephones on the circadian patterns of melatonin secretion, a chronobiological rhythm marker," Journal of Pineal Research, 27(4). pp. 237-242.
Fluhr, J.W., et al. (1999). "In-vitro and in-vivo efficacy of zinc acetate against propionibacteria alone and in combination with erythromycin," Zentralbl Bakteriol, 289(4). pp. 445-456.
Itoh, Y., et al. (2001). "Photodynamic therapy of acne vulgaris with topical delta-aminolaevulinic acid and incoherent light in Japanese patients," British Journal of Dermatology, 144(3). pp. 575-579.
Lang, K., et al. (2001). "Aminolevulinic acid: Pharmacological profile and clinical indication," Expert Opinion on Drug Discovery, 10(6). pp. 1139-1156.
Ashmead, H.D. "The Need for Better Nutrition in our Food." Clearfield, Utah. USA. pp. 1-20.
Van Remmen, H. & Richardson, A. (2001). "Oxidative Damage to Mitochondria and Aging," Experimental Geology 36, pp. 957-968.
Rice, B.W., et al. (2001), "In Vivo Imaging of Light-emitting Probes," Journal of Biomedical Optics 6(4), pp. 432-440.
Moretti, M. 2001), "ICN Develops Integrated Skin Treatment Package," Aesthetic Buyers Guide Nov. 2001.
Neudecker. B.A., Stern, R. & Connolly. M.K. "Aberrant Serum Hyaluronan and Hyaluronidase Levels in Scleroderma," Department of Pathology and Dermatology, School of Medicine, University of California San Francisco.
Leyden, J., et al. (1999). "Finasteride in the Treatment of Men with Frontal Male Pattern Hair Loss," Journal of the American Academy of Dermatology 40(6). pp. 930-937.
Sommer, A.P, et al. (2001). "Biostimulatory Windows in Low-Intensity Laser Activation: Lasers, Scanners, and NASA's Light-Emitting Diode Array System," Journal of Clinical Laser Medicine and Surgery 19(1). pp. 29-33.
Troy, T. (2002). "Fluorescent Pulsed Light Makes Foray," Dermatology Times Jan. 2002.
Panteleyev, A., Jahoda, C., & Christiano, A. (2001). "Hair Follicle Predetermination," Journal of Cell Science 114. pp. 3419-3431.

Yoon, J.H., et al. (2000). "The DNA Damage Spectrum Produced by Simulated Sunlight," Academic Press, pp. 681-693.
Draper, B., et al. (2002). "MNPs and TIMP-1 are Differentially Expressed Between Acute Murine Excisional and Laser Wounds," Lasers in Surgery and Medicine 30, pp. 106-116.
Yano, K. Lawrence, B.F., & Detmar, M. (2001). "Control of hair growth and follicle size by VEGF-mediated angiogensis." The Journal of Clinical Investigation, 107(4), pp. 409-417.
Wei, Y. H., et al. (2001). "Mitochondrial theory of aging matures— Roles of mtDNA mutuation and oxidative stress in human aging." Chinese Medical Journal, 64, pp. 259-270.
Hoffman, J.W., et al (2004). "Myocardial reperfusion injury: Etiology, mechanisms, and therapies." The Journal of the American Society of Extra-Corporeal Technology, 36, pp. 391-411.
Chwirot, W.B. (1986). "New indications of possible role of DNA in ultraweak photon emission from biological systems." Journal of Plant Physiology, 122, pp. 81-86.
Albrecht-Buehler, G. (1994). "Cellular infrafred detector appears to be contained in the centrosome." Cell Motility and the Cytoskeleton 27, pp. 262-271.
Kiang, J.G. (2004). "Inducible heat shock protein 70kD and inducible nitric oxide synthase in hemorrhage/resuscitation-induced injury." Cell Research, 14(6), pp. 450-459.
Yu, W., et al (1997). "Improvement of host response to sepsis by photobiomodulatio." Lasers in Surgery and Medicine, 21(3), pp. 262-268.
Byrnes, K.R., et al. (2004). "Photobiomodulation improves cutaneous wound healing in an animal model of type II diabetes." Photomedicine and Laser Surgery, 22(4), pp. 281-290.
Byrnes. K.R., et al. (2005). "Light promotes regeneration and functional recovery and alters the immune response after spinal cord injury." Lasers in Surgery and Medicine. Feb. 09, (online).
Wong-Riley. M.T., et al. (2005), "Photobiomodulation directly benefits primary neurons functionally inactive by toxins: role of cytochrome c oxidase." Journal of Biological Chemistry, 280(6), pp. 4761-4771.
El Hindi, T., et al, (2004), "Determination of the antioxidant capacity of an antioxidant combination using the fluoroscan assay in vitro and visualization of its effects using histological methods." Archives of Dermatological Research, 296(5), pp. 258-264.
Elmets, C.A., Vargas, A., & Oresajo, C. (1992). "Photoprotective effects of sunscreens in cosmetics on sunburn and Langerhans cell photodamage." Photodermatology, Photoimmunology, and Photomedicine, 9(3), pp. 113-120.
Stein, R. (2005). "Fat found to accelerate aging process." Washington Post, Jun. 14, 2005.
Block, G., et al. (2004). "Plasma-C reactive protein concentrations in active and passive smokers: influence of antioxidant supplementation." Journal of the American College of Nutrition, 23(2), pp. 141-147.
Noda, Y., et al. (2002). "Antioxidant activities of pomegranate fruit extract and its anthocyanindins: delphindin, cyaniding, and pelagronidin." Journal of Agricultural and Food Chemistry, 50(1), pp. 166-171.
Monaco, J.L. & Lawrence, W.T. (2003). "Acute wound healing an overview." Clinics in Plastic Surgery, 30, pp. 1-12.
Hinz, B., et al. (2001). "Apha-smooth muscle actin expression upregulates fibroblast contractile activity." Molecular Biology of the Cell, 12, pp. 2730-2741.
Azevedo, L.H., et al. (2005). "Evaluation of low intensity laser effects on the thyroid gland of male mice." Photomedicine and Laser Surgery, 23(6), pp. 567-570.
Tuby, H., Maltz. L., & Oron, U. (2006). "Modulations of VEGF and iNOS in the rat heart by low level laser therapy are associated with cardioprotection and enhanced angiogensis." Lasers in Surgery and Medicine, 38, pp. 682-688.
Fratelli, M., et al. (2005), "Gene expression in profiling reveals a signaling role of gluthathione in redox regulation." PNAS, 102(39), pp. 13998-14003.
Hymes, S.R., Strom, E.A., & Fife, C. (2006). "Radiation dermatitis: Clinical presentation, pathophysiology, and treatment 2006." Journal for the American Academy of Dermatology, 54, pp. 28-46.

(56) References Cited

OTHER PUBLICATIONS

Omura, Y. (2004). "Special sunrise & sunset solar energy stored papers and their clinical applications for intractable pain, circulatory disturbances & cancer Comparison of Beneficial effects between special solar energy stored paper and quigong energy stored paper." Acupuncture & Electro-therapeutios, 29, pp. 1-42.
Stoica, E. & Enulescu, O. (1988). "Catecholamine response to light in migraine" Cephalalgia, 8, pp. 31-36.
Kowluru, R.A. (2005). "Diabetic retinopathy: mitochondrial dysfunction and retinal capillary cell death." Antioxidants & Redox Signaling, 7(11,12), pp. 1581-1587.
McDaniel, D. et al. (1998). "Body contourng: A preliminay report on the use of the silhouette® device for treating cellulite." Aeshetic Surgery Journal, 18(3), pp. 177-182.
Noton, D. (2000). "Migraine and photic stimulation: Report on a survey of migraineurs using flickering light therapy." Complementary Therapies in Nursing & Midwifery, 6, pp. 138-142.
Alstadhaug, K.B., Salvesen, R., & Bekkelund, S.I. (2005). "Seasonal variation in migraine." Cephalalgiai, 25, pp. 811-816.
Claustrat, B., et al. (2004). "Melatonin secretion is supersensitive to light in migraine." Cephalalgia, 24, pp. 128-133.
Passache, G., et al. (2000). "Mitochondria of retnal muler (glial) cells: The effects of aging and of application of free radical scavengers." Opthalmic Research, 32, pp. 229-236.
Liang, F.Q. & Godley, B.F. (2003). "Oxidative stress-induced mitochondrial DNA damage in human retinal pigment epithelial cells: A possible mechanism for RPE aging and age-related macular degeneration." Experimental Eye Research, 76, pp. 397-403.
Anderson, D.J., et al. (1997), "Preliminary trial of photic stimulation for premenstrual syndrome," Journal of Obstetrics and Gynaecology, 17(1), pp. 76-79.
Main, A., et al. (2000). "The wavelength of light causing photophobia in migraine and tension-type headache between attacks." Headache, 40, pp. 194-199.
Eells, J.T., et al. (2004). "Mitochondrial signal transduction in accelerated wound and retinal healing by near-infrared light therapy." Mitochondrion, 4. pp, 559-567.
"Thiol" From Wikipedia page http://en.wikipedia.org/wiki/Thiol Accessed: May 6, 2007.
"Disulfide Bond" From Wikipedia page http://en.wikipedia.org/wiki/Disulfide_bond Accessed: May 6, 2007.
"Permanent Wave" From Wikipedia page http://en.wikipedia.org/wiki/Permanent_wave Accessed: May 6, 2007.
Martin, K. (2007). "Infrared and ramen studies of skin and hair: A review of cosmetic spectroscopy." The Internet Journal of Vibrational Spectroscopy, 3(2), online Accessed: Apr. 24, 2007.
Jarrousse, F., et al. (2001). "Identification of clustered cells in human hair follicle responsible for MMP-9 gelatinolytic activity: Consequences for the regulation of hair growth." International Journal of Dermatology, 40(6), pp. 385-392..
Langbein, et al. (2001). "Figure 8." Journal of Biological Chemistry, 276(37), pp. 35123.
King, A., et al. (2004). "Mitochondria-derived reactive oxygen species mediate blue light-induced death of retinal pigment epithelial cells." Photochemistry and Photobiology, 79(5), pp. 470-475.
"The EpiOcular™ Model." http://www.mattek.com/pages/products/epiocular. Mattek Corporation. Accessed: Apr. 27, 2005.
"Foliquant® A range of in vivo asays of hair follicle damage and alopecia." EpiStem® Ltd. Copyright 2003 Epistem Ltd.
Davis, S.C., et al. (2004). "To examine the effect of GentleWaves LED photomodulation device on deep partial thickness wound healin." Preliminary Protocol: Deep Partial thickness wound study. Department of Dermatology and Cutaneous Surgery, University of Miami School of Medicine.
"Virulite CS®. . . The ORIGINAL Cold Sore Machine." http://www.virulite.com/technical_information.html Date accessed: Jan. 26, 2008.
Christensen, B. (2008). "Forced resonance ultra-short pulse laser kills viruses dead." Technovelogy.com Where Science Meets Fiction, http://www.technovelogy.com/ct/Science-Fiction-News.asp?NewsNum=1311. Date Accessed: Jan. 26, 2008.
"Visual Signal Tansduction." Biocarta http://www.biocarta.com/pathfiles/h_rhodospinPathway.asp Date Accessed: Aug. 29, 2005.
Epstein, P. 2007 ). "Trials that matter: Two faces of progress in the treatment of age-related macular degeneration." Annals of Internal Medicine, 146(7), pp. 532-534.
Ostler, E.L. et al. (2000) "Telomerase and the cellular lifespan: Implications of the aging process." Journal of Pediatric Endocrinology and Metabolism, 13(6), pp. 1467-1476.
Lou, H. J. et al.(2002). "Lighting the way: Molecular beacons offer a highly sensitive, flexible method for DNA analysis." Spie's OEMagazine, February, pp. 23-25.
"The Relief Light: A sensible alternative to 'soft' laser technology." Retrieved: http://www.fredomunlimited.net/relief%20light.htm Date Accessed: Feb. 9, 2002.
Stern, R. et al. (2001)."Hyaluronidase can modulate expression of CD44." Experimental Cell Research, 265, pp. 1-10.
Mio, K. et al. (2000). "Evidence that the serum inhibitor of hyaluronidase may be a member of the inter-a-inhibitor family." Journal of Biological Chemistry, 275(42), pp. 32413-32421.
Mortimer, A.J., & Dyson, M. (1988). "The effect of therapeutic ultrasound on calcium uptake in fibroblasts." Ultrasound in Medicine and Biology, 14(6), pp. 499-506.
Office Action issued Sep. 13, 2013 in U.S. Appl. No. 12/550,746.
Canadian Office Action dated May 30, 2013 issued in Canadian Patent Application No. 2,533,129.
Translation of amended claims filed in response to Second/Final Notice of Reasons for Rejection dated Feb. 20, 2013 issued in Japanese Patent Application No. 2008-553383.
Translation of Written Amendment filed Aug. 6, 2013 in response to Second/Final Notice of Reasons for Rejection dated Feb. 6, 2013 issued in Japanese Patent Application No. 2008-557382.
Response filed May 31, 2013 to office action dated Nov. 16, 2012 in Chinese Patent Application No. 201110210275.4.
Decision on Rejection issued Jun. 28, 2013 in Chinese Patent Application No, 201110210275.4.
Japanese Office Action dated Jan. 8, 2014, issued in Japanese Application No. 2008-557382, filed Mar. 2, 2007, GentleWaves LLC.
Japanese Office Action dated Feb. 10, 2014, issued in Japanese Application No. 2008-553383, filed Feb. 2, 2007, GentleWaves LLC.
Response to Office Action dated Jul. 2, 2007 for European Patent Application No. 02792232.7.
Office Action dated Jun. 22, 2009 for European Patent Application No. 02792232.7.
Response to Office Action dated Jun. 22, 2009 for European Patent Application No. 02792232.7.
Office Action dated Oct. 18, 2010 for European Patent Application No. 02792232.7.
Office Action dated Oct. 10, 2012 for European Patent Application No. 02792232.7.
First Examination Report dated Jul. 12, 2007 for Indian Patent Application No. 620/KOLNP/2004.
Official Action dated Feb. 14, 2008 for Israeli Patent Application No. 161865.
Response to Official Action dated Feb. 14, 2008 for Israeli Patent Application No. 161865.
Office Action dated Sep. 15, 2010 for Israeli Patent Application No. 161865.
Response to Office Action dated Sep. 15, 2010 for Israeli Patent Application No. 161865.
Office Action dated May 14, 2008 for Japanese Patent Application No. 2003-541770.
Report of Final Decision of Refusal dated Feb. 6, 2009 for Japanese Patent Application No. 2003-541770.
Office Action dated Sep. 23, 2009 for Korean Patent Application No. 700706012004.
Response to Office Action dated Sep. 23, 2009 for Korean Patent Application No. 7007060/2004.
Office Action dated Jul. 27, 2010 for Korean Patent Application No. 7007060/2004.

(56) References Cited

OTHER PUBLICATIONS

Response to Office Action dated Jul. 27, 2010 for Korean Patent Application No. 7007060/2004.
Appeal Brief dated Nov. 26, 2010 for Korean Patent Application No. 7007060/2004.
Office Action dated Dec. 9, 2010 for Korean Patent Application No. 7007060/2004.
Response to Office Action dated Dec. 9, 2010 for Korean Patent Application No. 7007060/2004.
Office Action dated Jan. 17, 2012 for Korean Patent Application No. 70007060/2004.
Official Letter dated May 21, 2008 for Mexican Patent Application No. 2004/004463.
Response to Official Letter dated May 21, 2008 for Mexican Patent Application No. 2004/004463.
Examination Report dated Mar. 13, 2006 for New Zealand Patent Application No. 533303.
Search Report dated May 22, 2008 for PCT Patent Application No. PCT/US07/02958.
Search Report dated May 27, 2008 for PCT Patent Application No. PCT/US07/05288.
Search Report dated Sep. 18, 2008 for PCT Patent Application No. PCT/US07/05288.
Examiner's first report dated Aug. 5, 2010 for Australian Patent Application No. 2007212519.
Response to Office Action dated Feb. 29, 2012 for Japanses Patent Application No. 2008-553383.
Office Action dated Feb. 29, 2012 for Japanese Patent Application No. 2008-553383.
Office Action dated Aug. 26, 2011 for European Patent Application No. 07763561.3.
Voluntary Amendment dated Dec. 4, 2008 for European Patent Application No. 07763561.3.
Search Report and Opinion dated Apr. 23, 2009 for European Patent Application No. 07763561.3.
First Examination Report dated Aug. 19, 2009 for European Patent Application No. 07763561.3.
Response to First Examination Report dated Aug. 19, 2009 for European Patent Application No. 7763561.3.
Response to Office Action dated Mar. 31, 2012 for Japanese Patent Application No. 2008-557382.
Office Action dated Mar. 21, 2012 for Japanese Patent Application No. 2008-557382.
Invitation to Correct Defects dated Jul. 22, 2002 for PCT Patent Application No. PCT/US02/20706.
Response to Invitation to Correct defects dated Jul. 22, 2002 for PCT Patent Application No. PCT/US02/20706.
Written Opinion dated Jul. 31, 2003 for PCT Patent Application No. PCT/US02/20706.
Response to Written Opinion dated Jul. 31, 2003 for PCT Patent Application No. PCT/US02/20706.
Preliminary Examination Report dated Oct. 27, 2005 for PCT Patent Application No. PCT/US02/20706.
International Search Report dated Aug. 11, 2003 for PCT Patent Application No. PCT/US03/10509.
Preliminary Examination Report dated Jun. 17, 2004 for PCT Patent Application No. PCT/US03/10509.
Official Action dated Jul. 28, 2010 for Israeli Patent Application No. 159579.
Official Action dated Sep. 8, 2008 for Israeli Patent Application No. 159579.
Response to Official Action dated Sep. 8, 2008 for Israeli Patent Application No. 159579.
Voluntary Amendment dated Apr. 19, 2006 for Canadian Patent Application No. 2452408.
Office Action dated Jun. 2, 2006 for Canadian Patent Application No. 2452408.
Response to Office Action dated Jun. 2, 2006 for Canadian Patent Application No. 2452408.
Office Action dated Mar. 2, 2007 for Canadian Patent Application No. 2452408.
Response to Office Action dated Mar. 2, 2007 for Canadian Patent Application No. 2452408.
Office Action dated Jan. 31, 2008 for Canadian Patent Application No. 2452408.
Response to Office Action dated Jan. 31, 2008 for Canadian Patent Application No. 2452408.
Office Action dated Nov. 10, 2008 for Korean Patent Application No. 7017182/2003.
Notices for Reasons of Rejection dated Mar. 26, 2008 for Japanese Patent Application 2003-508231.
Amendment to Notices for Reasons of Rejections dated Mar. 26, 2008 for Japanese Patent Application No. 2003-508231.
Decision of Rejection dated Feb. 2, 2009 for Japanese Patent Application No. 2003-508231.
Examination Report dated Feb. 22, 2008 for New Zealand Patent Application No. 530600.
Response to Examination Report dated Feb. 22, 2008 for New Zealand Patent Application No. 530600.
Examination Report dated Aug. 20, 2008 for New Zealand Patent Application No. 530600.
Official Letter dated Nov. 17, 2006 for Mexican Patent Application No. 2004/000187.
Second Official Letter dated Jul. 27, 2007 for Mexican Patent Application No. 2004/000187.
Response to Second Official Letter dated Jul. 27, 2007 for Mexican Patent Application No. 2004/000187.
Third Official Letter dated Jan. 3, 2008 for Mexican Patent Application No. 2004/000187.
Response to Third Official Letter dated Jan. 3, 2008 for Mexican Patent Application No. 2004/000187.
Office Action dated Mar. 21, 2008 for Chinese Patent Application No. 02816794.5.
Response to Office Action dated Mar. 21, 2008 for Chinese Patent Application No. 02816794.5.
Second Office Action dated Jul. 22, 2009 for Chinese Patent Application No. 02816794.5.
Response to Second Office Action dated Jul. 22, 2009 for Chinese Patent Application No. 02816794.5.
Third Office Action dated Jan. 5, 2010 for Chinese Patent Application No. 02816794.5.
Response to Third Office Action dated Jan. 5, 2010 for Chinese Patent Application 02816794.5.
First Examination Report dated Feb. 8, 2007 for European Patent Application No. 02749720.
First Statement of Proposed Amendments dated Feb. 17, 2006 for Australian Patent Application No. 2003220671.
Examiner's First Report dated Oct. 4, 2007 for Australian Patent Application No. 2003220671.
Voluntary Amendment dated Apr. 27, 2007 for Canadian Patent Application No. 2482934.
Office Action dated Jun. 15, 2007 for Canadian Patent Application No. 2482934.
Response to Office Action dated Jun. 15, 2007 for Canadian Patent Application No. 2482934.
Office Action dated Feb. 21, 2008 for Canadian Patent Application No. 2482934.
Response to Office Action dated Feb. 21, 2008 for Canadian Patent Application No. 2482934.
Office Action dated Oct. 17, 2008 for Canadian Patent Application No. 2482934.
Response to Office Action dated Oct. 17, 2008 for Canadian Patent Application No. 2482934.
Office Action dated Jun. 3, 2010 for Canadian Patent Application No. 2482934.
Response to Office Action dated Jun. 3, 2010 for Canadian Patent Application No. 2482934.
Office Action dated Feb. 1, 2011 for Canadian Patent Application No. 2482934.
First Office Action dated Mar. 10, 2006 for Chinese Patent Application No. 03813556.6.

(56) References Cited

OTHER PUBLICATIONS

Response to First Office Action dated Mar. 10, 2006 for Chinese Patent Application No. 03813556.6.
Second Office Action dated May 23, 2008 for Chinese Patent Application No. 03813556.6.
Response to Second Office Action dated May 23, 2008 for Chinese Patent Application No. 03813556.6.
Rejection Decision dated Oct. 30, 2009 for Chinese Patent Application No. 03813556.6.
Response to Rejection Decision dated Oct. 30, 2009 for Chinese Patent Application No. 03813556.6.
First Office Action dated Dec. 12, 2008 for Indian Patent Application No. 1590/KOLNP/2004.
Withdrawal Petition dated Nov. 20, 2009 for Indian Patent Application No. 1590/KOLNP/2004.
Written Opinion of the International Search Authority dated Apr. 12, 2005 for PCT Patent Application No. PCT/US04/10915.
European Search Report dated Oct. 6, 2010 for EP Application No. 04759316.5.
Office Action dated Feb. 2, 2011 for EP Application No. 04759316.5.
Official Action dated Oct. 25, 2006 for Canadian Patent Application No. 2531099.
First Office Action dated May 22, 2009 for Chinese Patent Application No. 200480021576.0.
Office Action dated Dec. 7, 2010 for Japanese Patent Application No. 2006-509834.
Response to Office Action dated Dec. 7, 2010 for Japanese Patent Application No. 2006-509834.
Office Action dated May 11, 2010 for Japanese Patent Application No. 2006-509834.
Response to Office Action dated May 11, 2010 for Japanese Patent Application No. 2006-509834.
Written Opinion of the International Search Authority dated Oct. 19, 2006 for PCT Patent Application No. PCT/US04/24879.
Office Action dated Feb. 28, 2012 for Canadian Patent Application No. 2533129.
Response to Office Action dated Feb. 28, 2012 for Canadian Patent Application No. 254412.
Office Action dated Jun. 17, 2011 for European Patent Application No. 4779826.9.
Response to Office Action dated Jun. 17, 2011 for European Patent Application No. 4779826.9.
First Office Action dated Jul. 15, 2009 for European Patent Application No. 04779826.9.
Response to First Office Action dated Jul. 15, 2009 for European Patent Application No. 04779826.9.
Office Action dated May 31, 2010 for Israeli Patent Application No. 173123.
Response to Office Action dated May 31, 2010 for Israeli Patent Application No. 173123.
Office Action dated Apr. 7, 2010 for Japanese Patent Application No. 2006-522123.
Response to Office Action dated Apr. 7, 2010 for Japanese Patent Application No. 2006-522123.
Office Action dated Apr. 28, 2011 directed towards Korean Patent Application 10-2006-7002207.
Response to Office Action dated Apr. 28, 2011 for Korean Patent Application 10-2006-7002207.
Office Action dated Aug. 12, 2011 for Korean Patent Application 10-2006-7002207.
Response to Office Action dated Aug. 12, 2011 for Korean Patent Application 10-2006-7002207.
"Apoptosis," dated Sep. 19, 2005, located at http:www.neuro.wustl.edu/NEUROMUSCULAR/mother/apoptosis.htm> retrieved on Oct. 24, 2007 (5 pages).
Lyons, R.F. et al., "Biostimulation of Wound Healing in Vivo by a Helium-Neon Laser", Ann Plast Surg, Jan. 1987; 18(1):47-50, (Abstract).
Menezes, Salatiel, et al., (1998) "Non-Coherent Near Infrared Radiation Protects Normal Human Dermal Fibroblasts from Solar Ultraviolet Toxicity".
Asawanonda et al., "308-nm Excimer Laser for the Treatment of Psoriasis", Arch Dermatol, vol. 136, May 2000, pp. 619-624.
Callaghan et al. (1996), "Reactive Oxygen Species Inducible by Low-intensity Laser Irradiation Alter DNA Synthesis in the Hemopoietic Cell Line", U937, Lasers Surg. Med. 19(2):201-206.
Ceccherelli et al. (1989), "Diode Laser in Cervical Myofascial Pain: A Double-blind Study Versus Placebo," The Clinical Journal of Pain 5:301-304.
Chung et al. (1996), "Histological Responses of Port Wine Stains in Brown Skin After 578 nm Copper Vapor Laser Treatment", Lasers Surg. Med. 18(4):358-366.
Database WPI Week 2000046 Derwent Publications Ltd., London, GB; AN 2000-511628; XP002373743 & JP 2000 202044 A (Yamana Co Ltd.) Jul. 25, 2000 *abstract*.
Freeman et al. (2004), "NGF Deprivation-induced Gene Expression: After Ten Years, Where Do We Stand?," Chapter 8 in Progress in Brain Research 146, Elsevier B.V., 111-126.
Gao et al. (Jul. 13, 2004), "Induction of Phase 2 Genes by Sulforaphane Protects Retinal Pigment Epithelial Cells Against Photooxidative Damage", PNAS 101(28:10446-10451).
Huang et al. (Aug. 2004), "Downregulation of ATP Synthase Subunit-6, Cytochrome c Oxidase-III, and NADH Dehydrogenase-3 by Bright Clinic Light in the Rat Retina". Investigative Ophthalmology & Visual Science 45 (8):2489-2496.
M. Suzuki et al. (May 1978), "Autoradiographic Study on Percutaneous Absorption of Several Oils Useful for Cosmetics", J. Soo, Cosmet. Shem., 29, 265-282.
Karu et al. (1996), "Effects of Monochromatic Low-intensity Light and Laser Irradiation on Adhesion of the HeLa Cells in Vitro", Lasers Surg. Med. 18(2):171-177.
Laakso, et al. (1997), "Pain Scores and Side Effects in Response to Low Level Laser Therapy (LLLT) for Myofascial Trigger Points", Laser Therapy 9:67-72.
Liberman et al. (1996), "Light Years Ahead", pp. 277-283.
Liu et al. (2002), "Inhibition of AP-1 Transcription Factor Causes Blockade of Multiple Signal Transduction Pathways and Inhibits Breast Cancer Growth", Oncogene 21:7680-7689.
Logdberg-Anderson et al. (1997), "Low Level Laser Therapy (LLLT) of Tendonitis and Myofascial Pains: a Randomized, Double-blind, Controlled Study", Laser Therapy 9:79-86.
McDaniel (May 2001), "Nonablative Skin Rejuvenation—The Wave of the Future", Cosmetic Surgery Times.
Hrnjak, M., et al. (Nov. 1995), "Stimulatory Effect of Low-Power Density He—Ne Laser Radiation on Human Fibroblast in Vitro", Vojnosanit Pregl. 52(6), pp. 539-546.
Vuillaume, et al. (2001), "Real Time RT-PCR Shows Correlation between Retinoid-Induced Apoptosis and NGF-R mRNA Levels", Biochemical and Biophysical Research Communications 289(3):647-652.
Wei, Li-Na (2004), "Retinoids and Receptor Interacting Protein 140 (RIP140) in Gene Regulation", Current Medicinal Chemistry 11(12):1527-1532.
Whelan et al., "NASA Light Emitting Diode Medical Applications From Deep Space to Deep Sea", CP552, Space Technology and Applications International Forum 2001, p. 35-45.
"Bandwidth", Wikipedia Website [http://en.wikipedia.org/wiki/Bandwidth].
Office Action dated Jul. 21, 2011 for U.S. Appl. No. 12/583,578.
Response to Office Action dated Jul. 21, 2011 for U.S. Appl. No. 12/583,578.
Final Office Action dated Apr. 11, 2012 for U.S. Appl. No. 12/583,578.
Response to Final Office Action dated Apr. 11, 2012 for U.S. Appl. No. 12/583,578.
Office Action dated Jun. 20, 2013 for U.S. Appl. No. 12/583,578.
Response to Final Office Action dated Dec. 3, 2012 for U.S. Appl. No. 12/550,799.
Final Office Action dated Jun. 14, 2007 for U.S. Appl. No. 10/903,483.
Appeal Brief filed Jan. 28, 2008 for U.S. Appl. No. 10/903,483.

(56) References Cited

OTHER PUBLICATIONS

Response to Official Notification dated Dec. 3, 2008 for Israeli Patent Application 171311.
Response to Second Office Action dated Nov. 2, 2007 Chinese Patent Application 200480012575.X.
International Preliminary Examination Report dated Aug. 6, 2004 for Patent Application PCT/US02/26627.
European Office Action dated Jul. 21, 2008 for European Patent Application No. 02761449.4.
Application to Amend a Complete Specification dated Jul. 24, 2012 directed towards South African Patent Application 2004/1528.
Search Report dated Apr. 26, 2006 for European Patent Application 02792232.7.
Response to Office Action dated Oct. 18, 2010 for European Patent Application 02792232.7.
Response to Office Action dated Jan. 17, 2012 for Korean Patent Application 70007060/2004.
Response to Examiner's First Report dated Aug. 5, 2010 for Australian Patent Application 2007212519.
Office Action dated Feb. 25, 2013 for Japanese Patent Application 2008-553383.
Search Report dated Oct. 6, 2010 for European Patent Application 07752016.1.
Office Action dated Feb. 6, 2013 for Japanese Patent Application 2008-557382.
Response to First Examination Report dated Feb. 8, 2007 for European Patent Application 02749720.
Third-Party Observations dated Sep. 12, 2007 for European Patent Application No. 02749720.5.
Office Action dated Sep. 21, 2011 for Chinese Patent Application 03813556.6.
Response to Office Action dated Sep. 21, 2011 for Chinese Patent Application 03813556.6.
Office Action dated May 16, 2013 for European Patent Application No. 04779826.9.
Office Action dated Nov. 16, 2012 for Chinese Patent Application 201110210275.4.
European Office Action dated Oct. 3, 2013 issued in European Patent Application No. 02792232.7.
Canadian Office Action dated Aug. 23, 2013 issued in Canadian Patent Application No. 2644219.
Japanese Office Action dated Dec. 2, 2013 issued in Divisional Japanese Patent Application No. 2009-236857.
Canadian Office Action dated Oct. 8, 2013 issued in Canadian Patent Application No. 2640203.
Newman, J.T., Nellermoe, M.D., & Carnett, J.L. (1992). "Hydrocortisone phonophoresis: A literature review," Journal of the American Podiatric Medical Association, 82(8). pp. 432-435.
Menon, G.K., Bommannan, D.B., & Elias, P.M. (1993). "High-frequency sonophoresis: Permeation pathways and structural basis for enhanced permeability," Skin Pharmacol, 7. pp. 130-139.
Mitragotri, S., Blankschtein, D., & Langer, R. (1995). "Ultrasound-mediated transdermal protein delivery," Science, 269. pp. 850-853.
Draper, D.O., Castel, J.C., & Castel, D. (1995). "Rate of temperature increase in human muscle during 1 MHz and 3 MHz continuous ultrasound," JOSPT, 22(4). pp. 142-150.
Rougier, A., et al. (1983). "In vivo correlation between stratum corneum reservoir function and percutaneous absorption," The Journal of Investigative Dermatology, 81. pp. 275-278.
Zabel, K. (1999). "Wrinkle removal without the wound," Dermatology Times, 20(6).
Zabel, K. (1999). "Future of laser surgery: Unexplored benefits await," Dermatology Times, 20(6).
Gniadecka, M., et al. (1994) "Ultrasound structure and digital image analysis of the subepidermal low echogenic band in aged human skin: Diurnal changes and interindividual variability," The Journal for Investigative Dermatology, 102(3). pp. 362-365.
Mitragotri, S., et al. (1995). "A mechanistic study of ultrasonically-enhanced transdermal drug delivery," Journal of Pharmaceutical Science, 84(6). pp. 697-706.

Meidan, V.M., et al. (1998). "Low intensity ultrasound as a probe to elucidate the relative follicular contribution to total transdermal absorption," Pharmaceutical Research, 15(1). pp. 85-92.
Mitragotri, S., Blankschtein, D., & Langer, R, (1996). "Transdermal drug delivery using low-frequency sonophoresis," Pharmaceutical Research. 13(3). pp. 441-420.
Mitragotri, S., Blankschtein, D., & Langer, R. (1986). "An explanation for the variation of the sonophoretic transdermal transport enhancement from drug to drug," Journal of Pharmaceutical Science, 86(10). pp. 1190-1192.
Hippius, M., et al. (1998). "In vitro investigations of drug release and penetration-enhancing effect of ultrasound on transmembrane transport of flufenamic acid," International Journal of Clinical Pharmacological,Therapy, and Toxicology, 36(2). pp. 107-111.
Miyazaki, S., et al. (1992). "External control of drug release and penetration. VI. enhancing effect of ultrasound on the transdermal absorption of indomethacin from an ointment in rats," Chemical and Pharmaceutical Bulletin, 40(10). pp. 2826-2830.
Asano, J., et al. (1997). "Effect of pulsed output ultrasound on the transdermal absorption of indomethacin from an ointment in rats," Biological and Pharmaceutical Bulletin, 20(3). pp. 288-291.
Miyazaki, S., et al. (1991). "External control of drug release and penetration: Enhancement of the transdermal absorption of indomethacin by ultrasound irradiation," Journal of Pharmaceutical Pharmacology, 43(2). pp. 115-116.
Bommannan, D., et al. (1992). "Sonophoresis.I. The use of high-frequency ultrasound to enhance transdermal drug delivery," Pharmaceutical Research, 9(4). pp. 559-564.
Tachibana, K., Tachibana, S. (1998). "Application of ultrasound energy as a new drug delivery system," Nippon Rinsho, 56(3). pp. 584-588.
Byl, N.N. (1995). "The use of ultrasound as an enhancer for transcutaneous drug delivery: phonophoresis," Physical Therapy, 75(6). pp. 539-553.
Hikima, T., Hirai, Y., & Tojo, K. (1998), "Effect of ultrasound application on skin metabolism of prednisolone 21-acetate," Pharmaceutical Research, 15(11). pp. 1680-1683.
Yata, N. (1998). "Enhancement of drug absorption by iontophoresis and phonophoresis and clinical application," Nippon Rinsho, 56(3). pp. 608-612.
Kimura, I,F., et al. (1998), "Effects of two ultrasound devices and angles of application on the temperature of tissue phantom," Journal of Orthopedic and Sports Physical Therapy, 27(1). pp. 27-31.
Mikulak, S.A., Vangsness, C.T., & Nimmi, M.E. (1998). "Transdermal delivery and accumulation of indomethacin in subcutaneous tissues in rats," Journal of Pharmaceutical Pharmacology, 50(2). pp. 153-158.
Murakami, T., et al. (1998). "Topical delivery of keloid therapeurtic drug, trailast, by combined use of oleic acid and propylene glycol as a penetration enhancer: Evaluation by skin microdialysis in rats," Journal of Pharmaceutical Pharmacology, 50(1). pp. 49-54.
Stott, P.W., Williams, A.C., & Barry, B.W. (1998). "Transdermal delievery from eutictic systems: Enhanced permeation of a model drug, ibuprofen." Journal of Controlled Release, 50(1-3). pp. 297-308.
Morimoto,Y., & Fujimoto, S. (1985). "Albumin microspheres as drug carriers," Critical Review of Therapeutic Drug Carrier Systems, 2(1). pp. 19-63.
Johnson, M.E., et al. (1996). "Synergistic effects of chemical enhancers and therapeutic ultrasound on transdermal drug delivery," Journal of Pharmaceutical Science, 85(7). pp. 670-679.
Illel, B. (1997). "Formulation for transfollicular drug administration: some recent advances," Critical Review of Therapeutic Drug Carrier Systems, 14(3). pp. 207-219.
Frenkel, V., Kimmel. E., & Iger, Y. (2000). "Ultrasound-facilitated transport of silver chloride (AgCl) particles in fish skin," Journal of Controlled Release, 68(2), pp. 251-161.
Mitragotri, S. (2001), "Effect of therapeutic ultrasound on partition and diffusion coefficients in human stratum corneum," Journal of Controlled Release, 71(1). pp. 23-29.
Tan, H.S., & Pfister, W.R. (1999), "Pressure-sensitive adhesives for transdermal drug delivery systems," PSTT, 2(2). pp. 60-69.

(56) References Cited

OTHER PUBLICATIONS

Tajima, S., & Pinnel, S.R. (1996). "Ascorbic acid preferentially enhances type I and III collagen gene transcription in human skin fibroblasts," Journal of Dermatological Science, 11(3), pp. 250-253.
Castro, D.J., et al. (1987). "Biostimulative effects of Nd: YAG Q-switch dye on normal human fibroblast cultures: Study of a new chemosensitizing agent for the Nd:YAG laser," Laryngoscope, 97(12). pp. 1454-1459.
Omura, T., et al. (1984). "Hemoprotein H-450 identified as a form of cytochrome P-450 having an endogenous ligand at the 6th coordination position of the heme," Journal of Biochemistry, 96(5). pp. 1491-1500.
Hrnjak, M., et al. (1995). "Stimulatory effect of low-power density He—Ne laser radiation on human fibroblasts in vitro," Vojnosanit Pregl, 52(6). pp. 539-546.
Krammer, B., Hubmer, A., & Hermann, A. (1993). "Photodynamic effects on the nuclear envelope of human skin fibroblasts," Journal of Photochemistry and Photobiology, 17(2). pp. 109-114.
Lyons, R.F. et al. (1987). "Biostimulation of wound healing in vivo by a helium—neon laser," Annals of Plastic Surgery, 18(1). pp. 47-50.
Yu, W., Naim, J.O., & Lanzafame, R.J. (1997). "Effects of photostimulation on wound healing in diabetic mice," Lasers in Surgery and Medicine, 20(1). pp. 56-63.
Morrone, G., et al. (1998). "In vitro experimental research of rabbit condrocytes biostimulation with diode laser Ga—Al—As: a preliminary study," Artificial Cells, Blood Substitutes, and Biotechnology, 26(4). pp. 437-439.
Van Breugel, H.H., & Bar, P.R. (1992). "Power density and exposure time of He—Ne laser irradiation are more important than total energy dose in photo-biomodulation of human fibroblasts in vitro," Lasers in Surgery and Medicine. 12(5), pp. 528-537.
Takemura et al,(1998), "Enhanced Interleukin 6 Production by Cultured Fibroblasts from Patients with Systemic Sclerosis in Response to Platelet Derived Growth," The Journal of Rheumatology, pp. 1534-1539.
Czuwara et al. (2001), "Differential regulation of transforming growth factor-β receptors type I and II by platelet-derived growth factor in human dermal fibroblasts," British Journal of Dermatology, 569-575.
Loftsson et al. (1995), "Fatty acids from cod-liver oil as skin penetration enhancers," Die Pharmazie, pp. 271-773.
Stahl et al. (2000), "Carotenoids and carotenoids plus vitamin E protect against unitraviolet light-induced erythema in humans," The American Clinical Journal of Nutrition, pp. 795-798.
Gambichler et al. (2001), "Ultraviolet protection by summer textiles. Ultraviolet transmission measurements verified by termination of the minimal erythema dose with solar simulated radiation," British Journal of Dermatology, pp. 484-489.
Stahl et al. (2001), "Dietary Tomato Pasta Protects against Ultraviolet Light-Induced Erythema in Humans," Biochemical and Molecular Action of Nutrients Research Communication, pp. 1449-1451.
Lee et al. (2000), "Carotenoid Supplementation Reduces Erythema in Human Skin After Simulated Solar Radiation Exposure," Society of Experimental Biology and Medicine, pp. 170-174.
Moy et al. (2000), "Incresed Glycosaminolycans Production in Sclersoing Basal Cell Carcinoma-Derived Fibrolasts and Stimulation of Normal Skin Fibrolast Glycosaminoglycans Production by a Cytokine-Derived from Sclerosing Basal Cell Carcinoma," Dermatolgoic Surgery, pp. 1029-1035.
Takehara, K. (2000), "Grown regulation of skin fibroblasts," Journal of Dermatologial Science pp. 70-74.
Loftsson, T. (1989), "Effect of choline esters and oleic acid on the penetration of acyclovir, estradiol. hydrocortisone, nitroglycerin, retinoic acid and trifluorothymidine across hairless mouse skin in vitro," Acta. Pharm. Nord., pp. 279-286.
Masson et. al, (2000), "Marine lipids for prodrugs, soft compounds and other pharmaceutical applications," Pharmazie, pp. 172-177.
Gross et al. (1978), "Comprehensive compilation of empirical ultrasonic properties of mammalian tissues," Journal of the Acoustical Society of America, pp. 423-457.
Fei et al, (1986), "Ultrasonic backscatter from bovine tissues:Varation with pathology." Journal of the Acoustical Society of America, pp. 166-172.
Fei, D and Shung, K. (1986), "Ultrasonic backscatter from bovine tissues," Journal of the Acoustical Society of America, pp. 871-876.
Chivers, R. and Parry R.(1978), "Ultrasonic velocity and attenuation in mammalian tissues," Journal of the Acoustical Society of America, pp. 940-954.
de Weerd et al. (2002), "Pathways for Energy transfer in the Core Light Harvesting Complexes CP43 and CP 47 of Photosystem II," Biophysical Journal, pp. 1586-1597.
Fluhr et al. (1999), "In-vitro and in-vivo Efficacy of Zinc Acetate against Propionibacteria Alone and in Combination with Erythromycin," Zent. bl. Bakerologie, pp. 445-456.
Lang et al. (2001), "Aminolevulinic acid: pharmacological profile and clinical indication," Expert Opinion Investigative Drugs pp. 1139-1156.
Yakushevska et al. (2001), "Supermolecular organization of photosystem II and its associated light-harvesting antenna in Arabidopsis thalinana," European Journal of Biochemistry, pp. 6020-6028.
Polivka et al, (2002), "Carotenoid Si State in a Recombinant Light-Harvesting Complex of Photosystem II" Biochemistry. pp. 439-450.
Vander Meulen et al. (2002), "Calcium Depletion Modifies the Structure of the Photosystem II O2-Evolving Complex," Biochemistry. pp. 958-966.
Park et al.(2000), "Epidermal Growth (EGF) Antagonizes Transforming Growth Factor (TGF)-β1-Induced Collagen Lattice Contraction by Human Skin Fibrolasts," Biological and Pharmaceutical Bulletin, pp. 1517-1520.
Diffey et al. (2000), "In vitro assessment of the broad-spectrum ultrviolet protection of sunscreen products." Journal of the American Academy of Dermatology, pp. 1024-1035.
Zhu et al. (1997), "Photo-Irradiation Improved Functional Preservation of the Isolated Rat Heart," Lasers in Surgery and Medicine, pp. 332-339.
Yu et al. (1997), "Improvement of Host Response to Sepsis by Photobiomodulation," Lasers in Surgery and Medicine, pp. 262-268.
Shapiro, J and Price, V. (1998), "Hair Regrowth: Therapeutic Agents," Dermatologic Therapy, pp. 341-356.
El Sayed, S and Dyson, M. (1990), "Comparision of the Effect of Multiwavelength Light Produced by a Cluster of Semiconductor Diodes and of Each Individual Diode on mast Cell Number and Degranulation in Intact and Injured Skin," Lasers in Surgery and Medicine, pp. 559-568.
Huang et al. (2002), "Two-Photon Fluorescence Spectroscopy and Microscopy of NAD(P)H and Flavoprotein," Biophysical Journal, pp. 2811-2825.
Yamazaki et al. (1992), "Slecetive Chemical Modification of Amino Acid Residues in the Flavin Adrenie Dinucleotide Binding Site of Nadph-Ferredoxin Reductase," Internternational Journal of Biochemistry, pp. 223-228.
Andersson et al. (1998), "Autofluoresence of living cells," Journal of Microscopy, pp. 1-7.
Chen et al (2002), "New Technology for Deep Light Distribution in Tissue for Phototherapy." The Cancer Journal, pp. 154-163.
Baena-Gonzalez et al. (2001), "Cloroplast Transcription at Different Light Intensities, Glutathione-Mediated Phosphorylation of the Major RNA Polymerase Involved in Redox-Regulated Organellar Gene Expression," Plant Physiology, pp. 1044-1052.
Cheng, K. and Goldman, R. (1998), "Electronic Field and Proliferation in a Dermal Wound Moder Cell Cycle Kinetics," Bioelectromagnetics, 68-74.
Stough et al. (2002), "Finasteride improves male pattern hair loss in a randomized study in indentical twins," European Journal of Dermatology, pp. 32-37.
Todd et al. (2001), "Electrical Stimulation of Transforming Growth Factor-β1 Secretion by Human Dermal Fibroblasts and the U937 Human Monocyctic Cell Line," pp. 693-701.
Unholzer, A and Korting, H. (2002), "High Frequency Ultrasound in the Evaluation of Pharmacological Effects on the Skin," Skin Pharmacology and Applied Skin Physiology, pp. 71-84.

(56) References Cited

OTHER PUBLICATIONS

Pelle et al. (2002), "Cigareete Smoke-Inducted Lipid Peroxidation in Human Skin and its Inhibition by Topically Applied Antioxidants," Skin Pharmacology and Applied Skin Physiology, pp. 63-68.
Garbaers et al. (2001), "Mossbauer study of iron centers in DVD2/Cyt b 559 complexes isolated from photostem II of spinach," European Biophysics Journal, pp. 485-493.
O.Ishiawa et al. (1997), "Morphological and biochemical analyses on fibroblasts and self-produced collagens in a novel three dimensional culture," British Journal of Dermatology, pp. 6-11.
Harmon, C. and Nevins, T. (1994), Biophasic Effect of 1, 25-Dihyoxyvitamin D on Human Hair Follicle Growth and Hair Fiber Production in Whole Organ Cultures, Journal of Investigative Dermatology pp. 318-322.
Reiss, S. (2002), "Photodynamic Therapy: Reaching Beyond Cancer," Biophotonics International Journal, pp. 48-54.
Lahjomri et al. (1997), "Pulsed Photoacoustic Study of the Diffusion of Chromophores in Human Skin," Photochemistry and Photobiology, pp. 292-302.
Agramonte, A. (2001). "The Inside History of a Great Medical Discovery," Military Medicine, pp. 66-78.
Tsukahara et al. (2001), "Dirunal variation affects age-related profile in skin thickness," Journal of Cosmetic Science, pp. 391-397.
Ernst, E. and Huntley, A. (2000), "Tea Tree Oil: A system Review of Randomized Clinical Trials," Research in Complementary Medicine, pp. 17-20.
Masuda et al. (2002), "Biosynthesis and distribution of chlorophyll among the photosystems during recovery of the green alga Dunaliella salina from irradiance stress," Plant Physiology, pp. 603-614. (Abstract).
Joet et al. (2002), "Cyclic Electron Flow around Photosystem I in C(C) Plants. In Vivo Control byu the Redox State of Chloroplasts and Involvement of the NADH-Dehydroense Complex," pp. 760-769. (Abstract).
Christen et al. (2000), "Delayed Fluorescence emitted from light harvesting complex II and photosystem II of higher plants in the 100 ns-5 mircos time domain," FEBS Lett., pp. 103-106. (Abstract).
de Wijn et al. (2001), "Secondary stabilization reactions and proton-coupled electron transport in photosytem II investigated by electroluminescence and fluorescence spectroscopy," Biochemistry, pp. 5821-5834.
Hou et al. (2001), "Thermodynamics of electron transfer in oxygenic photosystem reaction centers; a pulsed photoacoustic study of electron transfer in photosystem I reveals a similarity to bacertial reaction centers in both volume change and entropy," Biochemistry, pp. 7109-7016.
Non-Final Rejection dated Sep. 22, 2009 for U.S. Appl. No. 11/116,434.
Response to Final Office Action dated Jan. 5, 2009 for U.S. Appl. No. 11/116,434.
Final Rejection dated Jan. 5, 2009 for U.S. Appl. No. 11/116,434.
Amendment to Non-Final Rejection dated Feb. 20, 2008 for U.S. Appl. No. 11/116,434.
Non-Final Rejection dated Feb. 20, 2008 for U.S. Appl. No. 11/116,434.
Amendment to Final Office Action dated Jun. 29, 2007 for U.S. Appl. No. 11/116,434.
Final Rejection dated Jun. 29, 2007 for U.S. Appl. No. 11/116,434.
Amendment to Non-Final Rejection dated Jan. 9, 2007 for U.S. Appl. No. 11/116,434.
Non-Final Rejection dated Jan. 9, 2007 for U.S. Appl. No. 11/116,434.
Amendment to Miscellaneous Action regarding Drawing Inconsistency dated Aug. 24, 2004 for U.S. Appl. No. 09/876,157.
Miscellaneous Action regarding Drawing Inconsistency dated Aug. 24, 2005 for U.S. Appl. No. 09/876,157.
Amendment to Non-Final Rejection dated Apr. 8, 2004 for U.S. Appl. No. 09/876,157.
Non-Final Rejection dated Apr. 8, 2004 for U.S. Appl. No. 09/876,157.
Response to Restriction Requirement dated Jul. 22, 2003 for U.S. Appl. No. 09/876,157.
Requirement for Restriction/Election dated Jul. 22, 2003 for U.S. Appl. No. 09/876,157.
Preliminary Amendment filed Jan. 7, 2002 for U.S. Appl. No. 09/876,157.
Amendment to Final Office Action dated Jan. 25, 2008 for U.S. Appl. No. 11/783,538.
Final Rejection dated Jan. 25, 2008 for U.S. Appl. No. 11/783,538.
Amendment to Non-Final Rejection dated Aug. 22, 2007 for U.S. Appl. No. 11/783,538.
Non-Final Rejection dated Aug. 22, 2007 for U.S. Appl. No. 11/783,538.
Non-Final Rejection dated Dec. 30, 2005 for U.S. Appl. No. 09/819,082.
Preliminary Amendment filed Feb. 15, 2001 for U.S. Appl. No. 09/819,082.
Amendment After Notice of Allowance filed Aug. 1, 2008 for U.S. Appl. No. 09/819,083.
Amendment to Final Office Action dated Jan. 24, 2008 for U.S. Appl. No. 09/819,083.
Final Rejection dated Jan. 24, 2008 for U.S. Appl. No. 09/819,083.
Amendment to Non-Final Rejection dated May 15, 2007 for U.S. Appl. No. 09/819,083.
Non-Final Rejection dated May 15, 2007 for U.S. Appl. No. 09/819,083.
Amendment to Final Office Action dated Dec. 22, 2006 for U.S. Appl. No. 09/819,083.
Final Rejection dated Dec. 22, 2006 for U.S. Appl. No. 09/819,083.
Amendment to Non-Final Rejection dated Mar. 24, 2006 for U.S. Appl. No. 09/819,083.
Non-Final Rejection dated Mar. 24, 2006 for U.S. Appl. No. 09/819,083.
Advisory Action dated Dec. 1, 2005 for U.S. Appl. No. 09/819,083.
Amendment to Final Office Action dated Sep. 1, 2005 for U.S. Appl. No. 09/819,083.
Final Rejection dated Sep. 1, 2005 for U.S. Appl. No. 09/819,083.
Amendment to Non-Final Rejection dated Dec. 15, 2004 for U.S. Appl. No. 09/819,083.
Non-Final Rejection dated Dec. 15, 2004 for U.S. Appl. No. 09/819,083.
Amendment to Non-Final Rejection dated Jan. 14, 2004 for U.S. Appl. No. 09/819,083.
Non-Final Rejection dated Jan. 14, 2004 for U.S. Appl. No. 09/819,083.
Final Office Action dated Dec. 9, 2011 for U.S. Appl. No. 12/753,207.
Response to Final Office Action dated Dec. 9, 2011 for U.S. Appl. No. 12/753,207.
Notice of Restriction dated Mar. 29, 2006 for U.S. Appl. No. 10/665,390.
Response to Restriction dated Mar. 29, 2006 for U.S. Appl. No. 10/665,390.
Non Final Rejection dated Aug. 21, 2006 for U.S. Appl. No. 10/665,390.
Non Final Rejection dated Jan. 5, 2006 for U.S. Appl. No. 10/903,483.
Amendment to Non-Final Rejection dated Jan. 5, 2006 for U.S. Appl. No. 10/903,483.
Non Final Rejection dated Sep. 25, 2006 for U.S. Appl. No. 10/903,483.
Amendment to Non-Final Rejection dated Sep. 25, 2006 for U.S. Appl. No. 10/903,483.
Non Final Rejection dated May 22, 2008 for U.S. Appl. No. 10/903,483.
Non Final Rejection dated Jul. 18, 2007 for U.S. Appl. No. 11/205,316.
Amendment to Non-Final Rejection dated Jul. 18, 2007 for U.S. Appl. No. 11/205,316.
Final Rejection dated Jun. 9, 2008 for U.S. Appl. No. 11/205,316.
Non Final Rejection dated Oct. 19, 2007 for U.S. Appl. No. 11/272,042.

(56) References Cited

OTHER PUBLICATIONS

Amendment to Non-Final Rejection dated Oct. 19, 2007 for U.S. Appl. No. 11/272,042.
Final Rejection dated Jun. 6, 2008 for U.S. Appl. No. 11/272,042.
Non-Final Rejection dated Jun. 8, 2010 for U.S. Appl. No. 12/583,562.
Amendment to Non-Final Rejection dated Jun. 8, 2010 for U.S. Appl. No. 12/583,562.
Official Notification dated Dec. 3, 2008 for Israeli Patent Application No. 171311.
Official Notification dated Nov. 19, 2009 for Israeli Patent Application No. 171311.
Response to Official Notification dated Nov. 19, 2009 for Israeli Patent Application No. 171311.
First Office Action dated Mar. 10, 2006 for Chinese Patent Application No. 200480012575.X.
Response to First Office Action dated Mar. 10, 2006 for Chinese Patent Application No. 200480012575.X.
Second Office Action dated Nov. 2, 2007 for Chinese Patent Application No. 200480012575.X.
Notice of Reexamination dated Jul. 27, 2010 for Chinese Patent Application 200480012575.X.
Response to Notice of Reexamination dated Jul. 27, 2010 for Chinese Patent Application No. 200480012575A.
Official Notification regarding clarification of claims dated Sep. 19, 2002 for PCT Patent Application No. PCT/US02/26627.
Request for Rectification of Obvious Errors in the International Patent Application and Submission of Request to Record Change of Agent's Address dated Sep. 27, 2002 for PCT Patent Application No. PCT/US02/26627.
International Search Report dated May 16, 2003 for PCT Patent Application No. PCT/US02/26627.
Written Opinion dated Feb. 5, 2004 for PCT Patent Application No. PCT/US02/26627.
International Search Report dated May 8, 2003 for PCT Patent Application No. PCT/US02/35839.
International Preliminary Examination Report dated Oct. 7, 2003 for PCT Patent Application No. PCT/US02/35839.
First Statement of Proposed Amendments dated Oct. 27, 2005 for Australian Patent Application No. 2002326716.
Examiner's Report dated Mar. 22, 2007 for Australian Patent Application No. 2002326716.
Office Action dated Aug. 2, 2006 for Canadian Patent Application No. 2457590.
Response to Office Action dated Aug. 2, 2006 for Canadian Patent Application No. 2457590.
Office Action dated Apr. 30, 2007 for Canadian Patent Application No. 2457590.
Response and Amendment to Office Action dated Apr. 30, 2007 for Canadian Patent Application No. 2457590.
Office Action dated Jan. 31, 2008 for Canadian Patent Application No. 2457590.
Request for Reinstatement for Failure to Respond to Office Action dated Jan. 31, 2008 for Canadian Patent Application No. 2457590.
Office Action dated Oct. 2, 2009 for Canadian Patent Application No. 2457590.
Response to Office Action dated Oct. 2, 2009 for Canadian Patent Application No. 2457590.
Office Action dated Dec. 30, 2010 in Canadian Patent Application No. 2,457,590.
Office Action dated May 6, 2010 in Canadian Patent Application No. 2,457,590.
Response to Office Action dated May 6, 2010 in Canadian Patent Application 2,457,590.
Office Action dated Aug. 25, 2006 for European Patent Application No. 02761449.4-1216.
Response to Office Action dated Aug. 25, 2006 for European Patent Application No. 02761449.4-1216.
Office Action dated Jul. 31, 2007 for European Patent Application No. 02761449.4-1216.
Response to Office Action dated Jul. 31, 2007 for European Patent Application No. 02761449.4-1216.
Communication pursuant to Article 94(3) EPC issued Sep. 18, 2014, in Application No. 02 792 232.7-1458.
Office Action mailed Oct. 6, 2014, in CA 2,640,203.
Office Action mailed Dec. 4, 2014, in CA 2,664,219.
Differently Localized Experiemental Granulomas, Acta Chirurgiae Plasticae 19, pp. 148-156.
James Ferry et al. (1990) "Relationship Between Contact Time of Applied Dose and Percutaneous Absorption of Minoxidil from a Topical Solution," Journal of Pharmaceutical Sciences 79(6).
Jean-Paul Ortonne (1989) "Psoralen Therapy in Vitiligo," *Clinics in Dermatology* 7(2).
John Murphy (1995) "From Submarines to Rehab: New Developments in Ultrasound," *Advance Rehabilitation*.
Joseph T. Newman et al. (Aug. 1992) "Hydrocortisone Phonophoresis, A Literature Review," *Journal of the American Podiatric Medical Association* 82(8), pp. 432-435.
Jui-Chen Tsai et al. (1992) "Drug and Vehicle Deposition from Topical Applications: Use of in Vitro Mass Balance Technique with Minoxidil Solutions," *Journal of Pharmaceutical Sciences* 81(8).
K. Gierlich et al. "Physikalische Medizin and Rehabilitation Heft 9/68" The Combined Application of Ultrasound and Stimulation Currents, Reprint from the Journal, Sep. 1968.
Kamel Egbaria et al. (1992) "Adsorption of Fluorescein Dyes on Albumin Microspheres," *Pharmaceutical Research* 9, pp. 629-635.
Katsuro Tachibana (1992) "Transdermal Delivery of Insulin to Allosxan-Diabetic Rabbits by Ultrasound Exposure," Pharmaceutical Research 9(7).
Katsuro Tachibana et al. (1993) "Use of Ultrasound to Enhance the Local Anesthetic Effect of Topically Applied Aqueous Lidocaine," *Anesthesiology* 78(6), pp. 1091-1096.
Kemmatp et al., (May 2001) "What Color is my LED?" *Photonics Spectra*.
Labbe et al., (1990) "Laser Photobioactivation Mechanisms: in Vitro Studies Using Ascorbic Acid Uptake and Hydroxyproline Formation as Biochemical Markers of Irradiation Response" *Lasers in Surgery and Medicine* 10, pp. 201-207.
Linda Lieb et al. (1992) "Topical Delivery Enhancement with Multilamellar Liposomes into Pilosebaceous Units: I. In Vitro Evaluation Using Fluorescent Techniques with the Hamster Ear Model," *The Journal of Investigative Dermatology* 99(1).
Lingna Li et al. (1992) "Product-Delivering Liposomes Specifically Target Hair Follicles in Histocultured Intact Skin," *In Vitro Cell Dev. Biol.* 28A, pp. 679-681.
Loevschall, (1994) "Effect of Low Level Diode Laser Irradiation of Human Oral Mucosa Fibroblasts in Vitro" *Lasers in Surgery and Medicine* 14, pp. 347-354.
Luther Kloth et al. (1996) "Promotion of Wound Healing with Electrical Stimulation," *The Journal for Prevention and Healing Advances* 9(5).
M. Dyson "The Effect of Ultrasound on the Rate of Wound Healing and the Quality of Scar Tissue," Department of Anatomy, Guy's Hospital Medical School, London, England pp. 110-122 , 1981.
M. F. Coldman et al. (1969) "Enhancement of Percutaneous Adsorption by the Use of Volatile: Nonvolatile Systems as Vehicles," *Journal of Pharmaceutical Sciences* 58(9).
M. Hrnjak et al. (Nov. 1995) "Stimulatory Effect of Low-Power Density He-Ne Radiation on Human Fibroblast in Vitro," *Vojnosanit Pregl.* 52(6), pp. 539-546.
M. J. Callam et al. (Jul. 1987) "A Controlled Trial of Weekly Ultrasound Therapy in Chronic Leg Ulceration," *The Lancet*, pp. 204-206.
M. Pogrel et al. (1997) "Efects of Low-Energy Gallium-Aluminum-Arsenide Laser Irradiation on Cultured Fibroblasts and Keratincytes," *Lasers in Surgery and Medicine* 20, pp. 426-432.
M. Suzuki et al. (1978) "Autoradiographic Study on Percutaneous Absorption of Several Oils Useful for Cosmetics," *J. Soc. Cosmet. Chem.* 29, pp. 265-282.
Mary Dyson (Sep. 1982) "Stimulation of Tissue Repair by Therapeutic Ultrasound," *Infections in Surgery*.

(56) References Cited

OTHER PUBLICATIONS

Mary Dyson et al. (Apr. 1978) "Stimulation of Tissue Repair by Ultrasound: A Survey of the Mechanisms Involved," *Physiotherapy* 64(4), pp. 105-108.

McDaniel, (May 2001) "Nonablative Skin Rejuvenation-The Wave of Future" *Cosmetic Surgery Times Narrow-Band, Blue Light Source Clinical Application Notes 9(1).*.

Sheldon Pinnell (1985) "Regulation of Collagen Biosynthesis of Ascorbic Acid: A Review,"The Yale Journal of Biology and Medicine 58, pp. 553-559.

Shingo Tajima et al. (1996) "Ascorbic Acid Preferentially Enhances Type I and III Collagen Gene Transcription in Human Skin Fibroblasts," *J. Dermatol Sci.* 11(3), pp. 250-253.

Skinner et al., (1996) "A Preliminary Study of the Effects of Laser Radiation on Collagen Metabolism in Cell Culture" *Australian Dental Journal* 41(3), pp. 188-192.

Sommer et al., (2001) "Biostimulatory Windows in Low-Intensity Laser Activation: Lasers, Scanners and NASA's Light Emitting Diode Array System" *Journal of Clinical Laser Medicine & Surgery* 19(1), pp. 29-33.

Sroka et al., (1999)"Effects on the Mitosis of Normal and Tumor Cells Induced by Light Treatment of Different Wavelengths" *Lasers in Surgery and Medicine* 25, pp. 263-271.

Stephen Guffey et al. (1991) "More than a Thermal Modality: Ultrasound," *Advance Rehabilitation*.

Sumian et al. A New Method to Improve Penetration Depth of Dyes into the Follicular Duct: Potential Application for Laser Hair Removal, Aug. 1999.

T. B. Melo (1987) "Uptake of Protoporphyrin and Violet Light Photodestruction of *Propionibacterium acnes*," *Journal of Biosciences* 42(1-2), pp. 123-128.

T. Omura (Nov. 1984) "Hemoprotein H-450 Identified as a Form of Cytochrome P-450 Having an Endogenous Ligand at the 6th Coordination Position of the Heme," *J. Biochem* 96(5), pp. 1491-1500.

The International Congress of Esthetics, Oct. 25-27, 1997, Convention Program.

Thomas Franz (Feb. 1985) "Percutaneous Absorption of Minoxidil in Man," *Arch Dermatol* 121.

V. Drastichova et al. (1973) "Strengthening of Sutured Skin Wound with Ultrasound in Experiments on Animals," *Acta Chirurgiae Plasticae* 15, pp. pp. 114-119.

V. Srinivasan et al. (1989) "Transdermal Iontophoretic Drug Delivery: Mechanistic Anaylsis and Application to Polypeptide Delivery," *Journal of Pharmaceutical Sciences* 78(5).

V. Srinivasan et al. (1990) "Ionotphoresis of Polypeptides: Effect of Ethanol Pretreatment of Human Skin," *Journal of Pharmaceutical Sciences* 79(7).

Van Breugel et al. (1992) "Power Density and Exposure Time of He-Ne Laser Irradiation are More Important Than Total Energy Dose in Photo-Biomodulation of Human Fibroblasts in Vitro" *Lasers in Surgery and Medicine* 12, pp. 528-537.

Vreman et al., (1998) "Light-Emitting Diodes: a Novel Light Source for Phototherapy" 44, pp. 5.

W. Harvey et al. (1975) "The Stimulation of Protein Synthesis in Human Fibroblasts by Therapeutic Ultrasound," *Rheumatology and Rehabilitation* 14, 237.

W. Westerhof et al. (1997) "*Treatment of Vitiligo with UV-B Radiation v. Topical Psoralen Plus UV-A,*" *Arch. Dermatol.* 133, pp. 1525-1528.

W. Yu et al. (1997) "Effects of Photostimulation on Wound Healing in Diabetic Mice," *Lasers Sug. Med.* 20(1), pp. 56-63.

Webb, et al. (1998) "Stimulatory Effect of 660 nm Low Level Laser Energy on Hypertrophic Scar-derived Fibroblasts: Possible Mechanisms for Increase in Cell Counts" *Lasers in Surgery and Medicine* 22, pp. 294-301.

Wei Yu et al. (1997) "Improvement of Host Response to Sepsis by Photobiomodulation" *Lasers in Surgery and Medicine* 21, pp. 262-268.

Wolfgang Ritschel et al. (1989) "Percutaneous Absorption of Coumarin, Griseofulvin and Propranolol Across Human Scalp and Abdominal Skin," *Meth and Find Exp Clin Pharmacol.* 11(10), pp. 643-646.

Z. Joachims et al. (1987) "Noise-Induced Hearing Loss in Humans as a Function of Serum Mg Concentration," *Mag-Bull*, pp. 130-131.

Zelickson et al. (1999) "Pulsed Dye Laser Therapy for Sun Damaged Skin," *Lasers in Surgery and Medicine* 25, pp. 229-236.

\* cited by examiner

LOW INTENSITY LIGHT THERAPY FOR TREATMENT OF RETINAL, MACULAR, AND VISUAL PATHWAY DISORDERS

This application is a continuation-in-part of copending U.S. application Ser. No. 11/119,378, filed May 2, 2005, which is a divisional of U.S. Pat. No. 6,887,260 filed Aug. 22, 2001, which is a continuation-in-part of U.S. Pat. No. 6,283,956, filed Nov. 30, 1998.

FIELD OF THE INVENTION

The present invention generally relates to systems and methods for treating visual pathway disorders or dysfunctions resulting from, among other things, disease, acute and chronic environmental factors or injuries, and aging. Illustratively, the invention may employ low-intensity light therapy to photomodulate retinal pigment epithelial cells to alleviate or reverse or repair disorders including or arising from age-related macular degeneration, diabetic retinopathy, hereditary optic neuropathy, disorders of the visual pathway (optic nerve, retina, retinal artery, cornea, etc.), cataracts, and other disorders of the human vision apparatus.

BACKGROUND OF THE INVENTION

Low-level light therapy has become an alternative to many types of treatments previously thought to be best-effected by high-energy methods, such as those using lasers, flashlamps, etc. For example, photodynamic therapies, lasers and other high-energy light treatments were believe to be an effective treatment method to reduce or eliminate the skin disorders associated with the activity of sebaceous oil glands, hair growth, wound healing and treating dermatological conditions, such as the reduction of wrinkles and fine lines, scar removal, etc.

Those skilled in the art speculate that oxidative stress and mitochondrial function or dysfunction are involved in the pathogenesis of numerous retinal, visual pathway, and optic nerve diseases, including age-related macular degeneration, diabetic retinopathy, as well as Leber's hereditary optic neuropathy and many other disorders of the visual pathway. Decreasing mitochondrial function has also been asserted to be related to methanol intoxication. It has been noted that Methanol intoxication produces toxic injury to the retina and optic nerve, frequently resulting in blindness. A toxic exposure to methanol may result in the development of formic acidosis, metabolic acidosis, visual toxicity, coma, and, in extreme cases, death. Visual impairment may develop between 18 and 48 hours after methanol ingestion. Symptoms may range from misty or blurred vision to complete blindness. Both acute and chronic methanol exposure have been shown to produce retinal dysfunction and optic nerve damage clinically. Other chemical agents can produce similar disorders Formic acid is a toxic metabolite responsible for the retinal and optic nerve toxicity produced in methanol intoxication. Formic acid is a known mitochondrial toxin that may inhibit cytochrome c oxidase, the terminal enzyme of the mitochondrial electron transport chain of all eukaryotes. Cytochrome oxidase is an important energy-generating enzyme critical for the proper functioning of almost all cells, especially those of highly oxidative organs, including the retina and brain.

Photomodulation using narrowband, multichromatic light using low-energy sources, such as light-emitting diode (LED) arrays have been shown to accelerate wound healing, improve recovery from ischemic injury in the heart, and improve many skin-related disorders as illustrated in U.S. Pat. No. 6,663,659 (McDaniel) which is hereby incorporated by reference in its entirety. Further, at the cellular level, the use of light at low energy fluences may generate significant biological effects, including cellular proliferation, collagen synthesis, and the release of growth factors from cells, alteration of gene expression and even repair of DNA damage.

Studies have demonstrated that LED photomodulation at 660 nm (<4 J/cm$^2$) may stimulate cellular proliferation in cultured cells and significantly improves wound healing. However, despite widespread clinical application, the mechanisms responsible for the beneficial actions of photomodulation are not fully understood. A possible explanation for this may be that mitochondrial cytochromes could act as photoacceptors for light energy; and, further, other receptors may act as mediators for the biological effects of this light.

SUMMARY OF THE INVENTION

The method of this invention may include exposing target cells in a visual pathway to one or more sources of light having at least one dominant emissive wavelength between about 300 nm and about 1600 nm; and delivering an energy fluence to the target cells of less than about 10 J/cm$^2$. The light source, or sources, may each emit a dominant emissive wavelength of from about 400 nm to about 900 nm. The energy fluence delivered to the target cells may be from about 1 nanojoule/cm$^2$ to about 1 joule/cm$^2$.

Suitable light sources according to the present invention may be selected from a light emitting diode, a laser, a laser diode, a dye laser, metal halide lamps, a flashlamp, a mechanically filtered fluorescent light source, a mechanically filtered incandescent or filamentous light source, or combinations thereof. When multiple light sources are used, they may be of the same or different types.

In one embodiment of the invention, two light sources can be used. The first source of light emits at a dominant emissive wavelength of about 590 nm and the second source of light emits light at a dominant emissive wavelength of about 870 nm. The light sources may deliver energy fluence, as received at the target cells, of from about from about 1 nanojoule/cm$^2$ to about 1 J/cm$^2$; from about 0.05 J/cm$^2$ to about 0.15 J/cm$^2$, or simply about 0.10 J/cm$^2$.

The light source or sources maybe be operated in a pulsed or in a continuous wave manner. For example, in pulsed mode, the light source or sources emit light according to a pulse code. One pulse code might be 250/100/100—or 250 milliseconds "on", 100 milliseconds "off", and the pulses are repeated 100 times.

In other embodiments of the invention, the light sources may be applied to reduce or eliminate oxidative stress, treat inner ear disorders, treat migraine headaches, reduce or eliminate cellulite, or treat the variety of cell disorders and dysfunctions described hereinafter.

BRIEF DESCRIPTION OF THE DRAWINGS

FIG. 2 illustrates various photomodulatory processes and the state of the cell which each process may be applicable to.

Figure 1:
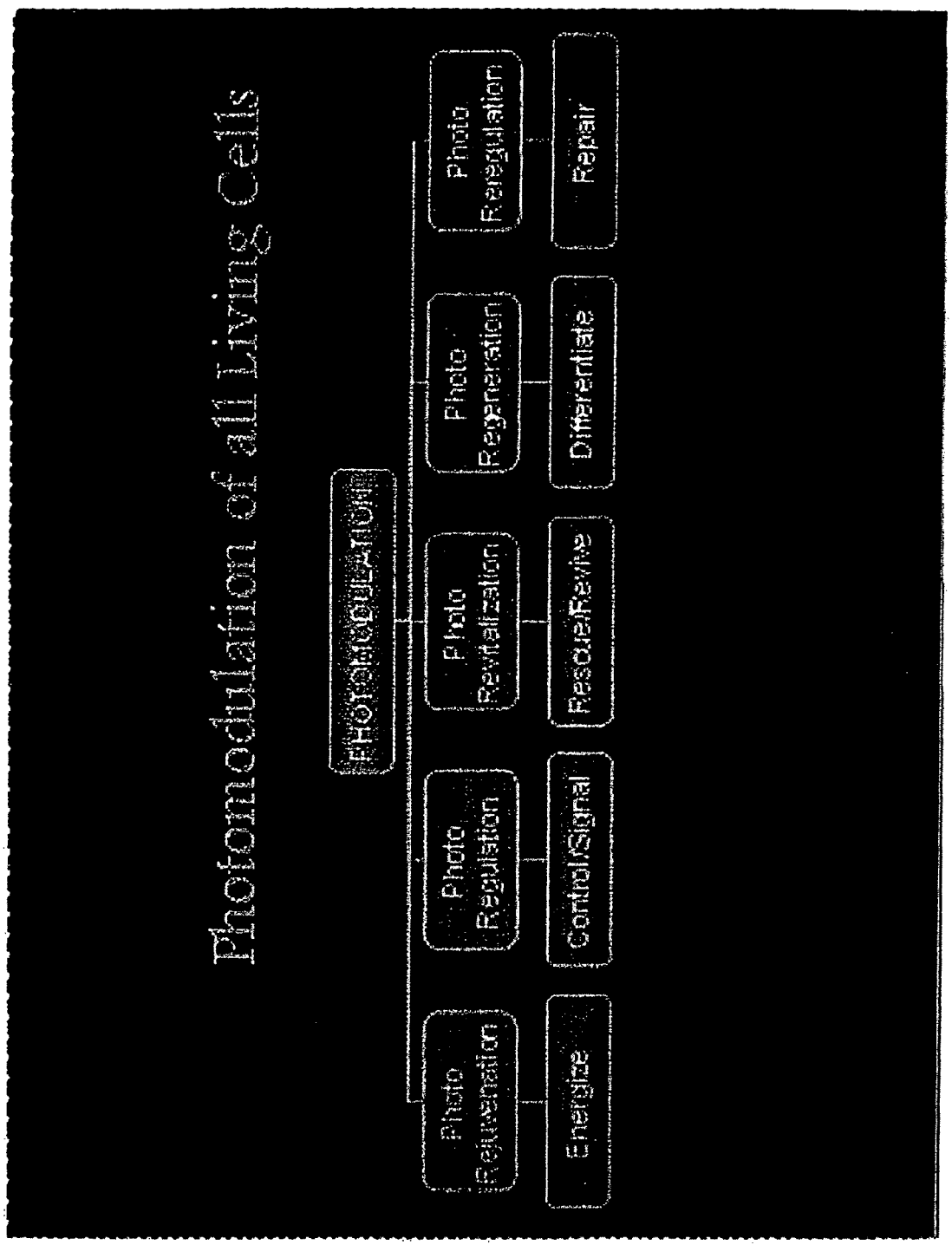
FIG. 1 is a chart illustrating various photomodulatory processes and their anticipated effect on cells.

A detailed description of a preferred embodiment of the present invention will be made with reference to the accompanying drawings.

DETAILED DESCRIPTION OF THE PREFERRED EMBODIMENTS

The following detailed description is of the best presently contemplated mode of carrying out the invention. This description is not to be taken in a limiting sense, but is made merely for the purpose of illustrating the general principles of the invention. The scope of the invention is defined solely by the appended claims.

In a preferred embodiment, the present invention is directed to a process for treating vision and eye disorders. Specifically, the treatment may be used to photomodulate retinal pigment epithelial cells, and other portions of the visual pathway, to alleviate or reverse disorders including or arising from age-related macular degeneration, diabetic retinopathy, hereditary optic neuropathy, disorders of the visual pathway (optic nerve, retina, retinal artery, cornea, etc.), cataracts, and other disorders of the human vision apparatus.

The treatment of retinal pigment epithelial cells (RPE) can reduce or reverse the effects of, for example, the damage cause to retinal cells by ultraviolet light, blue light, and oxidative stress caused by free radicals during exposure to stimuli or environmental factors that cause oxidative stress, free radicals, injury, or inflammation, resulting in stress or dysfunction to cells. Such damage may lead to macular degeneration, an affliction with affects about 10% of adults and is a leading cause of blindness in developed countries.

Present treatments show minimal effectiveness at combating macular degeneration, although the use of antioxidant vitamins has shown promise. Other current therapies attempt to decrease the activity of gene expression which stimulates blood vessel growth (e.g. VEGF). The present invention, however, has been unexpectedly found to produce significant advantages and superior results in comparison to prior art method, particularly with respect to controlling and reducing cell damage or death produced by free radicals, thereby providing a significant anti-oxidant-like effect without the use of pharmaceuticals. Another effect has been to reduce expression of activity of the VEGF gene.

In an illustrative embodiment of the invention, macular degeneration can be reduced, and possibly even reversed, by the treatment of afflicted cells with light therapy. That therapy is generally described as low-intensity light therapy, or LILT. The most common source of light used in such therapy is a narrowband source of multichromatic radiation, such as a light emitting diode. Other forms of light can be used, however, such as organic LEDs, flashlamps, lasers, laser diodes, dye lasers, filamentous and fluorescent sources, etc. The selection of the light source may be determined by the desired treatment. If, for example, the treatment of the brain is desired, a high energy light source, such as a flashlamp, may be used, as it will require a large energy fluence at the light source to penetrate through the skull to deliver a low energy fluence to the cell or target tissue receiving treatment. As well, unless otherwise specified hereinafter, the energy fluences recited herein refer to the amount of energy (watts×time) perceived by the targeted tissue, cell, or other biological structure being treated.

By way of example, loud percussive noises are known to cause temporary hearing loss (which may become permanent after prolonged exposure). Characteristic of this is oxidative stress caused by free radical release in certain cells within the auditory or hearing pathways. A potential application of the present technology in connection with a device such as a personal media device (mp3 player, for example). Prolonged use of such a device at a high listening volume may cause temporary, leading to permanent, hearing loss.

Typically, a personal media player has "ear buds" or small headphones. By fitting the ends of such headphones with LEDs able to emit an energy fluence capable of administering an effective dosage of light through the ear canal and eardrum to reach cells subject to inflammation and oxidative stress, personal devices such as MP3 players could be used without the risk of hearing degradation. Such a use of the present invention may be expanded to occupation hearing protection devices and other apparatus for protecting hearing when a subject is exposed to high sound volumes for periods of time. Such a device could also be used to treat hearing loss from other causes, as well as tinnitus (ringing in the ears) and balance disorders and infections.

Another example might include the use of low intensity light, in place of or in conjunction with, anti-oxidant drugs to reduce temporary hearing loss or ringing in the ears resulting from prolonged exposure to loud sound. As it has been surmised that the "ringing" or temporary hearing loss is due to oxidative stress in the hair cells or auditory nerve, delivering a low energy fluence across the eardrum, although not wishing to be bound by theory, may further reduce or eliminate such oxidative stress by neutralizing free radicals produced when the hair cells or auditory nerve is exposed to high intensity sound waves or other environmental injuries or exposure to toxic agents such as those used in chemotherapy. Photomodulation may be used to alter gene expression to reverse, repair or counteract effects of cell damage. In addition, certain pharmaceutical treatments are known to cause hearing degradation in patients. The present invention may be applied to reduce or reverse or protect from the effects of such medications.

Other medical treatment that may be provided by the present invention can include the application of light through the cribiform plate to achieve a small energy fluence direct to the brain; delivery of light via fiber optics or via an endoscope to deliver an energy fluence to internal tissue and organs or coronary arteries; and delivery of light directly to mouth and gums to treat various dental and periodontal conditions. Light may also be administered to the nasal passages, or into the sinuses, externally or internally. As well, the thyroid gland (for various thyroid disorders), the thymus gland for regulating immune functions, etc. may be treated directly or through the skin.

In a preferred embodiment of the present invention, one would expose any component of a patient's visual system to the therapeutic effects of the light treatment described above. By "visual system" we mean to include, but not be limited to, the cornea, iris, lens, retina, optic nerve, optic chiasm, lateral geniculate nucleus, vitreous, retinal artery, superior colliculus, pretectal nucleic, the accessory optic system, the oculomotor system, pulvinar, optic radiations, visual cortex, and associational visual cortical areas.

Exposure of the visual system may occur by treating with light directed into the eyes, thus irradiating the cornea, lens, iris, retina and optic nerve head. Alternatively, the device can be oriented so that the light is directed through the back of the skull or irradiating the visual cortex or through the sides or top of the head thus irradiating the other components of the visual system or brain. In this instance, however, a much higher energy fluence must be emitted by the source to deliver a very low energy fluence to the target tissue, due to the amount of skin, bone, etc. that the light must pass through prior to reaching the target, thereby permitting the target to receive a clinically desirable dosage of light, according to the parameter given herein for photomodulatory treatment. Alternatively, delivery of the light could be more 'direct', by applying it under the skin or directly through the skull bones into the brain (for example, to slow or stop the growth of benign or malignant tumors).

In order to observe and/or quantify the restoration or protection of visual function, any conventional way that assesses visual function can be employed:

Therapeutic endpoints for treatment of corneal abrasion would include absence of fluorescein staining of the cornea. For retinal injury or disease, therapeutic endpoint measurement would include: (1) fundoscopy or fundus photography which is an assessment of the appearance of the fundus or back of the eye, (note that the retina and optic nerve may be observed by using special lenses); (2) Optical coherence tomography which measures the thickness (cross sectional architecture) of the retina; (3) Flash, flicker or multifocal electroretinogram recordings which measure the electrical response of the rod and cone photoreceptors in the retina to a light stimulus; (4) The visual evoked cortical potentials which access the integrity of the retino-geniculo striate pathway by measuring the electrical response of the visual area of the brain recorded from scalp electrodes to color vision testing; and (5) Visual acuity assessment using optotype (Snellen-style) eye charts. One would expect to see improvement or protection of the retina as measured by the methods described above.

For the optic nerve, therapeutic endpoint measurement would include the measurement of the visual evoked cortical potential from regions of the LGN or superior colliculus, to which the optic nerves project and the Pupillary Light Reflex test, which tests the integrity of the optic nerve (cranial nerve 2) and the oculomotor nerve (cranial nerve 3).

Therapeutic endpoints for improvement of visual function (measuring LED improvement of disease or injury to other components of the visual system—optic nerve, LGN visual pathways, etc.) preferably involves the use of a battery of tests which serve as standardized assessments for evaluation of the visual functions important in ensuring that visual perceptual processing is accurately completed. These include assessment of visual acuity (distant and reading), contrast sensitivity function, visual field, oculomotor function visual attention and scanning.

More detailed descriptions of retinal and visual function tests include, but are not limited by, the following methods. Kinetic (Goldmann) perimetry ("Perimetry" is the quantitative testing of the side vision). Automated (computerized) perimetry employs spots of light that are automatically projected into predetermined areas of the visual field. The test continues until the dimmest light is found that can be seen in each area of the side vision. These visual field tests provide important information. Critical Flicker Fusion Frequency (CFF) requires that patients view a flickering light to test the ability of the optic nerve to conduct impulses with uniform speed. This test has proven to be very useful in identifying visual loss due to optic nerve damage.

Infra-red video pupillography is a way of seeing the pupils clearly in the dark so that a more certain diagnosis can be made. It may also be used to transilluminate the iris to identify local iris causes for pupillary abnormalities.

Electroretinography is a regular ERG (eletroretinogram) that records the electrical activity of the whole retina in response to light and helps to determine if the rods and cones of the retina are firing in the correct way. The Multi-focal ERG (MERG) analyzes about one hundred ERGs at once by illuminating various little bits of the retina sequentially. It uses a computer to sort out the dizzying torrent of information and then it presents a map of the sensitivity of various parts of the retina, based on the electrical activity (in response to light) of all those different regions. If this map matches the map from perimetry, then the problem is in the retina and not in the optic nerve or brain.

Multi-focal Visual-Evoked Potentials (MVEP). Using a MERG stimulus, information can be picked up from the scalp that tells us if the visual pathways in the brain are damaged. Computer controlled infra-red sensitive pupillography is a method that is used to monitor pupillary movements in response to different types of light in order to quantify how much damage there might be in the visual system.

Computer controlled "Pupil" Perimetry is a method that uses the pupil movement in response to small lights presented in the field of vision as an objective indicator of how well the eye sees the light. Computer recording of eye movements can be used for monitoring pupil movements—but it also has the capacity to record the small movements of both eyes at the same time to see if they are tracking together and have normal movements in different directions of gaze.

Optical Coherence Tomography (OCT)—a device that looks at the retina at the back of the eye and measures the thickness of the layer of nerves coming from all quadrants of the retina and leading into the optic nerve. This nerve fiber layer may be thickened, thinned or normal, depending on the nature of the disease affecting the optic nerve. Ishihara Color Vision Test Cards—used for color vision evaluation. A test chart on color dots that appear as identifiable numbers or patterns to individuals who have various types of color vision deficits.

The retina is a complex sensory organ composed of different cell types arranged in distinct layers. The term "retinal function" will be used to refer to (1) activation of these layers by a light stimulus and (2) the processes required for maintenance of the cell. Different diseases may affect the retinal layers or cell types in a selective fashion. Congenital stationary night blindness affects transmission of visual signals in the rod-mediated visual pathway whereas achromatopsia affects only the cone pathway. Other diseases may affect both photoreceptor types in a defined location on the retina. Examples are the macular dystrophies, such as Stargardt's and age-related macular degeneration. Other diseases, such as glaucoma or optic neuropathy appear to affect primarily the ganglion cells, located on the surface of the inner retina.

Assessment of the efficacy of a therapeutic intervention in one of these retinal diseases therefore depends on the specific disorder. Congenital stationary nightblindness would be best assessed by the full-field electroretinogram in a patient that has been adapted to darkness for about 30 minutes. Conversely achromatopsia, absent cone function, is best assessed by a full-field electroretinogram under light-adapted conditions and with a rapidly flickering flash stimulus that isolates cone function. Diseases of the macula are evident in the multifocal ERG, but not the full-field. This is due to the fact the macula, with several hundred thousand photoreceptors makes a very small contribution to the full-field ERG signal, which is the sum of 12 million or more photoreceptors. For this reason, assessment of the therapeutic efficacy of an intervention to treat Stargardt's disease or age-related macular degeneration would be best accomplished by the multifocal ERG. Neither full-field ERGs nor multifocal ERGs contain a significant contribution from the ganglion cell layer. Assessment of interventions to affect the progression of glaucoma or Leber's hereditary optic neuropathy thus use the visually-evoked cortical potential because the visual cortical response is wholly-dependent on ganglion cell function and because the ERG is not affected in these diseases.

Certain issues that arise relate to mitochondrial dysfunction and retinal capillary cell death, and oxidative stress. In diabetic retinopathy, for example, oxidative stress is increased in the retinas of diabetic, sometimes resulting in blindness. The present treatment may provide an effective alternative to or companion to pharmaceutical treatment for these types of disorders.

Further, there are a number of different tests used in clinical ophthalmology that are designed to objectively measure the function of the retina. The retina must perform a number of functions in order to convert light entering the eye into an action potential in the visual cortex. The activation of the retinal layers by light results in the generation of electric fields in various levels of the visual system that can be recorded non-invasively. In theory, the light therapy could be beneficial in a wide range of diseases since it appears to affect basic cellular responses to insult such as ATP production and apoptosis. Thus there would be no one test that would be appropriate to assessing all the diseases that might benefit for light therapy.

Figure 2:
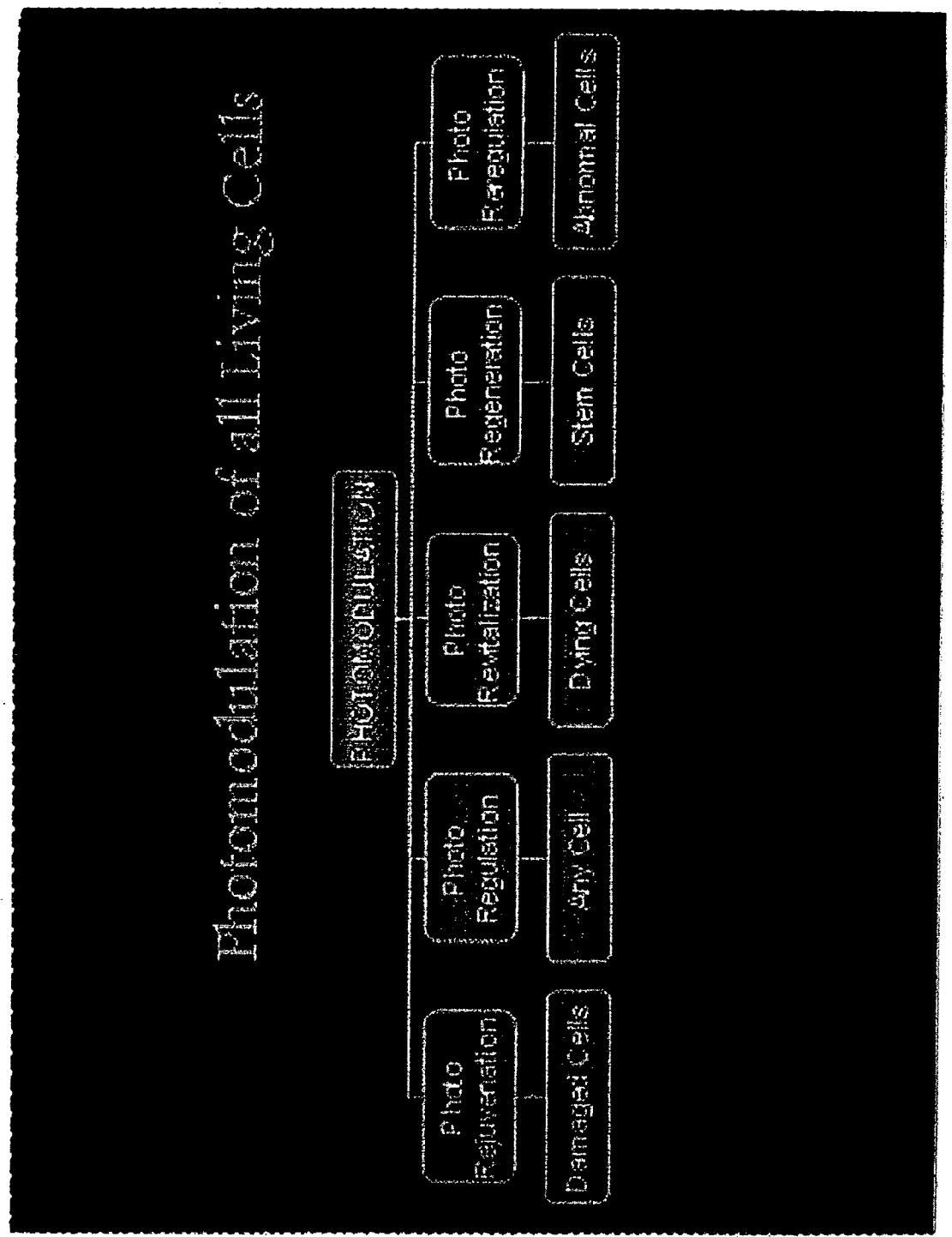

By way of illustrations, an array of LEDs can be used to emit light at one, or more, wavelengths to deliver energy fluence to the affected cells. The cells are provided with a clinically effective fluence of energy to initiate photomodulation and/or photoregeneration, but not enough light to cause damage to the cells due to the excessive light exposure that might be cause by higher-energy light sources such as lasers. As shown in FIGS. 1 and 2, there are 5 categories of photomodulatory treatment. There is photorejuvenation for "energizing" cells. Photoregulation controls or sends signals to cells. Photorevitalization may be used to slow, stop, or reverse programmed cells death or, in some case, revive necrotic cells. Photoregeneration may be used to differentiate cells. And photoreregulation may be employed to repair malfunctioning or damaged cells.

The illustrative array of LEDs may be used to deliver a continuous wave (CW) of light to the affected cells, or may be "pulsed" according to a code determined to provide beneficial treatment. A pulse code, for example, may be referred to by the length of each pulse, the time between each pulse, and the number of pulses. A pulse code of "250/100/100", for example, would refer to pulses of 250 milliseconds in duration, separated by 100 milliseconds, and repeated 100 times. Such a pulse code may deliver the same energy fluence as a 25 second continuous wave treatment.

The LED array may include LED emitters that emit multiple wavelengths, a single wavelength, or the array may include multiple types of emitters, if more than one wavelength is used for treatment. Each LED will generally emit at a dominant emissive wavelength between about 300 nm and 1600 nm. The array may include combinations of LEDs that emit in the visible and/or infrared portion of the spectrum. The emitters may be configured pulse, emit a continuous wave of light for an extended period of time, and emit simultaneously or in sequence. The total energy fluence delivered depends on the specific affliction being treated, but will generally be less than about 10 J/cm$^2$, to avoid possible negative effects due to overexposure of the retinal cells. When the light is being administered indirectly to the target, the fluence at the source may be much higher than 10 J/cm$^2$, but the fluence perceived by the source may be very low, due to the absorption and scattering of the light by tissue, bone, or other structures between the light source and the targeted cells. In some cases, a fluence as perceived by the targeted cells may be as small as a few nanojoules and the treatment may still be effective.

An illustrative embodiment of the invention may include the use of a combination of yellow and IR light, for example 590 nm and 870 nm, emitting at a power of 4.0 mW/cm2 with a pulse code of 250/100/100, or delivering about 0.1 J/cm$^2$. Pulse codes ranging from 2/1/1 to about 1000/1000/1000 may be employed to deliver a clinically effective amount of treatment light to retinal cells, however pulses with a duration as short of nanoseconds are believed to provide effective treatment in certain circumstances, thus these pulse codes are merely illustrative and not exhaustive of possible codes.

Figure 3:
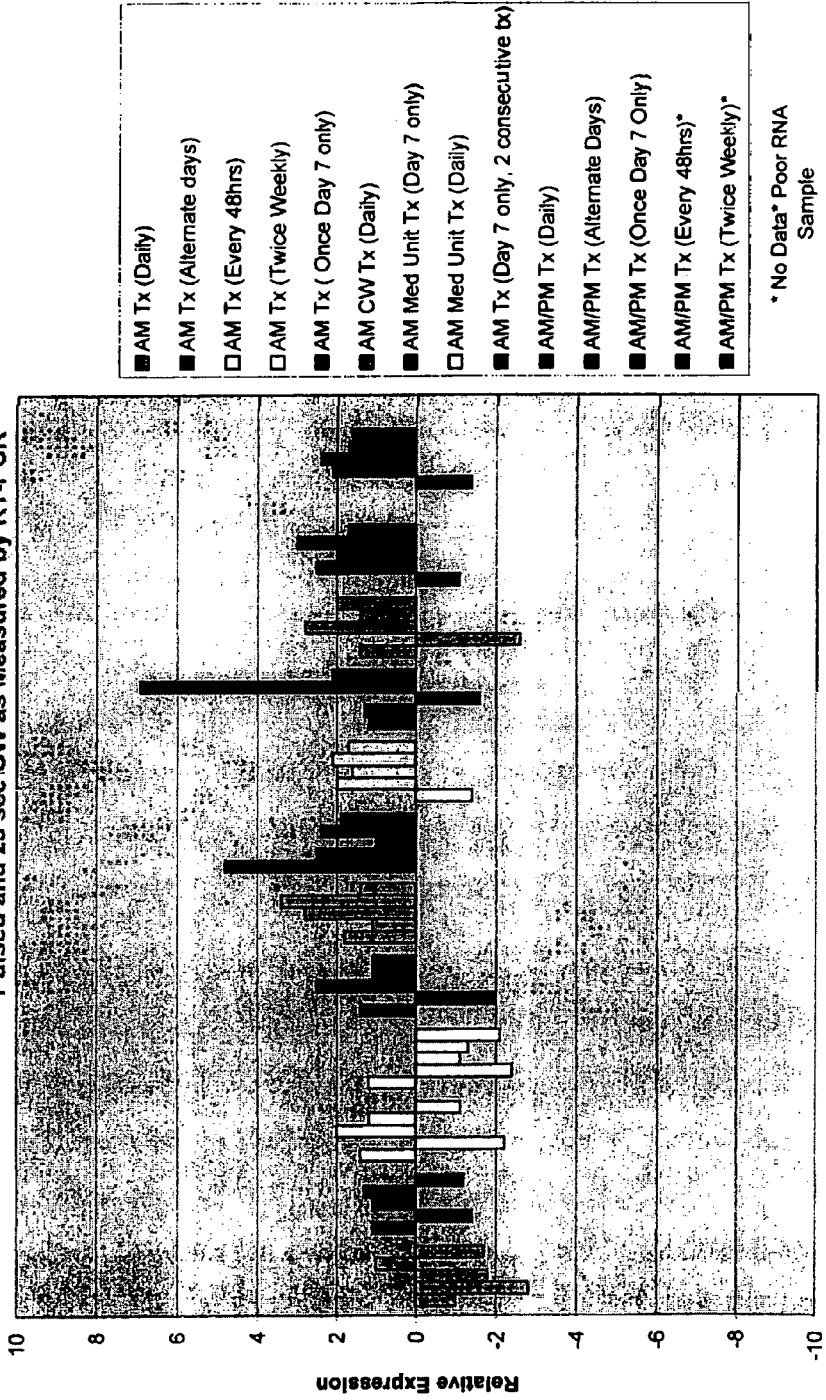
FIG. 3 shows a comparison of the efficacy of certain treatments for various factors in human skin.
Figure 4:
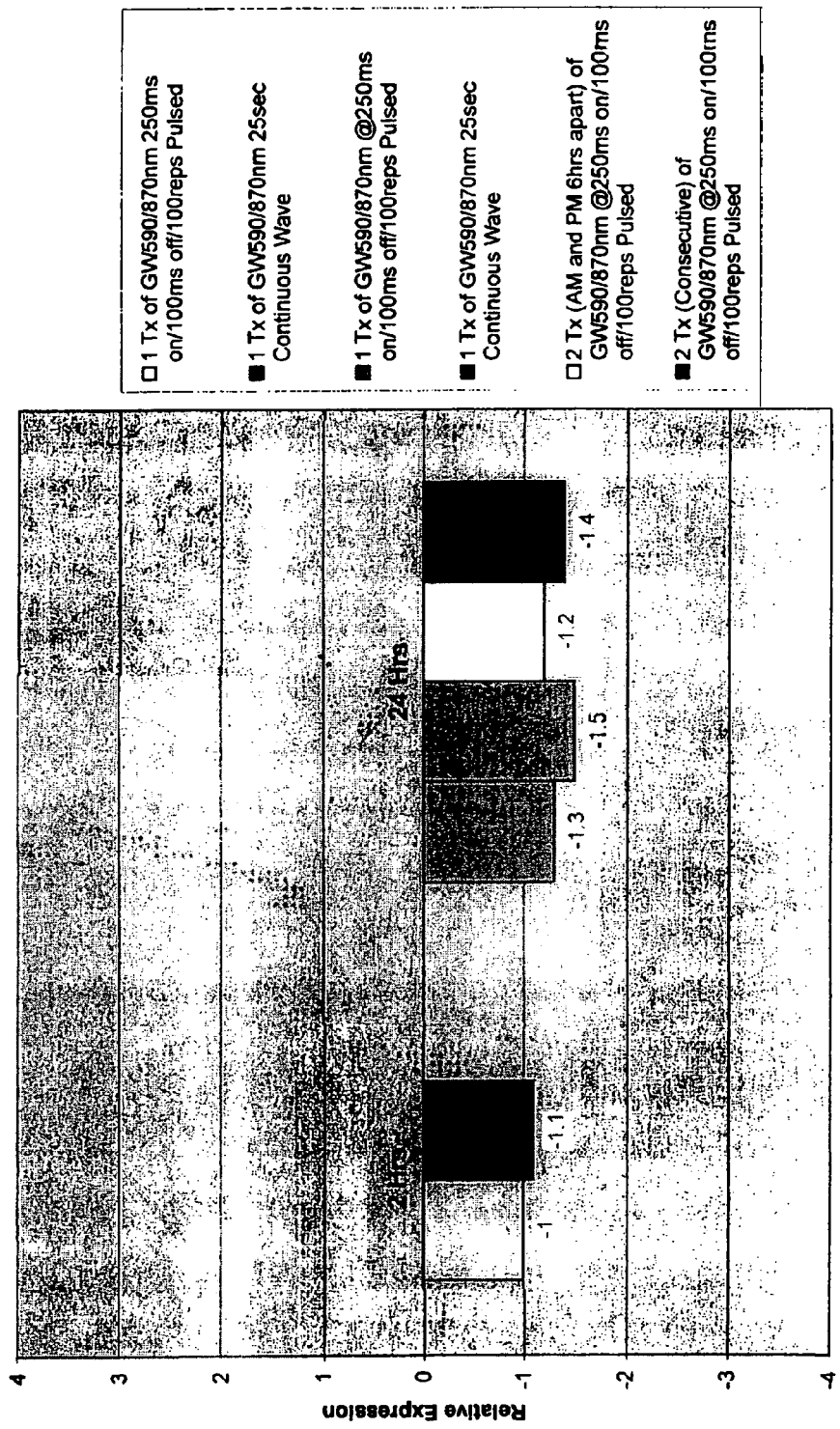
FIG. 4 shows the relative expression of VEGF in cultured human retinal pigmented epithelial cells subjected to various treatments of the present invention.

As is shown in FIGS. 3 and 4, particularly effective treatment regimen may deliver UVA1 light in combination with light of a lower wavelength. In one embodiment of the invention useful for treatment macular degeneration, an energy fluence of 0.1 J/cm$^2$ may be delivered to the eyes (retinal pigment epithelial cells) of a patient either by pulsing sources according to a 250/100/100 pulse code, or for a continuous exposure of 25 second. Either treatment delivers an identical energy fluence to the target cells; however it has been found that certain cells respond differently to pulsed and continuous wave treatment, as illustrated in the figures. As well, the time between treatments, as shown in FIG. 3, can affect the efficacy of the procedure.

As well, combinations of the various modes may be employed as can combinations of light sources within an array for treatment. For example, it may be desirable to combine multiple wavelengths, as shown in the examples below, to achieve more efficient treatment. The multiple wavelengths may include combinations of light in the visible spectrum, combinations of visible and infrared or ultraviolet light, or combinations of non-visible light. In one illustrative embodiment of the invention, a combination of yellow and infrared light may be used to augment the treatment achieved by 660 nm light with heat produced by light in the infrared region (>700 nm).

The targeted cells may be exposed to one or more wavelengths of LED emitted from a single LED or an array of LEDS, each of which may emit one or more wavelengths of light in the range of from about 300 nm to about 1600 nm. A variety of parameters may be used (including pulse duration, energy, single or multiple pulses, the interval between pulses, the total number of pulses, etc.) to deliver sufficient cumulative energy to interact with the cells. This may result in improved cellular activity, through photomodulatory means, photothermal means, or combinations thereof. Moreover, when multiple light sources are employed, the ratio of intensity of each source should be selected with respect to each of the other light sources. For example, one illustrative use of the invention may employ three light sources. The light sources may have dominant emissive wavelengths of 590 nm, 660 µm, and 870 nm. Although for certain types of treatment, the "pulse code" of the light may result in any number of patterns of simultaneous or sequential use of each source, treatments using the same or different pulse code (or continuous wave) may vary due to difference in operating power of each source.

For treating "wet" macular degeneration, each of the light sources may operate at the same or different power. In other instances, the power output of any individual sources may be varied with respect to each of the other light sources.

Two entirely different lasers, LED, or light beams may be delivered substantially simultaneously through the same optics at different parameters. For example, one beam may be delivered primarily to release or to activate, and a second beam primarily to treat. Additive or complimentary effects may be achieved by using two beams at the same time, such as the use of red light with a wavelength of approximately 660 nm and another with a wavelength of approximately 880 nm. Alternatively, selecting a first wavelength to match the wavelength responded to by mitochondrial cytochromes or DNA and a second wavelength to respond to target receptors may be found beneficial.

Some examples of possible operating parameters may include the wavelengths of the electromagnetic radiation to the cells to be regenerated, stimulated, inhibited, or destroyed, the duration of pulses (pulse duration) of the electromagnetic radiation, the number of pulses, the duration between pulses, also referred to as repetition rate or interpulse interval. Intervals between treatments can be as long as hours, days, weeks, months, etc.; and the total number of treatments is determined by the response of the individual patient. Further, treatment regimens using a combination of more than one wavelengths either simultaneous or in sequence may be used. As well, the energy intensity of the radiation as measured at the living tissue (typically measured in Joules per centimeter squared, watts per centimeter squared, etc.), the pH of the cell, tissue or skin, the skin temperature, and time from application to treatment with a light source, if used with exogenous chromophore (which can be topical, injected, driven in with ultrasound, or systemic) is determined by the nature of the treatment and is further illustrated in the Examples.

Wavelength—Each target cell or subcellular component, or molecular bond therein, tends to have at least one unique and characteristic "action spectrum" at which it exhibits certain electromagnetic or light absorption peaks or maxima. FIG. 3, for example, shows the absorption spectrum of one line of human fibroblast cells in monolayer tissue culture. Different cell lines (of the same cell—for example fibroblasts from 3 different patients) exhibit some differences in their absorption spectra and thus using narrow band multichromatic light (rather than monochromatic light) is also useful in producing the optimal clinical effect. When these cells or subcellular components are irradiated with wavelengths corresponding to the absorption peaks or maxima, energy is transferred from the light photon and absorbed by the target. The particular features of the delivered energy determine the cellular effects. The complexity of these combinations of parameters has produced much confusion in the prior art. Basically, the wavelength should roughly correlate with absorption maxima for the target cell or subcellular component or tissue, or exogenous chromophore. In some cases it may be desirable to target more than one maxima—either simultaneously or sequentially on the same or different treatment dates. The presence of multiple maxima action spectra is common for a given cell or subcellular component or exogenous chromophore and different wavelength maxima irradiation may produce different results.

If the wavelength band is overly broad, then the desired photomodulation effects may be altered from those intended. Consequently, use of broad band noncoherent intense light sources may be less desirable than those specified for use with the present invention, in contrast to the use of multiple narrowband emitters. The laser diodes are also multichromatic with narrow wavelength bands around a dominant band, i.e., they are narrowband multichromatic devices—devices which emit electromagnetic in a narrow band of radiation either symetrically or asymetrically around a dominant wavelength. For purposes of the present invention, any device that emits electromagnetic radiation in a bandwidth of +/− less than about 100 nanometers around a dominant wavelength can be considered to be a narrowband, multichromatic emitter. LEDs, while not monochromatic, emit in such a narrow band as to be considered narrowband multichromatic emitters. The narrow band allows photons of slightly different wavelengths to be emitted. This can potentially be beneficial for creating certain desirable multi photon interactions. In contrast, most commercial lasers emit light at a single wavelength of light and are considered monochromatic. The use of lasers, according to the prior art, has relied upon the coherent, i.e., monochromatic, nature of their electromagnetic emissions.

Wavelength may also determine tissue penetration depth. It is important for the desired wavelength to reach the target cell, tissue or organ. Tissue penetration depth for intact skin may be different than the tissue penetration depth for ulcerated or burned skin and may also be different for skin that has been abraded or enzymatically peeled or that has had at least a portion of the stratum corneum removed by any method.

Energy Density—The energy density corresponds to the amount of energy delivered during irradiation and is also referred to as energy intensity and light intensity. The optimal 'dose' is affected by pulse duration and wavelength—thus, these are interrelated and pulse duration is very important—in general high energy produces inhibition and lower energy produces stimulation.

Pulse duration—The exposure time for the irradiation is very critical and varies with the desired effect and the target cell, subcellular component, exogenous chromophore tissue or organ. (e.g. 0.5 microseconds to 10 min may be effective for human fibroblasts, though greater or lesser may also be used successfully).

Continuous Wave (CW) vs. pulsed—e.g. the optimal pulse duration is affected by these parameters. In general, the energy requirements are different if pulsed mode is used compared to continuous (CW) modes. Generally, the pulsed mode is preferred for certain treatment regimen and the CW mode for others.

Frequency (if pulsed)—e.g. higher frequency tends to be inhibitory while lower frequency tends to be stimulatory, but exceptions may occur.

Duty cycle—This is the device light output repetition cycle whereby the irradiation is repeated at periodic intervals, also referred to herein as the interpulse delay (time between pulses when the treatment session comprises a series of pulses).

Application of the appropriate treatment regime may depend on the type of cellular injury or disorder being treated. For example, some acute cell injuries are characterized by the proliferation of free radicals causing oxidative stress. While antioxiant drugs may be helpful against such afflictions, light therapy has been found to be an effective treatment for this, as well as chronic cell disorders. A chronic cell disorder may be one that is exhibited after continual exposure to some environmental factor—such as increased incidents of cataracts witnessed in those who are exposed to above-average levels of UV radiation over an extended period of time (fishermen, for example). Depending on the type of cells disorder—chronic (or degenerative) or acute—the treatment regimen may differ. Moreover, it has been found that the time intervening between an acute cell injury and the commencement of light treatment may be influential in determining the most effective treatment, as well.

Figure 5:
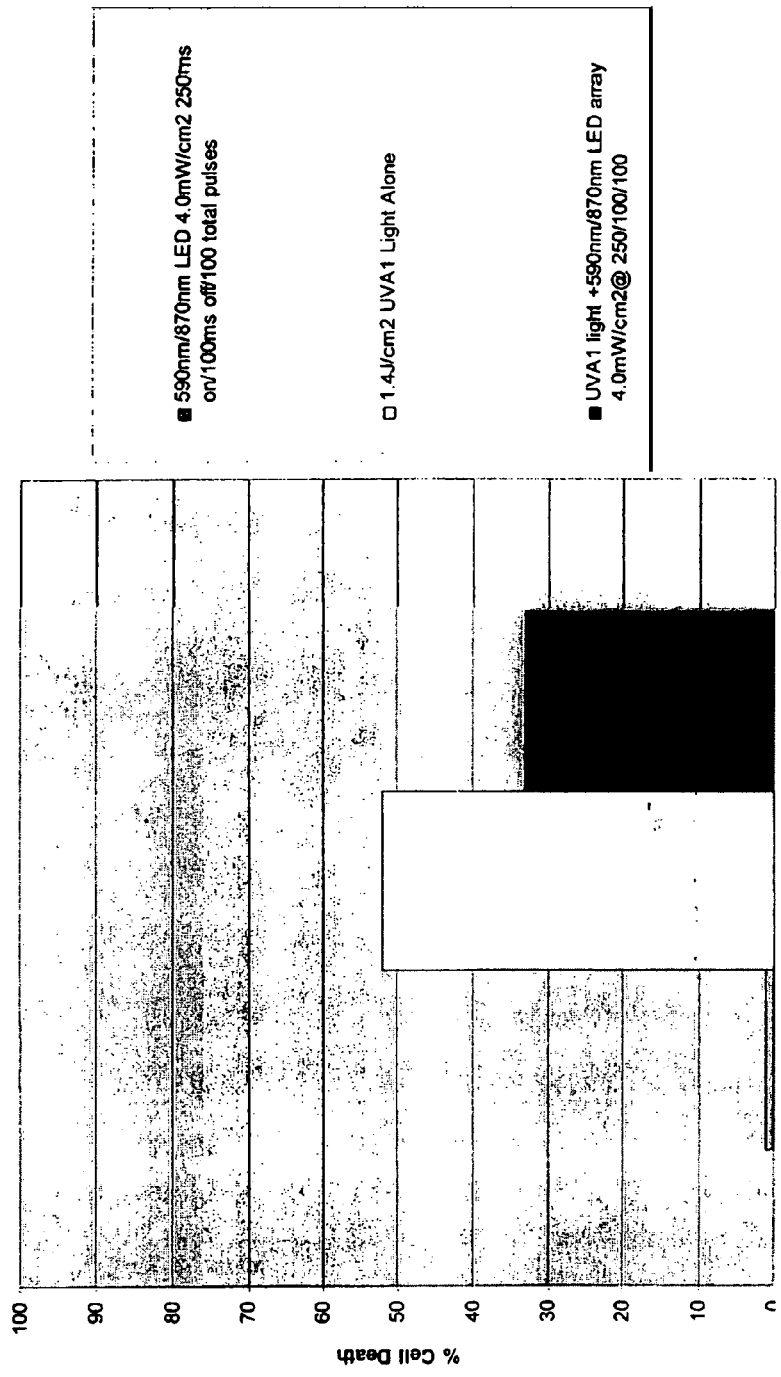
FIG. 5 is a graph showing the response of cells that have been exposed to acute UV injury, after being treated with various LILT treatments of the present invention.
Figure 6:
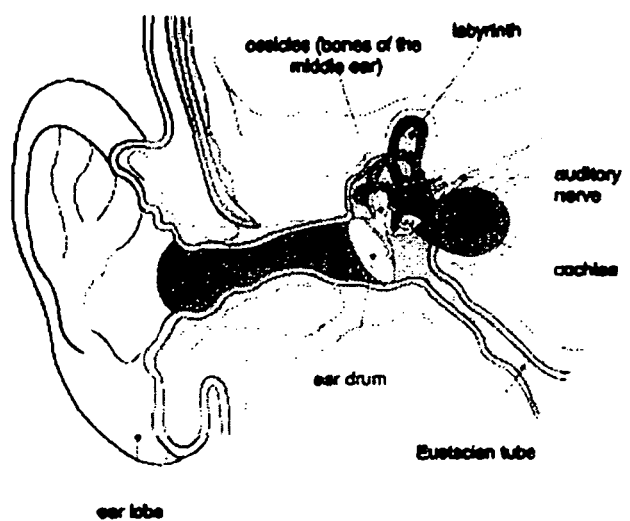
FIG. 6 is an illustration of the human auditory system.

Although not wishing to be bound by theory, it is believed that prior to cell death (necrosis), cells that have been injured undergo programmed cell apoptosis. This is a period of time wherein the functions of the cell go through various stages until cell necrosis occurs (i.e., a pre-programmed cellular self-destruct sequence at least partially governed by mitochondrial DNA). Previously, it has been though that once programmed apoptosis begins, the inevitable result was necrosis. It has been shown; however, that light therapy may halt or even reverse apoptosis, thereby restoring normal cellular activity, as illustrated in FIG. 5.

In addition to being an effective treatment method for macular disorders, the present invention also has application to the reduction of cellulite, migraine headaches, strokes, heart attacks, and other medical conditions. Additionally, light therapy may be used in place of or to augment antioxidant compounds used to preserve and prepare harvested organs for transplant.

Using any of the light sources suitable for use as described herein, adipocyte cells can be photomodulated. Photomodulation increases the local microcirculation in the cellulite and alters the metabolic activity of the cells. Enhanced local microcirculation, metabolism or enzymation activity, or combinations thereof, may be produced by photomodulatory means. To enhance the treatment, any of the topical chromophores as previously described can be used or non-chromophoric compositions can be used in conjunction with any of the photomodulatory methods, including low-intensity light therapy. Further photothermal means may be used to destroy adipocyte cells alone or in combination with photomodulatory means, with or without the use of exogenous chromophores.

Many living organisms—both animals and plants—have as one of their major defense mechanisms against environmental damage to their cells and DNA repair system. This system is present in many if not all living organisms ranging from bacteria and yeasts to insects, amphibians, rodents and humans. This DNA mechanism is one which is involved in processes to minimize death of cells, mutations, and errors in copying DNA or permanent DNA damage. These types of environmental and disease and drug related DNA damage are involved in aging and cancer.

One of these cancers, skin cancer, results from ultraviolet light damage to the DNA produced by environmental exposure to natural sunlight. Almost all living organisms are unavoidably exposed to sunlight and thus to these damaging UV rays. The damage which is produced is a change in the structure of the DNA called pyrimidine dimmers. This causes the DNA structure to be altered so that it cannot be read or copied any longer by the skin cells. This affects genes and tumor development and proper functioning of the immune system.

An enzyme called photolyase helps to restore the original structure and function of the damaged DNA. Interestingly photolyases are activated by light . . . to then act to repair the DNA damaged by ultraviolet light. In the dark it binds to the cyclobutane pyrimidine dimmer created by the UV light and converts it into two adjacent pyrimidines (no dimer connecting these any longer) and thus the DNA damage is repaired. This direct reversal of DNA damage is called "photoreactivation". The photolyase upon exposure to blue light absorbs the light energy and uses this energy to 'split' the dimer and thus restore the normal DNA structure. Other mechanisms of DNA repair exist as well.

The photolyase repair mechanism is not well understood at present, but naturally occurring or synthetic or genetically engineered photolyase from essentially any living organism source can be utilized for other organisms including human and veterinary and plant applications. DNA damage produced by factors other than ultraviolet light may also be repaired including, but not limited to, such factors as other environmental damage or toxins, radiation, drugs, diseases, chemotherapy for cancer, cancer, microgravity and space travel related damage, and a myriad of other causes.

The use of such naturally derived or artificially created or genetically engineered photolyase enzymes or related enzymes or other proteins functioning for DNA or RNA repair have a wide variety of applications. For example, the ability to treat skin damaged by sunlight/ultraviolet light of disease and to repair, reverse, diminish or otherwise reduce the risk of skin cancer could be used either as a therapeutic treatment or as a preventive measure for people with severely sun damaged skin, with precancerous skin lesions, or with skin cancer.

This principle applies not only to skin cells and skin cancer but to a very broad range of skin and internal disorders, diseases, dysfunctions, genetic disorders, damage and tumors and cancers. In fact potentially any living cells might have beneficial effects from treatment with photolyase or similar proteins in combination with light therapy.

While in nature the light to activate the photolyase typically comes from natural sunlight, essentially any light source, laser and non laser, narrow band or broader bandwidth sources can activate the photolyase if the proper wavelengths and treatment parameters are selected. Thus natural sunlight filtered through a selective sunscreen could be used to activate both native and exogenously applied photolyases. Another treatment option would be to apply the photolyase and then treat with a controlled light source exposure to the proper wavelength band and parameters. A wide variety of light sources could be utilized and the range of these is described elsewhere in this application. For example a low energy microwatt narrow band but multispectral LED light source or array with mixed wavelengths could be utilized. Another embodiment is a filtered metal halide light source with a dominant wavelength of 415 nm+/−20 nm and an exposure of 1-30 minutes at 1-100 milliwatts output can be utilized. Such exposure would occur minutes to days after application of a topical product containing photolyase.

Another example would be the repair of cells in the skin which have environmental damage but instead of repairing the cells which lead to skin cancer the cells which lead to aging (photoaging) of the skin are targeted for this therapy. In one embodiment, kin fibroblasts which have been sun damaged are treated with a photolyase and subsequently the photolyase is photomodulated with blue light to set in motion the DNA repair mechanism of photolyase—that is photoreactivation. This allows the repair of the structure and thus the normal functioning of the fibroblast DNA thus allowing normal functioning and proliferation of these fibroblasts—which produce the proteins such as collagen and elastin and hyaluronic acid and matrix ground substance which cause skin to be firm and elastic and youthful in appearance—thus producing anti-aging or skin rejuvenation effects in the skin as well as improving the structure and healthy function of the skin.

Various cofactors which are involved in this photoreactivation process can also be added either topically or systemically to further enhance or improve the efficiency of this process. Other cofactors needed in the production of these proteins once the cells recover normal function also may be added topically or systemically to enhance the anti-aging or skin rejuvenation process. The delivery of both the photolyase and/or the cofactors described above can be enhanced by utilizing ultrasound to increase skin permeability or to increase transport across the skin barrier and into the skin and underlying tissues. Removal of a portion of the stratum corneum of the skin can also be used, alone or in combination with ultrasound, to enhance penetration and delivery of these topically applied agents. Additionally such methods of removing or altering the stratum corneum can assist in penetration of the light or the efficiency of same or allow use of lower powered light sources including home use devices such as battery powered LED sources.

A variety of sources exist for obtaining photolyases. These may include native naturally occurring photolyases, compounds derived from other living organisms (that is one may use for example bacterially derived, or yeast derived, or plankton rederived, or synthetic or genetically engineered, etc., photolyases and use them in human skin for beneficial effects thus not limited to same species derived photolyases. One known photolase is derived from *Anacystis nidulans* while others can be derived from bacteria—yeast in fact protect themselves with a photolyase which can be used in humans, other microorganisms, plants, insects, amphibian and animal sources exist.

The photolyase enzymes function by light induced electron transfer from a reduced FAD factor to the environmental exposure produced pyrimidine dimers. The use of free radical inhibitors or quenchers such as antioxidants can also be used to supplement the photolyase therapy. Other light activated chromophores may be utilized with light sources and properly selected parameters to further enhance, stimulate, photomodulate, photoactivate or photoinhibit the target or supporting cells or tissue to promote the most effective treatment.

There are many causes of free radical damage to cells. In one embodiment wound healing can be accelerated by utilizing a combination of antioxidants, cell growth factors, direct photomodulation (photoactivation) of cells, and photoreactivation through photolyases. Topical or systemic therapy with the proper cofactors and replacing any deficiencies of cofactors can further enhance wound healing. For example, a chronic leg ulcer wound could be treated with an antioxidant mixture of vitamin E, vitamin C and glutathione, as well as cofactors such as fatty acids and keto acids and low level light therapy using and LED array with parameters selected to photostimulate fibroblasts and epithelial cells could also receive treatment with a photolyase and blue light therapy thus greatly accelerating wound healing and healing wounds or burns that would otherwise not be treatable.

The potential uses of photolyases and light therapy include: the treatment or repair or reverse nerve damage or diseases including spinal cord injuries and diseases; cancer or cancer treatment related problems including radiation and chemotherapy; cervical dysplasia and esophageal dysplasia (Barrett's esophagus) and other epithelial derived cell or organ disorders such as lung, oral cavity, mucous membranes, etc.; eye related diseases including but not limited to macular degeneration, cataracts, etc.

There is very broad health and commercial applications of photolyase mediated photorepair or photoreactivation of DNA (or RNA) damage with flavin radical photoreduction/ DNA repair via photomodulation or native or exogenously applied natural or synthetic or genetically engineered photolyases. The addition of topical, oral, or systemically administered photolyases and also their cofactors or cofactors of the cells whose DNA is being repaired further enhance these applications. The enhanced delivery of such substances topically via ultrasound assisted delivery, via alteration of the skin's stratum corneum, and/or via special formulations or via special delivery vehicles or encapsulations are yet an additional enhancement to this process.

There are also blue light photoreceptors such as cryptochrome which photomodulate the molecular clocks of cells and the biological or circadian rhythm clocks of animals and plants—that is the mechanism which regulates organism response to solar day/night rhythms in living organisms. These protein photoceceptors include vitamin B based crytochromes. Humans have two presently identified cryptochrome genes—which can be directly or indirectly photomodulated (that is photoactivated or photoinhibited).

The clinical applications include treatment of circadian rhythm disorders such as 'jet lag', shift work, etc, but also insomnia, sleep disorders, immune dysfunction disorders, space flight related, prolonged underwater habitation, and other disturbances of circadian rhythm in animals. Circadian issues also exist for many other living organisms including the plant kingdom.

Warts can be treated using exogenous or endogenous chromophores with either photothermal or non thermal photomodulation techniques—or a combination of both. Examples of preferred embodiments of endogenous chromophores include the targeting of the vascular blood supply of the wart with either method. Anther preferred embodiment is the use of a topically applied or injected or ultrasonically enhanced delivery of such a chromophore into the wart or its blood supply or supporting tissues with subsequent photomodulation or photothermal activation of the chromophore.

One such example would be that of a chlorophyll topical formulation similar to those described elsewhere in this application but of higher concentration and vehicle and particle size optimized for wart therapy and the anatomic location of the warts (for example warts on the thicker skin of the hand might be formulated differently than that used for vaginal warts). An LED light source could be used for home use with 644 nm in a battery powered unit wherein the topical formula was applied daily and treatment of individual warts was performed with the proper parameters until the warts disappeared.

For the situation of vaginal warts, a cylindrical device with an array of LED arranged and optically diffused such that the entire vaginal cavity could be properly illuminated in a medically performed procedure would represent another embodiment of this therapy. A wide range of substances can be utilized either as the primary chromophore or as adjunctive supporting therapy. These compounds are listed elsewhere in this application. In another embodiment an immune stimulator is utilized in conjunction with photomodulation with or without an exogenous chromophore. In yet another embodiment a higher powered light source either narrow or broad band can e utilized with the same chromophore therapy as outlined above, but with parameters selected so that the interaction with the chromophore is non photomodulation, but rather intense photothermal effect so as to damage or destroy the wart but with minimal damage to surrounding uninvolved and non supporting tissues.

In one embodiment a chlorophyll and carotenoid topical formulation is applied and natural sunlight with or without a selective sunscreen are used to interact with the topical formulation. Another embodiment utilizes an injected or ultrasonically enhanced topical delivery of a dye such as indocyanine green which has been used for vascular injections safely in other medical applications.

Papulosquamous, eczematous and psoriasiform, atopic dermatitis, and related skin disorders can be improved, controlled, reduced or even cleared by the same photomodulation or photothermal interaction with endogenous or exogenous chromophores. The process outlined for warts and the other disorders in this application may be used for such therapies. The use of ultrasound is particularly useful in the more scaly disorders in this group of diseases as are enzyme peels and other methods with gently remove scaling skin. Penetration of light into psoriasis presents for example a major problem with current therapies. Penetration of drugs and topical agents is likewise a major therapeutic challenge. If the dry skin on top of psoriasis is removed it is well known that this stimulates further growth of the plaque or lesion of psoriasis—yet removal is needed to allow the drugs to penetrate and for light to penetrate. Currently almost all psoriasis light therapy is ultraviolet light and thus the risk of skin cancer and also of photoaging is very significant with a lifetime of repeated ultraviolet light therapy. Also such therapy typically involves treating large areas or even the entire body (standing in a large light therapy unit is like being in a tanning bed which is standing upright). Thus not only does the skin with psoriasis lesions get treated, but also all the normal uninvolved skin typically gets exposed to the damaging ultraviolet light.

Furthermore typical psoriasis treatments involve the use of oral drugs called psoralens. These drugs cross link DNA and are light activated. Thus DNA damage in produced not only by the ultraviolet light itself (like being out in sunlight but primarily ultraviolet A light), but in addition the psoralen drug produced DNA damage. Safety in children in an obvious concern as is use in pregnant or childbearing women.

The use of a topical light activated exogenous chromophore such as most of the agents listed in this application present no risk of DNA damage and also are generally very safe products—many are natural such as chlorophyll and can be safely used in children and pregnancy and child bearing age women. In addition the treatment is only activated where the topical agent is applied—unlike the use of oral psoralen drugs that activate not only the entire skin but also the retina and other tissues. The light used for this therapy is not only low in power, but it is for the most part visible or infrared light and is not ultraviolet—producing no DNA damage.

Thus the use of photomodulation or photothermal activation of exogenous light activated chromophores such as described herein represents a significant advance in safety and efficacy.

The photolyase embodiments described above also have some application for diseases such as psoriasis. For some cases of psoriasis are very extensive covering large amounts of the surface area of the body and may be resistant to other known therapies. The application of a topical formulation to the areas not being treated—or to all the body areas exposed to the traditional psoriasis phototherapy could receive a post treatment with the photolyase and blue light therapy—think of this as a type of 'antidote' to the ultraviolet psoriasis phototherapy wherein the repair of DNA damage to normal tissue was facilitated immediately following the psoriasis therapy—thus reducing significantly the risk of skin cancer and photoaging in future years.

Another embodiment involves the use of such a photolyase preparation in the evening after returning from a long day of occupational sun exposure or after an accidental sunburn. A spray or lotion containing the photolyase could be applied and then photorepair/photareacitvation of the acutely damaged DNA in the skin could be performed—and this could be performed with a large beam diameter home therapy unit—of by a white light source which contained enough of the desired wavelength at the proper parameters to produce this reaction. Additionally an antioxidant skin formulation could be also applied to minimize erythema and other undesired effects of the sunburn. One such embodiment would be the preparation described earlier with a combination of vitamin C, vitamin E and glutathione and free fatty acids and one or more keto acids. A similar formulation could contain these agents but utilize only one or two of the three antioxidants listed.

In vitro fertilization processes can also be enhanced by photomodulation—with or without an exogenous chromophore. This can simply target the cells or subcellular components themselves, as described in the applicants copending U.S. patent application Ser. No. 09/894,899 entitled "Method and Apparatus for Photomodulation of Living Cells", which is hereby incorporated by reference in its entirety.

This can result in a greater success rate of fertilization and/or growth of embryos or other desirable effects on this process. In one embodiment an LED light source is used to treat sperm of animals or humans or genetically engineered embryos or subcomponents thereof to enhance fertilization.

In another embodiment photolyase or other photoreparative or light activated DNA repair proteins or substances combined with photomodulation can be utilized to 'correct' DNA damage in embryonic tissues thus generating a normal or more normal embryo. This can be performed in vitro or in utero (utilizing tiny fiber optic delivery of the proper light parameters—or the light can be delivered from outside the body into the womb without the risk of introducing a fiber optic device.

Another process in which photomodulation can be utilized for significant benefit is in the stimulation of proliferation, growth, differentiation, etc of stem cells from any living organism. Stem cells growth and differentiation into tissues or organs or structures or cell cultures for infusion, implantation, etc (and their subsequent growth after such transfer) can be facilitated or enhanced or controlled or inhibited. The origin of such stem cells can be from any living tissue or organism. In humans stem cells for these embodiments may come from any source in the human body, but typically originate from the bone marrow, blood, embryo, placenta, fetus, umbilical cord or cord blood, and can be either naturally or artificially created either in vivo, ex vivo or in vitro with or without genetic alteration or manipulation or engineering. Such tissue can come from any living source of any origin.

Stem cells can be photoactivated or photoinhibited by photomodulation, including stem cell differentiation for regeneration of the visual system and specifically the retina and retinal pigment epithelial cells and photoreceptor cells. There is little or no temperature rise with this process although transient local nondestructive intracellular thermal changes may contribute via such effects as membrane changes or structured conformational changes.

The wavelength or bandwidth of wavelengths is one of the critical factors in selective photomodulation. Pulsed or continuous exposure, duration and frequency of pulses (and dark 'off' period) and energy are also factors as well as the presence, absence or deficiency of any or all cofactors, enzymes, catalysts, or other building blocks of the process being photomodulated.

Photomodulation can control or direct the path or pathways of differentiation of stem cells, their proliferation and growth, their motility and ultimately what they produce or secrete and the specific activation or inhibition of such production.

Photomodulation can up-regulate or down-regulate a gene or group of genes, activate or inactivate enzymes, modulate DNA activity, and other cell regulatory functions.

Our analogy for photomodulation of stem cells is that a specific set of parameters can activate or inhibit differentiation or proliferation or other activities of a stem cell. Much as a burglar alarm keypad has a unique 'code' to arm (activate) or disarm (inhibit or inactivate) sending an alarm signal which then sets in motion a series of events so it is with photomodulation of stem cells.

Different parameters with the same wavelength may have very diverse and even opposite effects. When different parameters of photomodulation are performed simultaneously different effects may be produced (like playing a simple key versus a chord on a piano). When different parameters are used serially or sequentially the effects are also different—in fact depending on the time interval we may cancel out the prior photomodulation message (like canceling burglar alarm).

The selection of wavelength photomodulation is critical as is the bandwidth selected as there may be a very narrow bandwidth for some applications—in essence these are biologically active spectral intervals. Generally the photomodulation will target flavins, cytochromes, iron-sulfur complexes, quinines, heme, enzymes, and other transition metal ligand bond structures though not limited to these.

These act much like chlorophyll and other pigments in photosynthesis as 'antennae' for photo acceptor molecules. These photo acceptor sites receive photons from electromagnetic sources such as these described in this application, but also including radio frequency, microwaves, electrical stimulation, magnetic fields, and also may be affected by the state of polarization of light. Combinations of electromagnetic radiation sources may also be used.

The photon energy being received by the photo acceptor molecules from even low intensity light therapy (LILT) is sufficient to affect the chemical bonds thus 'energizing' the photo acceptor molecules which in turn transfers and may also amplify this energy signal. An 'electron shuttle' transports this to ultimately produce ATP (or inhibit) the mitochondria thus energizing the cell (for proliferation or secretory activities for example). This can be broad or very specific in the cellular response produced. The health of the cells and their environment can greatly affect the response to the photo modulation. Examples include hypoxia, excess or lack or ration of proper cofactors or growth factors, drug exposure (e.g. reduced ubiquinone from certain anticholesterol drugs) or antioxidant status, diseases, etc.

The as yet unknown mechanism, which establishes 'priorities' within living cells, can be photomodulated. This can include even the differentiation of early embryos or stem cell population. Exogenous light activated chromophores may also be used alone or in combination with exogenous chromophores. Genetically altered or engineered stem cells or stem cells which have an inborn genetic error or defect or uncommon but desirable or beneficial trait may require a different 'combination' of parameters than their analogous 'normal' stem cells or may produce different cellular response if use the same combination of parameters. Using various methods of photomodulation or other techniques known in the art more specific cellular effects may be produced by 'blocking' some 'channels' that are photomodulated.

For example, consider an old fashioned juke box, if one selects the proper buttons one will set in motion a series of events resulting in the playing of a very specific and unique record or song. If however one were given a broom to push the buttons one would have to block all but the desired button to be selective. Likewise pushing an immediately adjacent button will not produce the desired outcome.

The magnitude of effects on cells may also be very dependent on the wavelength (when other parameters are the same). One such example is the contrast between irradiating chemical bonds in DNA with 302 nm light versus 365 nm light—the 302 nm light produces approximately 5000 times greater DNA pyrimidine dimers than the 365 nm only a short distance up the spectrum. Changing the wavelength can also convert the ratio or type of these dimers. Thus seemingly subtle changes in photomodulation or photochemical reaction parameters can produce very large and very significant differences in cellular effects—even at the subcellular level or with DNA or gene expression.

A final analogy is that photo modulation parameters can be much like a "morse code" to communicate specific 'instructions' to stem cells. This has enormous potential in practical terms such as guiding or directing the type of cells, tissues or organs that stem cells develop or differentiate into as well as stimulating, enhancing or accelerating their growth (or keeping them undifferentiated).

Another application of photomodulation is in the treatment of cellulite. Cellulite is a common condition which represents a certain outward appearance of the skin in certain anatomic areas—most commonly on the upper legs and hips which is widely regarded as cosmetically undesirable. Cellulite is the result of a certain anatomic configuration of the skin and underlying soft tissues and fat which may involve abnormalities of circulation or microcirculation or metabolic abnormalities—predominantly in the fat and supporting tissues. Photomodulation or photothermal treatments of the adipocytes (fat cells) or their surrounding supporting structures and blood supply alone or in combination can reduce the appearance of cellulite and/or normalize the structure and function of the tissues involved with the cellulite.

Photomodulation of adipocytes can be performed using endogenous chromophores such as the adipocytes themselves, their mitochondria or other targets within the adipocyte electron transport system or respiratory chain or other subcellular components. Exogenous light or electromagnetically activated chromophores can also be photomodulated (photoactivated or photoinhibited) or photothermal interactions can also occur. Examples of such chromophores are listed elsewhere in this application and can be topically or systemically introduced into the target tissues or adipocytes or surrounding blood vessels. The use of externally or internally applied ultrasound can be utilized either to enhance delivery of the chromophore or to alter local circulation or to provide thermal effect or to provide destructive effect or any combination of these actions.

In one embodiment the chromophore is delivered into the fat layer under the skin on the thigh using external ultrasound to enhance skin permeability and also enhance transport. The alteration of the stratum corneum alone or in combination with the ultrasound can further enhance delivery of the chromophore. External massage therapy from various techniques can be used to enhance the treatment process. In another embodiment chromophore is injected into the fat layer prior o treatment with light. Some light therapy with or without ultrasound may be used to photomodulate or photothermally or ultrasonically increase or otherwise alter the circulation or microcirculation or local metabolic processes in the areas affected by cellulite or other tissues. The proper light parameters are selected for the target adipocytes, blood vessels, exogenous chromophores, etc. Since some of the target tissues in cellulite are deeper than for example wrinkles or acne, typically long enough wavelengths of light must be utilized so that the light penetrated deeply enough to reach the target tissue.

Various topical or systemic agents can also be used to enhance the cellulite reduction treatments. Some of these include various cofactors for the metabolic or adipocyte interactions described and have been previously described herein.

Additional topical agents for inhibiting hair growth include inhibitors of ornithine decarboxylase, inhibitors of vascular endothelial growth factor (VEGF), inhibitors of phospholipase A2, inhibitors of S-adenosylmethionine. Specific examples of these, but not limited to, include licorice, licochalone A, genestein, soy isoflavones, phtyoestrogens, vitamin D and derivatives, analogs, conjugates, natural or synthetic versions or genetically engineered or altered or immunologic conjugates with these agents.

Also the same topical agents, exogenous light activated chromophores and treatments described fro cellulite above also are hereby incorporated into methods for reducing the growth of hair. Increasing the circulation or microcirculation of the hair bearing skin may also be accomplished by simply producing vasodilation by any method know to those skilled in this art. Some examples of topical agents which might be used to create such vasodilation include, but are not limited to: capsicum, ginseng, niacinamide, minoxidil, etc.

Other compositions that may be administered topically or systemically, in accordance with any embodiment of the invention disclosed here may include Vitamin C, Vitamin E, Vitamin A, Vitamin K, Vitamin F, Retin A (Tretinoin), Adapalene, Retinol, Hydroquinone, Kojic acid, a growth factor, echinacea, an antibiotic, an antifungal, an antiviral, a bleaching agent, an alpha hydroxy acid, a beta hydroxy acid, salicylic acid, antioxidant triad compound, a seaweed derivative, a salt water derivative, an antioxidant, a phytoanthocyanin, epigallocatechin-3-gallate, a phytonutrient, a botanical product, a herbaceous product, a hormone, an enzyme, a mineral, a genetically engineered substance, a cofactor, a catalyst, an antiaging substance, insulin, trace elements (including ionic calcium, magnesium, etc), minerals, Rogaine, a hair growth stimulating substance, a hair growth inhibiting substance, a dye, a natural or synthetic melanin, a metalloproteinase inhibitor, proline, hydroxyproline, an anesthetic substance, chlorophyll, copper chlorophyllin, chloroplasts, carotenoids, bacteriochlorophyll, phycobilins, carotene, xanthophyll, anthocyanin, and derivatives, subcomponents, and analogs of the above, both natural and synthetic, and mixtures thereof.

The present invention is further illustrated by way of the following examples.

Example 1

Acne Reduction

Continuous Treatment

A team of blinded expert graders viewing before and after photos of patients subjected to the non-ablative LILT ("Low Intensity Light Therapy") of the present invention score the global improvement of visible acne prominent in the facial area.

Six females are treated to reduce acne by, first, treating their skin with a topical composition containing about 2.5%, by weight copper chlorophyllin as the active ingredient. The treatment includes subjecting the target area of the patient's skin that has been treated with the topical composition to a filtered fluorescent light operated continuously and providing full-face coverage, i.e., the entire face of the patient is subjected to the light from the light source. Three treatments over 12 weeks to the entire face with at a light intensity of 11 milliwatts for 15 minutes per treatment session, resulting in a total energy exposure of 10.0 J/cm$^2$. Thermal injury is produced with blood vessels included among the target chromophores (but no skin wound care is needed). The average reduction in acne is shown in Table 1. The light source has a dominant emissive wavelength in the range of 410 nm to 420 nm and is centered at 415 nm.

TABLE 1

| Week/Value | Averaged Value of Reduction |
|---|---|
| 0 weeks | 0% |
| 4 weeks | 28% |
| 8 weeks | 56% |
| 12 weeks | 64% |

Example 2

Acne Reduction

Pulsed Treatment

A team of blinded expert graders viewing before and after photos of patients subjected to the non-ablative LILT ("Low Intensity Light Therapy") of the present invention score the global improvement of visible acne on the facial area.

Six females are treated for acne by, first, contacting their skin once nightly for each night during the 2 weeks preceding the treatment session with a topical composition containing a mixture of 2.0% chlorophyll a, 2.0% chlorophyll b, and 5% carotenoids as the active ingredients. The laser diode treatment includes subjecting the target area of the patient's skin that has been treated with the topical composition to a laser diode light having a pulse width of 800 msec and a pulse frequency of 1 hz (1 pulse per second). Three pulses are administered. Six treatments over 12 weeks to the entire face with 400 nm laser diode with a 10 cm beam diameter at an intensity ranging 2500 milliwatts/cm2. The average reduction in acne is shown in Table 2.

TABLE 2

| Week/Value | Averaged Value of Reduction |
|---|---|
| 0 weeks | 0% |
| 2 weeks | 36% |
| 7 weeks | 58% |
| 12 weeks | 82% |

Example 3

Acne and Acne Scarring Reduction Combined Continuous Wave/Pulsed Treatment

Three females showing active acne and acne scarring in the facial area are tested for improvement in scar prominence, skin texture, and scar visibility before and after receiving treatment in accordance with the non-ablative method of the present invention used in conjunction with a topical composition containing the active ingredient chlorophyll in a carrier suspension of microsponges having a diameter of 5 microns or less. Measurements are taken from by utilizing subjective evaluations conducted by trained medical personnel. The topical treatment includes applying the carotenoid composition containing about 5% carotenoids in a liposome carrier (alternatively, microsponges can be used having an average diameter of 5 microns) to the skin of the facial area and allowing it to penetrate the stratum corneum for approximately 15-20 minutes prior to beginning treatment. The first step in the treatment process is to expose the facial area to a continuous wave from a filtered metal halide lamp having a dominant emissive wavelength, i.e., an emission peak, at about 415 nm+/−5 nm and an energy output of 100 mW/cm² for approximately 10 minutes. The patient's facial area is then exposed to a pulsed LED treatment includes subjecting the target chromophore fibroblasts and subcellular components thereof to LED light having a pulse width of 250 msec and a pulse spacing of 250 msec for 90 pulses. Six treatments over 12 weeks to the entire face with the metal halide source as previously described and a 590 nm multichromatic LED, i.e., an LED having an emission peak at about 590 nm and putting out medically useful light in the range of about 585 nm to about 595 nm, at an intensity ranging from 1.05-2.05 µWatts. Further, the treatment maintains a skin temperature below the threshold of thermal injury. The average improvement in acne scar visibility is shown in Table 3. In accordance with the present invention, this dual-source treatment method employs the metal-halide light source to treat the active acne and the LED source to reduce or eliminate the visibility of acne scars.

TABLE 3

| | Percent Improvement | |
| --- | --- | --- |
| | Pre treatments | Post treatments (%) |
| Skin Elasticity | 0 | 85 |
| Scarring | 0 | 46 |
| Active Acne Lesions | 0 | 79 |

Example 4

Acne Scar Reduction

Pulsed Treatment

A team of blinded expert graders viewing before and after photos of patients subjected to the non-ablative LILT ("Low Intensity Light Therapy") of the present invention score the global improvement of visible acne scarring.

Six females were tested for reduction of acne scar visibility. The LED treatment includes subjecting the patient's skin to a LED light having a pulse width of 250 msec and a pulse spacing of 250 msec for a period of 90 pulses. Eight treatments over 16 weeks to the entire face with 590 nm multichromatic LED at an intensity ranging from 1.0-2.0 µWatts. Having a bandwidth of +/−5-15 nm, the LED therefore produces light in the wavelength range of from 575 nm to 605 nm. Further, the treatment maintains a skin temperature below the threshold of thermal injury. The average reduction in visible acne scarring is shown in Table 4.

TABLE 4

| Week/Value | Averaged Value of Reduction |
| --- | --- |
| 0 weeks | 0% |
| 4 weeks | 42% |
| 8 weeks | 51% |
| 12 weeks | 48% |

Example 5

Acne Reduction

Continuous Light

A method for treating acne by a combination of photothermal and photomodulatory treatment is used to reduce the presence of acne bacteria, resulting in a substantial reduction in the existence of acne on the facial area. In this example, dual chromophores are targeted a native, naturally occurring porphyrin in acne and an exogenous chromophor.

Pretreatment is performed using a topically applied chromophore. In this example, the topical chromophor is an aqueous solution of Na Cu Chlorophyllin and carotenoids is applied to the skin. The skin is first cleansed with a low residue cleansing solution and then a pH adjusting astringent lotion is applied by a 5-10 minute application of an enzyme mask for removing skin debris and a portion of the stratum corneum. The topical chromophore is applied and delivery of the chromophore is enhanced with a 3 megahertz ultrasound emitter using a duty cycle of 25% and 1.5 watts output using a massage-like motion to cover the entire face for 5 minutes and the shoulders for 5 minutes. Any excess lotion is then removed. The cleansing solution used for this example should include at least 40% of an acetone, ethyl acetate, or ethyl/isopropyl alcohol solvent, from about 1% to about 4% salicylic acid as a penetrate enhancer, and about 5% glycerin, included as a moisturizer.

A filtered fluorescent light source having a dominant emission at 420 nm is set to emit continuously for 20 minutes at an intensity of 10 Joules/cm². The entire face and upper back of the patient is treated with minimal overlap during each of 6 treatment sessions, each spaced two week apart. Approximately an 85% reduction in acne is observed.

Example 6

Home-Use Device and Treatment

The treatment method of Example 5 is carried out. The patient continues the treatment at home using a home-use device comprising a hand-held LED device, a lotion containing an aqueous solution of about 2%, by weight, chlorophyll and about 2%, by weight, of a carotenoid, and a wavelength selective sunscreen.

The patient applies a chlorophyll-containing topical solution to the areas previously treated for acne scarring once per day, preferably but not necessarily in the morning. Further, the patient applies a sunscreen typical of those known in the art except that it is formulated to permit the passage of radiation having a wavelength in the range of about 400 nm to about 420 nm and 600 nm to about 660 nm to allow natural sunlight to further aid the treatment process. The carotenoids provide protection to the skin against damage from ultraviolet radiation received from sunlight. Finally, the patient uses the hand-held LED device 1-2 times per day. The LED device emits radiation having a dominant emission at about 644 nm+/−5 nm at an energy output of approximately 20 microwatts in a continuous wave. Each treatment session covers active acne lesions for acne lesions for approximately 2 minutes. A further reduction in the visibility of acne scarring is observed. Additional improvement in acne scar reduction can be achieved using a 590 nm multichromatic LED at an intensity ranging from 1.0-2.0 µWatts as described in prior examples.

Example 7

Mixed LED Panel Treatment Array

An LED array includes both blue LEDs having a dominant emission at 415 nm to treat active acne and yellow LEDs having a dominant emission at 590 nm to treat acne scarring. The skin is pretreated in the same manner as described in Example 5. The LED array is then positioned to cover the entire facial area of the patient with a 20 minute continuous wave of blue light (415 nm) and an exposure of yellow (590 nm) light pulsed on for 250 milliseconds and off for 250 milliseconds. Approximately 100 pulses are delivered.

Example 8

Sebaceous Gland Size Reduction

Female skin exhibiting active ache rosacea and numerous sebaceoushyperplasia lesions is treated with a metal halide light source having a dominant emission centered at 415 nm+/−5 nm and an energy output of 100 mW/cm$^2$ for approximately 10 minutes after having been treated with a topically applied composition containing chlorophyll and carotenoids as the active ingredients. A mixture of 2.0% chlorophyll a and b, 6.0% carotenoids (carotenses and xanthophylls) and 1.5% phycobilin is used. All percentages are by weight. Three treatments are administered at two-week intervals. Visual inspection shows a reduction in sebaceous gland size of 40%-60%.

Example 9

Pulsed Treatment for Acne Bacteria

An LED array includes both blue LEDs having a dominant emission at 415 nm to treat active acne and yellow LEDs having a dominant emission at 590 nm to treat acne scarring. The skin is pretreated in the same manner as described in Example 5. The LED array is then positioned to cover the entire facial area of the patient with a 20 minute continuous wave of blue light (415 nm) and an exposure of yellow (590 nm) light pulsed on for 250 milliseconds and off for 250 milliseconds. Approximately 100 pulses are delivered.

The presently disclosed embodiments are to be considered in all respects as illustrative and not restrictive, the scope of the invention being indicated by the appended claims, rather than the foregoing description, and all changes which come within the meaning and range of equivalency of the claims are therefore intended to be embraced therein.

Treatment for UV Injured Cells

FIG. 5 illustrated the result of an experiment to determine the response of cells that have been injured by UVA1 light exposure (360 nm to 400 nm). Cells exposed to UVA1 light and receiving an energy fluence of 1.4 J/cm2 suffered a death rate of approximately 52%. Eight minutes after exposure to the UVA1 light, cells treated with a dual wavelength pulsed treatment according to the present invention at 590 nm and 870 nm (simultaneously) showed a recovery in cellular activity, resulting on a cell death rate of less than 5%. Cells treated with a combination of the dual wavelength treatment, in addition to UVA1 light, recovered somewhat, but yielded a cell death rate of about 34%.

Example 11

Treatment of Macular Degeneration

Figure 7:
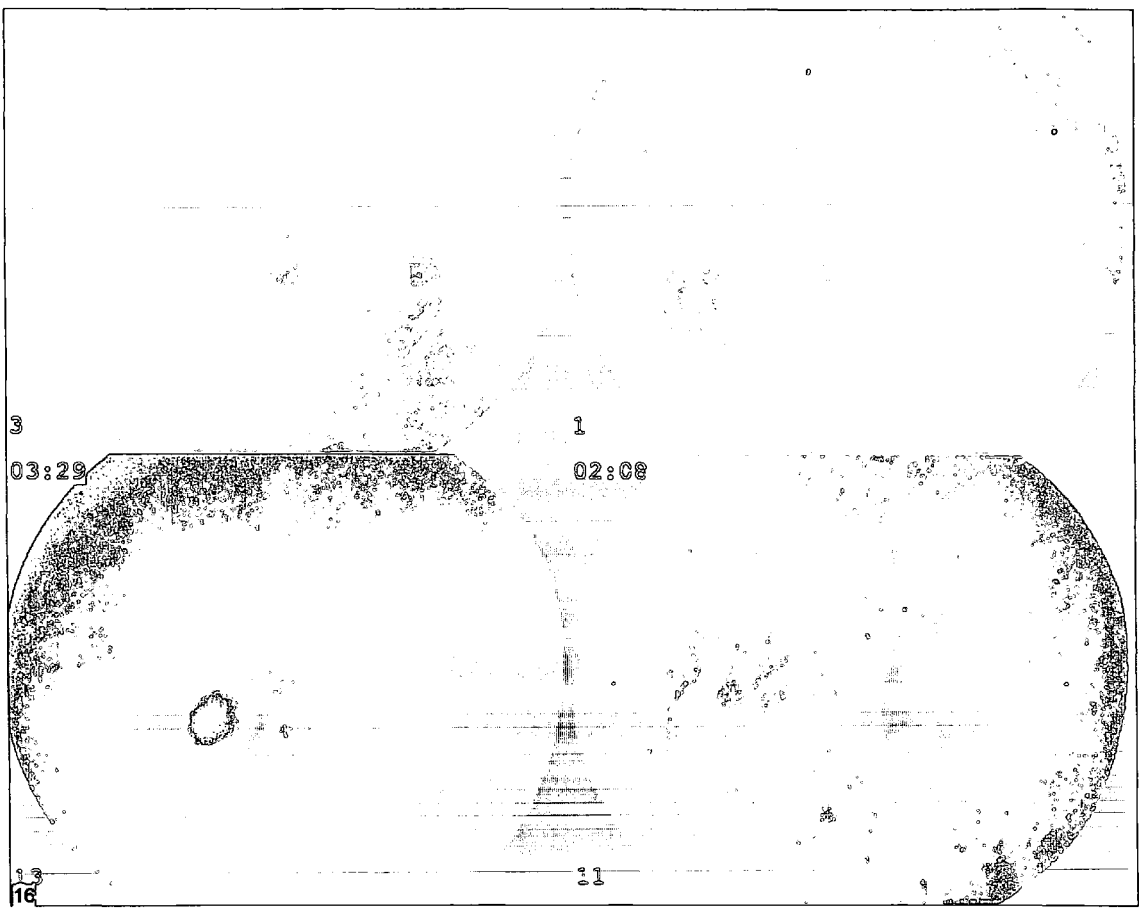
FIG. 7 is a photograph of the eyes of a patient suffering from wet macular degeneration prior to treatment according to the present invention.
Figure 8:
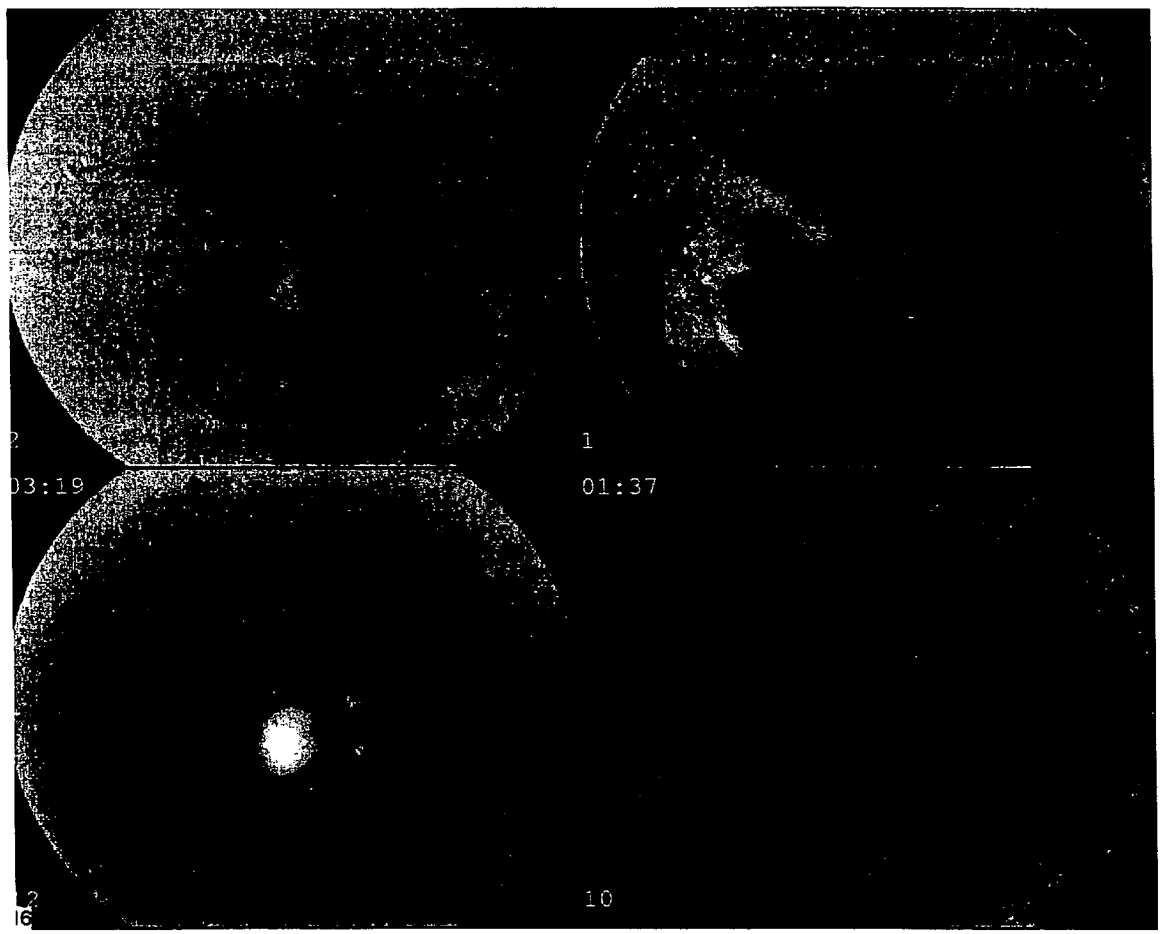
FIG. 8 is a photograph of the eyes of the patient of FIG. 6 after two weeks of treatment according to the present invention.

FIGS. 7 and 8 illustrate the effects of treatment of wet macular degeneration according to the present invention. The treatment was performed on an elderly woman and employed a dual wavelength pulsed treatment according to the present invention at 590 nm and 870 nm (simultaneously) using a 250/100/100 pulse code. FIG. 8 illustrates changes in the eyes of the subject, taken two weeks after the photographs of FIG. 7. Treatment was administered twice weekly and, afterward, the subject reported improvement in visual recognition and perception.

I claim:

1. A method, comprising:
   exposing target cells in a visual pathway to one or more sources of narrowband, multichromatic radiation having at least one dominant emissive wavelength between about 300 nm and about 1600 nm; and delivering an energy fluence to the target cells of less than or equal to 4.0 J/cm$^2$, wherein the energy fluence received at the target cells is from about 1 nanojoule/cm$^2$ to about 1 J/cm$^2$.

2. The method of claim 1 comprising a single source of narrowband, multichromatic radiation having a dominant emissive wavelength of from about 400 nm to about 900 nm.

3. The method of claim 1, wherein the one or more sources of narrowband, multichromatic radiation are selected from the group consisting of an a light emitting diode, a laser diode, a dye laser, metal halide lamps, a flashlamp, a mechanically filtered fluorescent light source, a mechanically filtered incandescent or filamentous light source, or combinations thereof.

4. The method of claim 1 comprising two or more sources of narrowband, multichromatic radiation, wherein the target cells are exposed to the two or more sources of narrowband, multichromatic radiation simultaneously or sequentially.

5. The method of claim 4 where a first source of narrowband, multichromatic radiation emits at a dominant emissive wavelength of about 590 nm and a second source of narrowband, multichromatic radiation emits light at a dominant emissive wavelength of about 870 nm.

6. The method of claim 1 or 5 wherein the energy fluence received at the target cells is from about 0.05 J/cm$^2$ to about 0.15 J/cm$^2$.

7. The method of claim 1 or 5 wherein the sources of narrowband, multichromatic radiation are pulsed.

8. The method of claim 7 wherein the sources of narrowband, multichromatic radiation are pulsed on for 250 milliseconds and are off for about 100 milliseconds.

9. The method of claim 8 wherein the sources of narrowband, multichromatic radiation are pulsed from about 1 to about 1000 times.

10. The method of claim 9 wherein the sources of narrowband, multichromatic radiation are pulsed about 100 times.

11. The method of claim 1 or 5 wherein the sources of narrowband, multichromatic radiation emit a continuous wave.

12. The method of claim 11 wherein the source of narrowband, multichromatic radiation emits for about 10 seconds to about 120 seconds.

13. The method of claim 12 wherein the source of narrowband, multichromatic radiation emits for about 25 seconds.

14. A method, comprising:
exposing cells undergoing oxidative stress to one or more sources of light having at least one dominant emissive wavelength between about 300 nm and about 1600 nm; delivering an energy fluence to the target cells of less than or equal to 4.0 J/cm$^2$, wherein the energy fluence received at the target cells is from about 1 nanojoule/cm$^2$ to about 1 J/cm$^2$;
wherein a decrease in the amount of free radicals released by the target cells undergoing oxidative stress is observed.

15. The method of claim 14 comprising a single source of light having a dominant emissive wavelength of from about 400 nm to about 900 nm.

16. The method of claim 14, wherein the one or more sources of light are selected from the group consisting of an a light emitting diode, a laser, a laser diode, a dye laser, metal halide lamps, a flashlamp, a mechanically filtered fluorescent light source, a mechanically filtered incandescent or filamentous light source, or combinations thereof.

17. The method of claim 14 wherein an energy density of the one or more sources of light is less than 10 mw/cm$^2$.

18. The method of claim 14 wherein an energy density of the one or more sources of light is less than about 4 mw/cm$^2$.

19. A method, comprising: exposing target cells that have been subject to acute or chronic injury or degenerative changes to a one or more sources of light having at least one dominant emissive wavelength between about 300 nm and about 1600 nm; delivering an energy fluence to the target cells of less than 4.0 J/cm$^2$, wherein the energy fluence received at the target cells is from about 1 nanojoule/cm$^2$ to about 1 J/cm$^2$; and
wherein a restoration of a function of the target cells prior to being subject to acute or chronic injury or degenerative changes is observed.

20. The method of claim 19 comprising a single source of light having a dominant emissive wavelength of from about 400 nm to about 900 nm.

21. The method of claim 19, wherein the one or more sources of light are selected from the group consisting of an a light emitting diode, a laser, a laser diode, a dye laser, metal halide lamps, a flashlamp, a mechanically filtered fluorescent light source, a mechanically filtered incandescent or filamentous light source, or combinations thereof.

22. The method of claim 19 wherein an energy density of the one or more sources of light is less than 10 mw/cm$^2$.

23. The method of claim 19 wherein an energy density of the one or more sources of light is less than about 4 mw/cm$^2$.

* * * * *